US012661032B2

(12) United States Patent
Zhai et al.

(10) Patent No.: US 12,661,032 B2
(45) Date of Patent: Jun. 23, 2026

(54) METHODS AND SYSTEMS FOR DETERMINING BODY LUMEN SIZE

(71) Applicant: Otsuka Medical Devices Co., Ltd., Tokyo (JP)

(72) Inventors: Liang Zhai, Belmont, CA (US); Eric Dailey, San Jose, CA (US); James D. Mazzone, San Jose, CA (US); Robin Bek, Campbell, CA (US); Neil Barman, Menlo Park, CA (US); Shruthi Thirumalai, Fremont, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 927 days.

(21) Appl. No.: 17/813,029

(22) Filed: Jul. 15, 2022

(65) Prior Publication Data

US 2023/0027712 A1    Jan. 26, 2023

Related U.S. Application Data

(60) Provisional application No. 63/367,119, filed on Jun. 27, 2022, provisional application No. 63/223,519, (Continued)

(51) Int. Cl.
A61B 5/107 (2006.01)
A61B 5/00 (2006.01)
(Continued)

(52) U.S. Cl.
CPC .......... A61B 5/1076 (2013.01); A61B 5/6853 (2013.01); A61B 5/7271 (2013.01);
(Continued)

(58) Field of Classification Search
CPC ........ A61B 2090/061; A61B 2090/064; A61B 90/06; A61B 18/1492; A61B 2018/0022;
(Continued)

(56) References Cited

U.S. PATENT DOCUMENTS

| | | | |
|---|---|---|---|
| 4,554,925 A | 11/1985 | Young | |
| 4,643,186 A | 2/1987 | Rosen | |

(Continued)

FOREIGN PATENT DOCUMENTS

| | | |
|---|---|---|
| AU | 2011/239363 | 5/2012 |
| CA | 2895995 | 6/2014 |

(Continued)

OTHER PUBLICATIONS

Glier, Tomke E., "Functional Printing of Conductive Silver-Nanowire Photopolymer Composites," Scientific Reports 9: 6465, Apr. 23, 2019.

(Continued)

*Primary Examiner* — Khadijeh A Vahdat

(74) *Attorney, Agent, or Firm* — Theresa Ann Raymer

(57) ABSTRACT

A tissue treatment system and method of using the tissue treatment system determines a size of a body lumen, or a neuromodulation parameter corresponding to the size of the body lumen. The tissue treatment system fills a balloon with a fluid when the balloon is within a body lumen. A fluid parameter of the fluid is detected over a period of time. A parameter curve of the fluid parameter is determined. The parameter curve includes the fluid parameter versus an independent variable over the period of time. The system compares the parameter curve of the fluid parameter to a reference curve and, based on the comparison, determine the body lumen size or the neuromodulation parameter. Other embodiments are also described and claimed.

31 Claims, 23 Drawing Sheets

Related U.S. Application Data filed on Jul. 19, 2021, provisional application No. 63/223,517, filed on Jul. 19, 2021.

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00404* (2013.01); *A61B 2018/00577* (2013.01); *A61B 2562/168* (2013.01)

(58) Field of Classification Search
CPC ........... A61B 2018/00404; A61B 2018/00577; A61B 2562/168; A61B 5/1076; A61B 5/6853; A61B 5/7271
See application file for complete search history.

(56) References Cited

U.S. PATENT DOCUMENTS

| | | | |
|---|---|---|---|
| 4,650,466 A | 3/1987 | Luther | |
| 4,709,698 A | 12/1987 | Johnston et al. | |
| 4,841,977 A | 6/1989 | Griffith et al. | |
| 4,983,169 A | 1/1991 | Furukawa | |
| 5,000,185 A | 3/1991 | Yock | |
| 5,114,423 A | 5/1992 | Kasprzyk | |
| 5,368,591 A | 11/1994 | Lennox | |
| 5,391,197 A | 2/1995 | Burdette et al. | |
| 5,423,811 A | 6/1995 | Imran et al. | |
| 5,447,497 A | 9/1995 | Sogard et al. | |
| 5,558,672 A | 9/1996 | Edwards et al. | |
| 5,575,788 A | 11/1996 | Baker et al. | |
| 5,657,755 A | 8/1997 | Desai | |
| 5,685,839 A | 11/1997 | Edwards et al. | |
| 5,688,266 A | 11/1997 | Edwards et al. | |
| 5,752,522 A | 5/1998 | Murphy | |
| 5,800,482 A | 9/1998 | Pomeranz et al. | |
| 5,840,031 A | 11/1998 | Crowley | |
| 6,066,134 A | 5/2000 | Eggers et al. | |
| 6,097,985 A | 8/2000 | Kasevich et al. | |
| 6,117,101 A | 9/2000 | Diederich et al. | |
| 6,254,598 B1 | 7/2001 | Edwards | |
| 6,283,989 B1 | 9/2001 | Laufer et al. | |
| 6,292,695 B1 | 9/2001 | Webster | |
| 6,296,619 B1 | 10/2001 | Brisken et al. | |
| 6,383,151 B1 | 5/2002 | Diederich et al. | |
| 6,514,249 B1 | 2/2003 | Maguire et al. | |
| 6,529,756 B1 | 3/2003 | Phan | |
| 6,564,096 B2 | 5/2003 | Mest | |
| 6,575,933 B1 | 6/2003 | Wittenberger et al. | |
| 6,584,360 B2 | 6/2003 | Francischelli et al. | |
| 6,635,054 B2 | 10/2003 | Fjield et al. | |
| 6,648,883 B2 | 11/2003 | Francischelli et al. | |
| 6,669,655 B1 | 12/2003 | Acker | |
| 6,692,490 B1 | 2/2004 | Edwards | |
| 6,719,755 B2 | 4/2004 | Sliwa, Jr. et al. | |
| 6,763,722 B2 | 7/2004 | Fjield et al. | |
| 6,837,886 B2 | 1/2005 | Collins | |
| 6,845,267 B2 | 1/2005 | Harrison et al. | |
| 6,954,977 B2 | 10/2005 | Maguire | |
| 6,958,064 B2 | 10/2005 | Rioux et al. | |
| 7,052,695 B2 | 5/2006 | Kalish | |
| 7,156,816 B2 | 1/2007 | Schwartz et al. | |
| 7,162,303 B2 | 1/2007 | Levin et al. | |
| 7,371,231 B2 | 5/2008 | Rioux et al. | |
| 7,510,536 B2 | 3/2009 | Foley et al. | |
| 7,540,846 B2 | 6/2009 | Harhen et al. | |
| 7,617,005 B2 | 11/2009 | Demarais et al. | |
| 7,621,873 B2 | 11/2009 | Owen et al. | |
| 7,653,438 B2 | 1/2010 | Deem et al. | |
| 7,717,948 B2 | 5/2010 | Demarais et al. | |
| 7,837,676 B2 | 11/2010 | Sinelnikov et al. | |
| 7,942,871 B2 | 5/2011 | Thapliyal et al. | |
| 8,024,050 B2 | 9/2011 | Libbus et al. | |
| 8,025,688 B2 | 9/2011 | Diederich et al. | |
| 8,137,274 B2 | 3/2012 | Weng et al. | |
| 8,167,805 B2 | 5/2012 | Emery et al. | |
| 8,333,757 B2 | 12/2012 | Mazzone et al. | |
| 8,447,414 B2 | 5/2013 | Johnson et al. | |
| 8,480,619 B2 | 7/2013 | Porter | |
| 8,483,831 B1 | 7/2013 | Hiavka et al. | |
| 8,626,300 B2 | 1/2014 | Demarais et al. | |
| 8,696,612 B2 | 4/2014 | Wilson et al. | |
| 8,702,619 B2 | 4/2014 | Wang | |
| 8,774,913 B2 | 7/2014 | Demarais et al. | |
| 8,790,281 B2 | 7/2014 | Diederich et al. | |
| 8,818,514 B2 | 8/2014 | Zarins et al. | |
| 8,845,629 B2 | 9/2014 | Demarais et al. | |
| 8,932,289 B2 | 1/2015 | Mayse et al. | |
| 9,022,948 B2 | 5/2015 | Wang | |
| 9,023,037 B2 | 5/2015 | Zarins et al. | |
| 9,028,472 B2 | 5/2015 | Mathur et al. | |
| 9,066,720 B2 | 6/2015 | Ballakur et al. | |
| 9,072,902 B2 | 7/2015 | Mathur et al. | |
| 9,155,590 B2 | 10/2015 | Mathur | |
| 9,162,040 B2 | 10/2015 | Vo et al. | |
| 9,186,198 B2 | 11/2015 | Demarais et al. | |
| 9,186,212 B2 | 11/2015 | Nabulovsky et al. | |
| 9,289,132 B2 | 3/2016 | Ghaffari | |
| 9,326,816 B2 | 5/2016 | Srivastava | |
| 9,327,123 B2 | 5/2016 | Yamasaki | |
| 9,333,035 B2 | 5/2016 | Rudie | |
| 9,339,332 B2 | 5/2016 | Srivastava | |
| 9,345,530 B2 | 5/2016 | Ballakur et al. | |
| 9,375,154 B2 | 6/2016 | Wang | |
| 9,415,242 B2 | 8/2016 | Wilson et al. | |
| 9,427,579 B2 | 8/2016 | Fain et al. | |
| 9,439,598 B2 | 9/2016 | Shimada et al. | |
| 9,649,064 B2 | 5/2017 | Toth et al. | |
| 9,700,372 B2 | 7/2017 | Schaer | |
| 9,707,034 B2 | 7/2017 | Schaer | |
| 9,723,998 B2 | 8/2017 | Wang | |
| 9,730,639 B2 | 8/2017 | Toth et al. | |
| 9,743,845 B2 | 8/2017 | Wang | |
| 9,750,560 B2 | 9/2017 | Ballakur et al. | |
| 9,770,291 B2 | 9/2017 | Wang et al. | |
| 9,770,593 B2 | 9/2017 | Gross | |
| 9,801,684 B2 | 10/2017 | Fain | |
| 9,820,811 B2 | 11/2017 | Wang | |
| 9,907,983 B2 | 3/2018 | Thapliyal et al. | |
| 9,931,047 B2 | 4/2018 | Srivastava | |
| 9,943,666 B2 | 4/2018 | Warnking | |
| 9,956,034 B2 | 5/2018 | Toth et al. | |
| 9,968,790 B2 | 5/2018 | Toth et al. | |
| 9,981,108 B2 | 5/2018 | Warnking | |
| 9,999,463 B2 | 6/2018 | Puryear et al. | |
| 10,004,458 B2 | 6/2018 | Toth et al. | |
| 10,004,557 B2 | 6/2018 | Gross et al. | |
| 10,010,364 B2 | 7/2018 | Harringtpm | |
| 10,016,233 B2 | 7/2018 | Pike | |
| 10,022,085 B2 | 7/2018 | Toth et al. | |
| 10,039,901 B2 | 8/2018 | Warnking | |
| 10,123,903 B2 | 11/2018 | Warnking et al. | |
| 10,143,419 B2 | 12/2018 | Toth et al. | |
| 10,179,020 B2 | 1/2019 | Ballakur et al. | |
| 10,179,026 B2 | 1/2019 | Ng | |
| 10,182,865 B2 | 1/2019 | Naga et al. | |
| 10,226,633 B2 | 3/2019 | Toth et al. | |
| 10,245,429 B2 | 4/2019 | Deem et al. | |
| 10,292,610 B2 | 5/2019 | Srivastava | |
| 10,293,190 B2 | 5/2019 | Zarins et al. | |
| 10,350,440 B2 | 7/2019 | Taylor | |
| 10,363,359 B2 | 7/2019 | Toth et al. | |
| 10,368,775 B2 | 8/2019 | Hettrick et al. | |
| 10,368,944 B2 | 8/2019 | Schaer | |
| 10,376,310 B2 | 8/2019 | Fain et al. | |
| 10,383,685 B2 | 8/2019 | Gross et al. | |
| 10,398,332 B2 | 9/2019 | Min et al. | |
| 10,456,605 B2 | 10/2019 | Taylor | |
| 10,470,684 B2 | 11/2019 | Toth et al. | |
| 10,478,249 B2 | 11/2019 | Gross et al. | |

(56)                References Cited

U.S. PATENT DOCUMENTS

| | | |
|---|---|---|
| 10,499,877 B2 | 12/2019 | Peng et al. |
| 10,499,937 B2 | 12/2019 | Warnking |
| 10,543,037 B2 | 1/2020 | Shah |
| 10,850,091 B2 | 12/2020 | Zarins et al. |
| 11,007,001 B1 | 5/2021 | Carignan et al. |
| 11,305,098 B2 | 4/2022 | Zhou et al. |
| 11,801,085 B2 | 10/2023 | Wu et al. |
| 2001/0008976 A1 | 7/2001 | Wang |
| 2001/0023365 A1 | 9/2001 | Medhkour et al. |
| 2002/0042610 A1 | 4/2002 | Sliwa, Jr. et al. |
| 2002/0072741 A1 | 6/2002 | Sliwa, Jr. et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0028111 A1 | 2/2003 | Vaezy et al. |
| 2003/0074039 A1 | 4/2003 | Puskas |
| 2003/0114878 A1 | 6/2003 | Diederich et al. |
| 2003/0125726 A1 | 7/2003 | Maguire et al. |
| 2003/0181963 A1 | 9/2003 | Pellegrino et al. |
| 2003/0216721 A1 | 11/2003 | Diederich et al. |
| 2003/0216792 A1 | 11/2003 | Levin |
| 2004/0019349 A1 | 1/2004 | Fuimaono et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0181178 A1 | 9/2004 | Aldrich et al. |
| 2004/0242999 A1 | 12/2004 | Vitek et al. |
| 2005/0035901 A1 | 2/2005 | Lyon |
| 2005/0038340 A1 | 2/2005 | Vaezy et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0261672 A1 | 11/2005 | Deem et al. |
| 2005/0288730 A1 | 12/2005 | Deem |
| 2006/0041277 A1 | 2/2006 | Deem et al. |
| 2006/0052695 A1 | 3/2006 | Adam et al. |
| 2006/0058711 A1 | 3/2006 | Harhen et al. |
| 2006/0064081 A1 | 3/2006 | Rosinko |
| 2006/0118127 A1 | 6/2006 | Chinn |
| 2006/0142827 A1 | 6/2006 | Willard et al. |
| 2006/0184069 A1 | 8/2006 | Vaitekunas |
| 2006/0217772 A1 | 9/2006 | Libbus et al. |
| 2006/0235286 A1 | 10/2006 | Stone et al. |
| 2007/0060921 A1 | 3/2007 | Janssen et al. |
| 2007/0072741 A1 | 3/2007 | Robideau |
| 2007/0106292 A1 | 5/2007 | Kaplan |
| 2007/0112300 A1 | 5/2007 | Roman et al. |
| 2007/0135875 A1 | 6/2007 | Demarais et al. |
| 2008/0039746 A1 | 2/2008 | Hissong et al. |
| 2008/0215031 A1 | 9/2008 | Belfort et al. |
| 2009/0012513 A1 | 1/2009 | Utley et al. |
| 2009/0178289 A1 | 7/2009 | Sakai et al. |
| 2009/0234407 A1 | 9/2009 | Hastings et al. |
| 2009/0248005 A1 | 10/2009 | Rusin et al. |
| 2010/0130926 A1 | 5/2010 | Lee et al. |
| 2010/0168570 A1 | 7/2010 | Sliwa et al. |
| 2011/0118723 A1 | 5/2011 | Turner et al. |
| 2011/0125206 A1 | 5/2011 | Bornzin |
| 2011/0208096 A1 | 8/2011 | Demarais et al. |
| 2012/0004656 A1 | 1/2012 | Jackson et al. |
| 2012/0265069 A1 | 10/2012 | Sliwa et al. |
| 2012/0265198 A1 | 10/2012 | Crow et al. |
| 2012/0296232 A1 | 11/2012 | Ng |
| 2013/0023897 A1 | 1/2013 | Wallace |
| 2013/0085489 A1 | 4/2013 | Fain et al. |
| 2013/0090649 A1 | 4/2013 | Smith et al. |
| 2013/0096550 A1 | 4/2013 | Hill |
| 2013/0116737 A1 | 5/2013 | Edwards et al. |
| 2013/0123770 A1 | 5/2013 | Smith |
| 2013/0131743 A1 | 5/2013 | Yamasaki et al. |

| | | | |
|---|---|---|---|
| 2013/0137980 A1 | 5/2013 | Waters et al. | |
| 2013/0150749 A1 | 6/2013 | McLean et al. | |
| 2013/0165925 A1 | 6/2013 | Mathur et al. | |
| 2013/0172872 A1 | 7/2013 | Subramaniam | |
| 2013/0274614 A1 | 10/2013 | Shimada et al. | |
| 2013/0289369 A1 | 10/2013 | Margolis | |
| 2013/0289682 A1 | 10/2013 | Barman et al. | |
| 2014/0018788 A1 | 1/2014 | Engelman et al. | |
| 2014/0058294 A1 | 2/2014 | Gross et al. | |
| 2014/0257266 A1 | 9/2014 | Kasprzyk et al. | |
| 2014/0257271 A1 | 9/2014 | Mayse et al. | |
| 2014/0274614 A1 | 9/2014 | Min et al. | |
| 2014/0275924 A1 | 9/2014 | Min et al. | |
| 2014/0288551 A1 | 9/2014 | Bharmi et al. | |
| 2014/0288616 A1 | 9/2014 | Rawat et al. | |
| 2014/0303617 A1 | 10/2014 | Shimada | |
| 2015/0066069 A1* | 3/2015 | Drasler | A61M 29/02 |
| | | | 606/194 |
| 2015/0119877 A1 | 4/2015 | Jameson et al. | |
| 2015/0289931 A1 | 10/2015 | Puryear et al. | |
| 2015/0360007 A1 | 12/2015 | Schneider et al. | |
| 2016/0000345 A1 | 1/2016 | Kobayashi et al. | |
| 2016/0045121 A1 | 2/2016 | Akingba et al. | |
| 2016/0095652 A1 | 4/2016 | Lee et al. | |
| 2016/0183807 A1* | 6/2016 | Schoenle | A61B 8/12 |
| | | | 600/479 |
| 2017/0027460 A1 | 2/2017 | Shimada et al. | |
| 2017/0035310 A1 | 2/2017 | Shimada et al. | |
| 2017/0156705 A1 | 6/2017 | Galluzzo et al. | |
| 2017/0296264 A1 | 10/2017 | Wang | |
| 2018/0022108 A1 | 1/2018 | Mori et al. | |
| 2018/0042670 A1 | 2/2018 | Wang et al. | |
| 2018/0064359 A1 | 3/2018 | Pranaitis | |
| 2018/0078307 A1 | 3/2018 | Wang et al. | |
| 2018/0185091 A1 | 7/2018 | Toth et al. | |
| 2018/0221087 A1 | 8/2018 | Puryear et al. | |
| 2018/0249958 A1 | 9/2018 | Toth et al. | |
| 2018/0250054 A1 | 9/2018 | Gross et al. | |
| 2018/0280082 A1 | 10/2018 | Puryear et al. | |
| 2018/0289320 A1 | 10/2018 | Toth et al. | |
| 2018/0310991 A1 | 11/2018 | Pike | |
| 2018/0333204 A1 | 11/2018 | Ng | |
| 2019/0046111 A1 | 2/2019 | Toth et al. | |
| 2019/0046264 A1 | 2/2019 | Toth et al. | |
| 2019/0076191 A1 | 3/2019 | Wang | |
| 2019/0110704 A1 | 4/2019 | Wang | |
| 2019/0134396 A1 | 5/2019 | Toth et al. | |
| 2019/0151670 A1 | 5/2019 | Toth et al. | |
| 2019/0183560 A1 | 6/2019 | Ballakur et al. | |
| 2019/0252088 A1 | 8/2019 | Lin et al. | |
| 2019/0307361 A1 | 10/2019 | Hettrick et al. | |
| 2019/0314617 A1* | 10/2019 | Harmouche | A61M 25/10 |
| 2019/0378633 A1 | 12/2019 | Hu et al. | |
| 2020/0046248 A1 | 2/2020 | Toth et al. | |
| 2020/0077907 A1 | 3/2020 | Shimada et al. | |
| 2020/0084539 A1 | 3/2020 | Lippert et al. | |
| 2020/0197088 A1 | 6/2020 | Vrba et al. | |
| 2021/0177344 A1 | 6/2021 | Neidert et al. | |
| 2021/0178194 A1 | 6/2021 | Sverdlik et al. | |
| 2022/0095979 A1 | 3/2022 | Shimada et al. | |

FOREIGN PATENT DOCUMENTS

| | | |
|---|---|---|
| CA | 2925946 | 5/2015 |
| EP | 0706345 | 2/2003 |
| EP | 1299035 | 4/2003 |
| EP | 1503685 | 2/2005 |
| EP | 1579889 | 9/2005 |
| EP | 1351738 | 1/2007 |
| EP | 2415495 | 10/2010 |
| EP | 2359764 | 8/2011 |
| EP | 2430996 | 3/2012 |
| EP | 2842604 | 3/2015 |
| EP | 2865350 | 4/2015 |
| EP | 2968984 | 1/2016 |
| EP | 2995250 | 3/2016 |
| EP | 2809253 | 4/2016 |
| EP | 2734259 | 11/2016 |
| EP | 3245962 | 11/2017 |

(56) References Cited

FOREIGN PATENT DOCUMENTS

| EP | 3368156 | 2/2020 |
|----|---------|--------|
| EP | 3799931 | 4/2021 |
| WO | WO 95/17131 | 6/1995 |
| WO | WO 99/002096 | 1/1999 |
| WO | WO 2001/087169 | 11/2001 |
| WO | WO2001/095820 | 12/2001 |
| WO | WO2002/005897 | 1/2002 |
| WO | WO 2002/019934 | 3/2002 |
| WO | WO2003/022167 | 3/2003 |
| WO | WO2003/051450 | 6/2003 |
| WO | WO 2005/070316 | 8/2005 |
| WO | WO2006/041881 | 4/2006 |
| WO | WO2006/060053 | 6/2006 |
| WO | WO 2007/001981 | 1/2007 |
| WO | WO2007/014003 | 2/2007 |
| WO | WO 2007/036035 | 4/2007 |
| WO | WO 2008/099424 | 2/2008 |
| WO | WO 2009/036424 | 3/2009 |
| WO | WO 2012/112165 | 8/2012 |
| WO | WO 2013/154776 | 10/2013 |
| WO | WO 2014/210450 | 12/2014 |
| WO | WO 2015/057411 | 4/2015 |
| WO | WO 2015/103541 | 7/2015 |
| WO | WO 2017/099950 | 6/2017 |

OTHER PUBLICATIONS

International Search Report and Written Opinion dated Oct. 19, 2022 in International Application No. PCT/IB2022/056571.

International Search Report and Written Opinion dated Oct. 19, 2022 in International Application No. PCT/IB2022/056563.

Saab, Mark A., "Applications of High-Pressure Balloons in the Medical Device Industry," Medical Device & Diagnostic Industry Magazine, 2000.

Schueler, Beth A. et al., "Risk Factors Leading to Cerebral Arterial Rupture by Intravascular Balloon," AJNR: 14, pp. 1085-1093, 1993.

Tautorat, Carsten et al., "Balloon-based measuring system for compliance investigations," Current Directions in Biomedical Engineering 2018: 4(1): pp. 539-542, 2018.

Van Der Giessen, Willem J. et al., "A New Intracoronary Measurement Catheter, Metricath, Compared to Intravascular Ultrasound and Quantitative Coronary Angiography in a Stented Porcine Coronary Model," Catheterization and Cardiovascular Interventions, 57: pp. 2-9, 2002.

Wang, Paul J., "Overview of Balloon Approaches to AF Ablation," Journal of the American College of Cardiology, vol. 68, No. 25, 2016.

Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.

Calkins, Hugh et al., "Temperature Monitoring During Radiofrequency Catheter Ablation Procedures Using Closed Loop Control," Circulation vol. 90, No. 3, p. 1279-1286, Sep. 1994.

Deardorff, Dana L. et al., "Control of interstitial thermal coagulation: Comparative evaluation of microwave and ultrasound applicators," Medical Physics vol. 28, No. 1, p. 104-117, Jan. 2001.

Dinerman, Jay L. et al., "Temperature Monitoring During Radiofrequency Ablation," Journal of Cardiovascular Electrophysiology, vol. 7 No. 2, p. 163-173, Feb. 1996.

Esler, Murray et al., "The future of renal denervation," Autonomic Neuroscience: Basic and Clinical, vol. 204, p. 131-138, May 2017.

Filonenko, E.A. et al., "Heating of Biological Tissues by Two-Dimensional Phased Arrays with Random and Regular Element Distributions," Acoustical Physics, vol. 50 No. 2, p. 222-231, 2004.

Fry, William J., "Action of Ultrasound on Nerve Tissue—A review," The Journal of the Acoustical Society of America, vol. 25 No. 1, p. 1-5, Jan. 1953.

Fry, Frank J., "Precision High Intensity Focusing Ultrasonic Machines for Surgery," High Intensity Focused U.S., 152-156, Sep. 6-7, 1957.

Haines, David, "Biophysics of Ablation: Application to Technology," Journal of Cardiovascular Electrophysiology, vol. 15, No. 10, p. S2-S11, Oct. 2004.

Hynynen, K. et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging-Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.

Lafon, C. et al., "Design and Preliminary Results of an Ultrasound Applicator for Interstitial Thermal Coagulation," Ultrasound in Medicine & Biology, vol. 24, No. 1, p. 113-122, 1998.

Lewis, Matthew A. et al., "Thermometry and Ablation Monitoring with Ultrasound," Int. J. Hyperthermia vol. 31, Issue 2, p. 163-181, Mar. 2015.

Liu, Xinmeng et al., "Visualization and mapping of the right phrenic nerve by intracardiac echocardiography during atrial fibrillation ablation," Europace vol. 25, p. 1352-1360, 2023.

Mendelsohn, Farrell O., "Microanatomy of the Renal Sympathetic Nervous System," Endovascular Today, p. 59-62, Oct. 2013.

Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.

Quadri, Syed A. et al., "High-intensity focused ultrasound: past, present, and future in neurosurgery," Neurosurgical Focus, vol. 44, No. 2, p. 1-9, Feb. 2018.

Ross, Anthony B. et al., "Highly directional transurethral ultrasound applicators with rotational control for MRI-guided prostatic thermal therapy," Physics in Medicine & Biology, vol. 49, p. 189-204, Jan. 2004.

Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.

Sanghvi, Kintur et al., "Rationale and design for studies of renal denervation in the absence (Spyral HTN Off-Med) and presence (Spyral HTN On-Med) of antihypertensive medications," American Heart Journal, vol. 180, p. e1-e2. Oct. 2016.

Satou, Shunsuke et al., "Observation of renal sympathetic nerves by intravascular ultrasound," Hypertension Research vol. 42, p. 1092-1094, 2019.

Schmidt, Boris et al., "Balloon Catheters for Pulmonary Vein Isolation," Herz vol. 33, p. 580-584, 2008.

Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.

Stauffer, P.R. et al., "13 Interstitial Heating Technologies," Thermoradiotherapy and Thermochemotherapy, p. 279-320, 1995.

Swanson, David K. et al., "Tissue temperature Feedback Control of Power, The Key to Successful Ablation," Innovations, vol. 6 No. 4, p. 276-282, Jul./Aug. 2011.

Tabei, Makoto et al., "A k-space method for coupled first-order acoustic propagation equations," J. Acoust. Soc. Am., vol. 111, No. 1, pt. 1, p. 53-63, Jan. 2002.

Tzafriri, Abraham R. et al., "Innervation Patterns May Limit Response to Endovascular Renal Denervation," Journal of the American College of Cardiology, vol. 64, No. 11, p. 1079-1087, Sep. 2014.

Umemura, Shin-ichiro, "Focused ultrasound transducer for thermal treatment," International Journal of Hyperthermia, vol. 31, No. 2, p. 216-221, 2015.

Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.

Zivin, Adam, et al., "Temperature Monitoring versus Impedance Monitoring during RF Catheter Ablation," Radiofrequency Catheter

(56)                    References Cited

OTHER PUBLICATIONS

Ablation of Cardiac Arrhythmias, Basic Concepts and Clinical Applications, Second Edition, Edited by Shoei K. Stephen Huang, MD & David J. Wilber, MD, p. 103-112, 2000.

Accornero, Neri et al., "Selective Activation of Peripheral Nerve Fibre Groups of Different Diameter By Triangular Shaped Stimulus Pulses", J. Physiol. (1977), 273, 539-560, 22 Q9S.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).

American Heart Association—Pulmonary Hypertension: High Blood Pressure in the Heart-to-Lung System, (last reviewed Oct. 31, 2016).

Appeal Brief of Patent Owner from Reexamination 95-002, 110.

Aytac, et al., "Correlation Between the Diameter of the Main Renal Artery and the Presence of an Accessory Renal Artery", J Ultrasound Med 22:433-439, 2003.

Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).

Bailey, M.R. et al., Physical Mechanisms of the Therapeutic Effect of Ultrasound (A Review), Acoustical Physics, vol. 49, No. 4, 2003, pp. 369-388.

Bengel, et al., Serial Assessment of Sympathetic Reinnervation After Orthotopic Heart Transplantation; A Longitudinal Study Using PET and C-11 Hydroxyephedrine, Circulation. 1999;99:1866-1871.

Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.

Bhatt, D.L., et al., A Controlled Trial of Renal Denervation for Resistant Hypertension, New England J. Med., 370:1393-1401 (2014).

Bhatt, Deepak L. et al., Long-term outcomes after catheter-based renal artery denervation for resistant hypertension: final follow-up of the randomised Symplicity HTN-3 Trial, 400 Lancet 1405 (2022).

Billard, B.E. et al., Effects of Physical Parameters on High Temperature Ultrasound Hyperthermia, Ultrasound in Med. & Biol. vol. 16, No. 4, pp. 409-420,1990.

Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

Blanketjin, Peter, Sympathetic Hyperactivity in Chronic Kidney Disease, Neprhrol Dial Transplant, vol. 19, No. 6, 1354-1357 (2004).

Blum et al., Treatment of Ostial Renal-Artery Stenoses with Vascular Endoprostheses after Unsuccessful Balloon Angioplasty, N. Engl. J. Med. 336 459-65 (1997).

Bonsignore, C., "A Decade of Evolution in Stent Design", Proceedings of the International Conference on Shape Memory and Superelastic Technologies, (2003).

Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).

Bush, et al., "Endovascular revascularization of renal artery stenosis: Technical and clinical results", Journal of Vascular Surgery, May 2001, 1041-1049 (2001).

Camasao, D. B. et al., The mechanical characterization of blood vessels and their substitutes in the continuous quest for physiological-relevant performances: A critical review, Materials Today Bio, vol. 10 (2021).

Carter, J., "Microneurography and Sympathetic Nerve Activity: A Decade-By-Decade Journey across 50 Years," Journal of Neurophysiology, vol. 121, No. 4. doi: 10.1 152/jn.00570.2018.

Carter, Stefan et al., Measurement of Renal Artery Pressures by Catheterization in Patients with and without Renal Artery Stenosis, Circulation, vol. XXXIII, 443-449 (1966).

Chapelon, J.Y., "Treatment of Localised Prostate Cancer with Transrectal High Intensity Focused Ultrasound,"European Journal of Ultrasound 9, 31-38, 1999.

Charlesworth, Peter et al., Renal Artery Injury from a Fogarty Balloon Catheter, Journal of Vascular Surgery, vol. 1, No. 4, 573-576 (1984).

Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Chiesa et al., Endovascular Stenting for the Nutcracker Phenomenon, J. Endovasc. Ther., 8:652-655 (2001).

Coates, Paul et al., "Time, Temperature, Power, and Impedance Considerations for Radiofrequency Catheter Renal Denervation," Cardiovascular Revascularization Medicine 42, 171-177 (2022).

Corrected Patent Owner's Response to Office Action, dated May 10, 2013, from File History of Inter Partes Reexamination U.S. Appl. No. 95/002,110.

Correspondence from PTAB Deputy Chief Clerk to Counsel re conference call request-Exhibit 3001 in the Patent Trial and Appeal Board, United States Patent and Trademark Office, Petition No. PTAB-IPR2022-00431.

Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).

Deardorff, Dana et al., Ultrasound Applicators with Internal Cooling for Interstitial Thermal Therapy, SPIE vol. 3594, 36-46, Jan. 1999.

Decision of the Patent Trial and Appeal Board in U.S. Appl. No. 14/731,347.

Declaration of Chris Daft dated Jan. 11, 2022, in the Patent Trial and Appeal Board, United States Patent and Trademark Office, Petition No. PTAB-IPR2022-00431.

Second Declaration of Chris Daft. Dated Jan. 10, 2023, in the Patent Trial and Appeal Board, United States Patent and Trademark Office, Petition No. PTAB-IPR2022-00431.

Declaration of Dr. Daniel van der Weide, dated Oct. 26, 2022, in the Patent Trial and Appeal Board, United States Patent and Trademark Office, Petition No. PTAB-IPR2022-00431.

Declaration of Dr. Dieter Haemmerich, dated Aug. 29, 2012, in the Patent Trial and Appeal Board, United States Patent and Trademark Office, In re U.S. Pat No. 7,717,948.

Declaration of Dr. John M. Moriarty in German Nullity proceedings for EP2261905 dated Jul. 13, 2022.

Declaration of Dr. John Moriarty, dated Jan. 19, 2023, in the Patent Trial and Appeal Board, United States Patent and Trademark Office, Petition No. PTAB-IPR2022-00431.

Declaration of Jonathan Bradford in Support of Patent Owner's Response, dated Oct. 27, 2022.

Declaration of Jonathan Bradford dated May 10, 2022, in the Patent Trial and Appeal Board, United States Patent and Trademark Office, Petition No. PTAB-IPR2022-00431.

Declaration of Dr. Michael Bohm dated Sep. 29, 2022 on behalf of Medtronic Inc.

Declaration of Dr. Robert Tucker, dated Oct. 27, 2022, in the Patent Trial and Appeal Board, United States Patent and Trademark Office, Petition No. PTAB-IPR2022-00431.

Declaration of Farrell Mendelsohn dated Jan. 10, 2022, in the Patent Trial and Appeal Board, United States Patent and Trademark Office, Petition No. PTAB-IPR2022-00431.

Defendant's Reply to Court Order of Oct. 4, 2022 and Plaintiff's Surrejoinder of Sep. 29, 2022 in the Mannheim District Court, case No. 7 O 14/21, dated Oct. 31, 2022.

Defendant's Response dated May 11, 2022 in the Munich Federal Patent Court, Nullity Suit 6 Ni 32/22.

Dibona, Gerald F., "Neural Control of the Kidney, Past, Present and Future," 41 [Part II] Hypertension 621 24 (2003).

Dibona, Gerald, Sympathetic Nervous System and Kidney in Hypertension, Current Opinion in Nephrology and Hypertension, vol. 11, 197-200 (2002).

(56) References Cited

OTHER PUBLICATIONS

Dibona, Gerald F. et al., "Neural Control of Renal Function", 77 Physiological Reviews No. 1, 75 (1997).

Diederich, et al., "Catheter-based Ultrasound Applicators for Selective Thermal Ablation: progress towards MRI-guided applications in prostate," International Journal of Hyperthermia, 20:7, 739-756.

Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.

Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.

Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_doi:10.1109fTBME.2002.807323.

Draney, Mary et al., Three-Dimensional Analysis of Renal Artery Bending Motion During Respiration, International Society of Endovascular Specialists, vol. 12, 380-386 (2005).

Erikson, Kenneth et al., Ultrasound in Medicine: A Review, IEEE Transactions on Sonics and Ultrasonics, vol. 21, No. 3 (1974).

EP Board of Appeals Communication dated Dec. 17, 2019—Preliminary Remarks for EP appeal No. T2680/16-3.3.4.01.

European Search Report in Application No. 12180431.4 dated Jan. 17, 2013.

European Communication in Application No. 12180431.4 dated Oct. 23, 2013.

European Office Action in Application No. 12180431.4.

European Patent No. 12167931, Claims of the Main Request dated Sep. 30, 2016.

European Search Report (Supplementary) in Application No. 14775754.6 dated Feb. 17, 2016.

European Search Report in Application No. 218186547 dated Nov. 19, 2018.

European Search Report in Application No. 20202272.9 dated Mar. 1, 2021.

Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.

Fengler, Karl et al., A Three-Arm Randomized Trial of Different Renal Denervation Devices and Techniques in Patients with Resistant Hypertension (Radiosound-HTN), 139 Circulation 590 (2019).

Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).

Gervais, Debra A. et al., Radiofrequency ablation of renal cell carcinoma: Part 2, Lessons learned with ablation of 100 tumors, 185 AJR Am. J. Roentgenol. 72 (2005).

Goldberg, S. Nahum et al., EUS-guided radiofrequency ablation in the pancreas: results in a porcine model, 50 Gastrointest. Endosc. 392 (1999).

Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).

Gorsich, W., et al., Heat-Induced Contraction of Blood Vessels, Lasers in Surgery and Medicine, 2:1-13 (1982).

Gray, Henry, Gray's Anatomy: The Anatomical Basis of Medicine and Surgery, Churchill Livingstone, New York, NY (1995).

Habict, Antje et al., Sympathetic Overactivity and Kidneys, The Middle European Journal of Medicine, vol. 115, 634-640 (2003).

Hansen et al., The Transplanted Human Kidney Does Not Achieve Functional Reinnervation, 87 Clinical Science 13 (1994).

Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.

He, D. S. et al., Application of Ultrasound Energy for Intracardiac Ablation of Arrhythmias, European Heart Journal, vol. 16, 961-966 (1995).

Heffner, H. et al., "Gain, Band Width, and Noise Characteristics of the Variable-Parameter Amplifier," Journal of Applied Physics, vol. 29, No. 9, Sep. 1 958, 1 1 pages.

Holmes, David R. et al., Pulmonary vein stenosis complicating ablation for atrial fibrillation: clinical spectrum and interventional considerations, 2 JACC Cardiovasc. Interv. 267 (2009).

Hsu, Thomas H. S. et al., Radiofrequency ablation of the kidney: acute and chronic histology in porcine model, 56 Urology 872 (2000).

Huang, S.K.S. and Wilbur, D. EDS, Radiofrequency Catheter Ablation of Cardiac Arrhythmias, Basic Concepts and Clinical Applications, Futura Publishing Company, Inc., Armonk, New York (2000).

Huang, et al., Renal Denervation Prevents and Reverses Hyperinsulinemia-Induced Hypertension in Rats, Hypertension 32 (1998) pp. 249-254.

Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.

Isles et al., Management of Renovascular Disease: A Review of Renal Artery Stenting in Ten Studies, QJM 92, 159-67 (1999).

Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.

Janssen, B. J. A., et al. "Renal nerves in hypertension." Miner Electrolyte Metab., 15:74-82 (1989).

Janzen, Nicolette et al., Minimally Invasive Ablative Approaches in the Treatment of Renal Cell Carcinoma, Current Urology Reports, vol. 3 (2002).

Kaltenbach, Benjamin et al., Renal Artery Stenosis After Renal Sympathetic Denervation, Journal of the American College of Cardiology, vol. 60, No. 25 (2012).

Kapural, Leonardo, et al., "Radiofrequency Ablation for Chronic Pain Control," Anesthetic Techniques in Pain Management, pp. 517-525, 2001.

Katholi, R.E., et al., Importance of Renal Sympathetic Tone in the Development of DOCA-Salt Hypertension in The Rat, Hypertension, 2:266-273 (1980).

Kim, Yun-Hyeon et al., Pulmonary vein diameter, cross-sectional area, and shape: CT analysis, Radiology Society of North America, vol. 235, No. 1, 49-50 (2005).

Kirsh, Danielle, Balloon Catheters: What are some key design considerations?, MassDevice (Dec. 6, 2016).

Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).

Koomans, Hein et al., Sympathetic Hyperactivity in Chronic Renal Failure: A wake-up call, Frontiers in Nephrology, vol. 15, 524-537 (2004).

Kuo, et al., "Atrial Fibrillation: New Horizons", Chang Gung Med J vol. 26 No. Oct. 10, 2003.

Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).

Lee, Jong Deok et al., MR imaging-histopathologic correlation of radiofrequency thermal ablation lesion in a rabbit liver model: observation during acute and chronic stages, 2 Korean J. Radiol. 151 (2001).

Levin, S., et al., ARDIAN: Succeeding Where Drugs Fail-Treating Hypertension in the Cath Lab, In Vivo, 27:23 (2009).

(56) References Cited

OTHER PUBLICATIONS

Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).

Marine, Joseph E., Catheter ablation therapy for supraventricular arrhythmias, 298 JAMA 2768 (2007).

Martin, Louis G. et al., Long-term Results of Angioplasty in 110 Patients with Renal Artery Stenosis, Journal of Vascular and Interventional Radiology, vol. 3, No. 4, 619-626 (1992).

Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.

Matsumoto, Edward D. et al., Short-term efficacy of temperature-based radiofrequency ablation of small renal tumors, 65 Urology 877 (2005).

Medtronic Press Release, Medtronic Announces U.S. Renal Denervation Pivotal Trial Fails to Meet Primary Efficacy Endpoint While Meeting Primary Safety Endpoint (Jan. 9, 2014).

Medtronic Inc., Renal Denervation (RDN): Novel Catheter-Based Treatment for Hypertension, Scientific Background, 2011.

Medtronic Scientific Background, Hypertension and the Symplicity Renal Denervation System.

Medtronic, Symplicity RDN Common System Q&A.

Medtronic Inc., The Symplicity RDN System, 2012.

Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).

Millard, et al., Renal Embolization for Ablation of Function In Renal Failure And Hypertension, Postgraduate Med. J. 65, 729-734 (1989).

Mitchell, et al., "The Renal Nerves" British Journal of Urology, Read by invitation at the Sixth Annual Meeting of the British Association of Urological Surgeons on Jun. 30, 1950.

Morrissey, D. M. "Sympathectomy in the treatment of hypertension." Lancet, CCLXIV:403-408 (1953).

Nair et al., "The Need for and the Challenges of Measuring Renal Sympathetic Nerve Activity," Heart Rhythm 2016; 13:1166-1171.

Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).

Netter, Frank, Atlas of Human Anatomy, Icon Learning Systems, Rochester, NY (2002).

Neumann, Jutta, Sympathetic hyperactivity in chronic kidney disease: Pathogenesis, clinical relevance, and treatment, International Society of Nephrology, vol. 65, 1568-1576 (2004).

News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.

Notice of Deposition of Tucker, filed Dec. 30, 2022 in the Patent Trial and Appeal Board, United States Patent and Trademark Office, Petition No. PTAB-IPR2022-00431.

Notice of Deposition of van der Weide, filed Dec. 30, 2022 in the Patent Trial and Appeal Board, United States Patent and Trademark Office, Petition No. PTAB-IPR2022-00431.

Notice re filing date accorded, dated Feb. 10, 2022 in the Patent Trial and Appeal Board, United States Patent and Trademark Office, Petition No. PTAB-IPR2022-00431.

Nozawa, T., et al. "Effects of long-term renal sympathetic denervation on heart failure after myocardial infarction in rats." Heart Vessels, 16:51-56 (2002).

Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").

Olsson, R et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 Vol. 1 doi:10.1109/JSSC.2005.858479.

Order: Conduct of the Proceeding Scheduling Order 37 C.F.R. sec. 42.5, dated Aug. 8, 2022 in the Patent Trial and Appeal Board, United States Patent and Trademark Office, Petition No. Ptab-IPR2022-00431.

Order Setting Oral Hearing 37 C.F.R. § 42.70, dated Mar. 24, 2023 in the Patent Trial and Appeal Board, United States Patent and Trademark Office, Petition No. PTAB-IPR2022-00431.

Osborn, J., "Catheter-Based Renal Nerve Ablation as a Novel Hypertension Therapy, Lost, and Then Found," in Translation.

Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).

Page, Irvine H. & George J. Heuer, The Effect of Renal Denervation on Patients Suffering from Nephritis, 14 J. Clinical Investigation 443 (1935) (received for publication in 1935).

Papademetriou, Vasilios et al., Renal Sympathetic Denervation for the Treatment of Difficult-to- Control or Resistant Hypertension, 2011 Int. J. Hypertension, Article 196518 (2011).

Papademetriou, et al., "Renal Sympathetic Denervation: Hibernation or Resurrection?", Cardiology 2016; 135, 11 pgs.

Papadopoulos, N., "Evaluation of a Small Flat Rectangular Therapeutic Ultrasonic Transducer Intended for Intravascular Use," Ultrasonics 74, 196-203, 2017.

Pappone C, et al., "Circumferential radiofrequency ablation of pulmonary vein ostia: a new anatomic approach for curing atrial fibrillation", Circulation. 2000; 102(21): 2619-2628. (2000).

Patent Owner's Amended Objections to Evidence Under 37 C.F.R. §42.64.

Patent Owner's Mandatory Notice, filed Feb. 3, 2022 in the Patent Trial and Appeal Board, United States Patent and Trademark Office, Petition No. PTAB-IPR2022-00431.

Patent Owner's Notice of Deposition of Dr. Chris Daft, filed Sep. 20, 2022 in the Patent Trial and Appeal Board, United States Patent and Trademark Office, Petition No. PTAB-IPR2022-00431.

Patent Owner's Notice of Deposition of Dr. Chris Daft filed Feb. 21, 2023 in the Patent Trial and Appeal Board, United States Patent and Trademark Office, Petition No. PTAB-IPR2022-00431.

Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.

Patent Owner's Notice of Deposition of Dr. John Moriarty, filed Feb. 21, 2023 in the Patent Trial and Appeal Board, United States Patent and Trademark Office, Petition No. PTAB-IPR2022-00431.

Patent Owner's Objections to Evidence, filed Aug. 18, 2022 in the Patent Trial and Appeal Board, United States Patent and Trademark Office, Petition No. PTAB-IPR2022-00431.

Patent Owner's Power of Attorney, filed Feb. 3, 2022 in the Patent Trial and Appeal Board, United States Patent and Trademark Office, Petition No. PTAB-IPR2022-00431.

Patent Owner Medtronic Ireland Power of Attorney, filed May 10, 2022 in the Patent Trial and Appeal Board, United States Patent and Trademark Office, Petition No. PTAB-IPR2022-00431.

Patent Owner's Preliminary Response, filed May 10, 2022 in the Patent Trial and Appeal Board, United States Patent and Trademark Office, Petition No. PTAB-IPR2022-00431.

Patent Owner's Request for Oral Hearing, filed Mar. 23, 2023 in the Patent Trial and Appeal Board, United States Patent and Trademark Office, Petition No. PTAB-IPR2022-00431.

Patent Owner's Response, filed Oct. 27, 2022 in the Patent Trial and Appeal Board, United States Patent and Trademark Office, Petition No. PTAB-IPR2022-00431.

Patent Owner's Sur-Reply, filed Mar. 9, 2023 in the Patent Trial and Appeal Board, United States Patent and Trademark Office, Petition No. PTAB-IPR2022-00431.

(56)                    References Cited

OTHER PUBLICATIONS

Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. Ptab- IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prakash, Punit, et al., "Considerations for Theoretical Modeling of Thermal Ablation with Catheter- Based Ultrasonic Sources: Implications for Treatment Planning, Monitoring and Control," International Journal of Hyperthermia, 28:1, 69-86.
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Purerfellner, Helmut et al., Incidence, Management and Outcome in Significant Pulmonary Vein Stenosis Complicating Ablation for Atrial Fibrillation, 93 Am. J. Cardiol. 1428 (2004).
Purerfellner, Helmut & MARTINEK, Martin, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications," Biological Procedures Online, Jan. 2006, 25 pages.
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Romanes, G.J., Cunningham's Textbook of Anatomy (11th ed. 1972).
Ryan, Steve, What are the Risks Associated with a Pulmonary Vein Ablation Procedure?, Atrial Fibrillation: Resources for Patients (last accessed Oct. 18, 2022).

Ryan, Thomas et al., Proceedings of Thermal Treatment of Tissue with Image Guidance, Progress in Biomedical Optics, vol. 3594 (1999).
Ryan, Thomas P., Thermal Treatment of Tissue with Image Guidance; Ultrasound Catheters For Circumferential Cardiac Ablation 1999;.
Sakakura, Kenichi et al., Anatomic Assessment of Sympathetic Peri-Arterial Renal Nerves in Man, Journal of the American College of Cardiology, vol. 64, No. 7, 635-643 (2014).
Salmanpour, A., L. J. Brown and J. K. Shoemaker, "Detection of Single Action Potential in Multi- Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.
Sanchez-Quintana, Damian et al., How close are the phrenic nerves to cardiac structures? Implications for cardiac interventionalists, 16 J. Cardiovasc. Electrophysiol 309 (2005) ("Sánchez- Quintana").
Sato, Yu, et al., "Translational Value of Preclinical Models for Renal Denervation: a histological comparison of human versus porcine renal nerve anatomy," EuroIntervention, 18, e1120-e1128, 2023.
Schlaich, M.P et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.
Schmieder, Ronald E., Renal denervation in patients with chronic kidney disease: current evidence and future perspectives, Nephrol. Dial. Transplant. gfac189 (2022).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Schmidt, Boris, et al., "Pulmonary Vein Isolation by High Intensity Focused Ultrasound," Indian Pacing and Electrophysiology Journal, pp. 126-133 (2006).
Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Shimizu, Kazumasa et al., Sympathetic Dysfunction in Heart Failure, Bailliere's Clinical Endocrinology and Metabolism, vol. 7, No., 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Smithwick, R. H., et al., "Splanchnicectomy for essential hypertension." J. Am. Med. Assoc., 152:1501-1504 (1953).
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D et al., A Survey of Stent Designs, Min Invas Ther & Allied Technol 2002: 11(4) 137- 147 (2002).
Swartz, John F et al., Radiofrequency Endocardial Catheter Ablation of Accessory Atrioventricular Pathway Atrial Insertion Sites, 87 Circulation 487 (1993).
Tank, J et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07. 012.

(56)         References Cited

OTHER PUBLICATIONS

Tanaka, Kazushi et al., "A New Radiofrequency Thermal Balloon Catheter for Pulmonary Vein Isolation," Journal of the American College of Cardiology vol. 38, No. 7, 2001.

Teigen et al., Segmental Renal Artery Embolization for Treatment of Pediatric Renovascular Hypertension, J. Vasco Interv. Radiol. 3, 111-7 (1992).

Thatipelli, Mallik R., et al., CT angiography of renal artery anatomy for evaluating embolic protection devices, 18 J. Vasc. Interv. Radiol. 842 (2007).

The Doctors and Experts at WebMD, Webster's New World Medical Dictionary (3rd ed. 2008) ("WebsterMD").

Transcript of the Mar. 2, 2023 deposition of Dr. John Moriarty.

Transcript of the Mar. 3, 2023 deposition of Dr. Chris Daft.

Transcript of deposition of the Jan. 1, 2023 deposition of Dr. Robert Tucker.

Transcript of the Jan. 14, 2023 deposition of Dr. Daniel van der Weide.

Transcript of the Sep. 30, 2022 deposition of Dr. Chris Daft.

Transcript of the Oct. 1, 2022 deposition of Dr. Farrell Mendelsohn.

Tsao, Hsuan-Ming et al., Evaluation of Pulmonary Vein Stenosis after Catheter Ablation of Atrial Fibrillation, 6 Card. Electrophysiol. Rev. 397 (2002).

Turner, et al., "Initial Experience Using the Palmaz Corinthian Stent for Right Ventricular Outflow Obstruction in Infants and Small Children", Catheterization and Cardiovascular Interventions 51:444-449 (2000).

Uchida, et al., "Effect of radiofrequency catheter ablation on para-sympathetic denervation: A comparison of three different ablation sites." PACE, 21 :2517- 2521 (1998).

Ulmsten, Ulf et al., "The Safety and Efficacy of MenoTreatTM, a new balloon device for thermal endometrial ablation," Acta Obstet Gynecol Scand 2001; 80: 52-57.

Vaezy, Shahram et al., Image-Guided Acoustic Therapy, Annual Review Biomedical Engineering, vol. 3, 375-390 (2001).

Valente, John F et al., Laparoscopic renal denervation for intractable ADPKD-related pain, 16 Nephrol. Dial. Transplant. 160 (2001).

Vujaskovic, Z et al., (1994) Effects of intraoperative hyperthermia on canine sciatic nerve: histopathologic and morphometric studies, International Journal of Hyperthermia, 10:6, 845-855 (1994) ("Vujaskovic 1994").

Wanchoo, Nishey, Medtronic Gets European and Australian Approval for Symplicity Spyral Multi- Electrode Renal Denervation Catheter, Medgadget (2013).

Weinstock, Marta et al., "Renal Denervation Prevents Sodium Retention and Hypertension in Salt- Sensitive Rabbits with Genetic Baroreflex Impairment", 90 Clinical Science 287 (1996).

Xu, J et al., "A Bidirectional Neuromodulation Technology for Nerve Recording and Stimulation, Micromachines," vol. 9, 1 1 538. Oct. 23, 2018. doi:10.3390/mi9110538.

Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.

Zazgornik, "Bilateral Nephrectomy: The best, but often overlooked, treatment for refractory hypertension in hemodialysis patients," Am. J. Hypertension, 11:1364-1370 (1998).

Ziegler et al., Sources of Urinary Catecholamines in Renal Denervated Transplant Recipients, 8 J. Hypertension No. 10, 927 (1990).

U.S. Appl. No. 17/453,636, filed Nov. 4, 2021, File History.

U.S. Appl. No. 10/408,665, File History.

U.S. Appl. No. 60/624,793, File History.

U.S. Appl. No. 60/370,190, File History.

U.S. Appl. No. 60/415,575, File History.

U.S. Appl. No. 60/442,970, File History.

U.S. Appl. No. 60/616,254, File History.

U.S. Provisional Application Serial No. 60/747, 137, File History.

U.S. Appl. No. 60/808,306, File History.

U.S. Appl. No. 60/816,999, File History.

U.S. Appl. No. 61/405,472, File History.

U.S. Appl. No. 11/532,814, Non-Final Office Action mailed Mar. 29, 2012.

U.S. Appl. No. 14/683,966, Non-Final Office Action mailed Jun. 12, 17, 14 pgs.

U.S. Appl. No. 14/683,966,Jun. 12, 17, 13 pgs.

U.S. Appl. No. 14/683,966, Notice of Allowance mailed Jan. 31, 18, 8 pgs.

U.S. Appl. No. 14/683,966, PTO Response to Rule 312 Communication mailed Mar. 29, 18, 2 pgs.

U.S. Appl. No. 14/683,966, 312 Amendment filed Mar. 13, 18, 10 pgs.

U.S. Appl. No. 14/683,966, Corrected Notice of Allowance mailed May 22, 18, 4 pgs.

U.S. Appl. No. 15/204,349, Preliminary Amendment filed Nov. 30, 16, 3 pgs.

U.S. Appl. No. 15/204,349, Restriction Requirement mailed May 17, 18, 7 pgs.

U.S. Appl. No. 15/204,349, Response filed Jun. 5, 18 to Restriction Requirement mailed May 17, 18, 7 pgs.

U.S. Appl. No. 15/204,349, Non-Final Office Action mailed Nov. 27, 18, 14 pgs.

U.S. Appl. No. 15/204,349, Response filed Feb. 27, 19 to Non-Final Office Action mailed Nov. 27, 18, 10 pgs.

U.S. Appl. No. 15/204,349, Final Office Action mailed Apr. 22, 19, 16 pgs.

U.S. Appl. No. 15/204,349, Response filed Jun. 24, 19 to Final Office Action mailed Apr. 22, 19, 12 pgs.

U.S. Appl. No. 15/204,349, Advisory Action mailed Jul. 9, 19, 5 pgs.

U.S. Appl. No. 15/261,732, Notice of Allowance dated Sep. 25, 2018.

U.S. Appl. No. 15/299,694, Restriction Requirement mailed Aug. 6, 18, 6 pgs.

U.S. Appl. No. 15/299,694,Aug. 6, 18, 7 pgs.

U.S. Appl. No. 15/299,694, Non-Final Office Action mailed Nov. 27, 18, 15 pgs.

U.S. Appl. No. 15/299,694, Response filed Feb. 27, 19 to Non-Final Office Action mailed Nov. 27, 18, 10 pgs.

U.S. Appl. No. 15/299,694, Final Office Action mailed Apr. 22, 19, 16 pgs.

U.S. Appl. No. 15/299,694, Response filed Jun. 24, 19 to Final Office Action mailed Apr. 22, 19, 11 pgs.

U.S. Appl. No. 15/299,694, Advisory Action mailed Jul. 9, 19, 5 pgs.

U.S. Appl. No. 15/943,354, Preliminary Amendment filed Apr. 3, 18, 9 pgs.

U.S. Appl. No. 15/943,354, Restriction Requirement mailed Nov. 20, 19, 8 pages.

U.S. Appl. No. 15/943,354,Nov. 20, 19, 8 pages.

U.S. Appl. No. 15/943,354,.

U.S. Appl. No. 15/996,978, Preliminary Amendment filed Jun. 5, 18, 11 pgs.

U.S. Appl. No. 15/996,978, Restriction Requirement mailed Feb. 7, 20, 7 pages.

U.S. Appl. No. 15/996,978,Feb. 7, 20, 8 pages.

U.S. Appl. No. 15/996,978, Restriction Requirement mailed Apr. 16, 20, 8 pages.

U.S. Appl. No. 15/996,978,Apr. 16, 20, 8 pgs.

U.S. Appl. No. 15/996,978, Non-Final Office Action mailed Jun. 11, 20, 8 pages.

U.S. Appl. No. 16/219,874,.

U.S. Appl. No. 16/517,180, Preliminary Amendment filed Jul. 19, 19, 12 pgs.

U.S. Patent Application No. 01003US1].

File History of U.S. Appl. No. 12/754,337.

File History to U.S. Pat. No. 9,943,666.

File History to U.S. Pat. No. 9,981, 108.

File History to U.S. Pat. No. 10,039,901.

Final Office Action dated Feb. 19, 2021, U.S. Appl. No. 15/996,978, filed Jun. 4, 2018.

Final Office Action dated Jun. 16, 2021, U.S. Appl. No. 15/996,978, filed Jun. 4, 2018.

(56)           References Cited

OTHER PUBLICATIONS

Non-Final Office Action dated Sep. 2, 2021, U.S. Appl. No. 15/996,978, filed Jun. 4, 2018.

Notice of Allowance dated Oct. 6, 2021, U.S. Appl. No. 15/996,978, filed Jun. 4, 2018.

Response to Office Action dated May 18, 2021, U.S. Appl. No. 15/996,978, filed Jun. 4, 2018.

Response to Office Action dated Jul. 20, 2021, U.S. Appl. No. 15/996,978, filed Jun. 4, 2018

Response to Office Action dated Sep. 22, 2021, U.S. Appl. No. 15/996,978, filed Jun. 4, 2018.

Ahmed, Muneeb et al., "Thermal Ablation Therapy for Hepatocellular Carcinoma," J. Vasc. Interv. Radiol., vol. 13, No. 9 pt. 2, 2002.

Benito, Fernando et al., "Radiofrequency catheter ablation of accessory pathways in infants," Heart, vol. 78, p. 160-162, 1997.

Chang, Isaac A et al., "Thermal Modeling of Lesion Growth with Radiofrequency Ablation Devices," Biomedical Engineering Online vol. 3, p. 27, 2004.

Chung, Andrew et al., "Thermal dosimetry of a focused ultrasound beam in vivo by magnetic resonance imaging," Medical Physics, vol. 26, No. 9, p. 2017-2026, Sep. 1999.

Damianou, Christakis et al., "High Intensity Focused Ultrasound Ablation of Kidney Guided MRI," Ultrasound in Med. & Biol., vol. 30, No. 3, p. 397-404, 2004.

Deardorff, Dana L et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170 -178, Jan. 2000.

Dewhirst, M.W et al., "Basic Principles of Thermal Dosimetry and Thermal Thresholds for Tissue Damage from Hyperthermia," International Journal of Hyperthermia vol. 19, No. 3, p. 267-294, May-Jun. 2003.

Diederich, Chris J et al., "Ultrasound Technology for Hyperthermia," Ultrasound in Med. & Biol., vol. 25, No. 6, p. 871-887, 1999.

Fry, F.J et al., "Production of Reversible Changes in the Central Nervous System by Ultrasound," Science, vol. 127, p. 83-84, Jan. 1958.

Gavrilov, L.R et al., The Effect of Focused Ultrasound on the Skin and Deep Nerve Structures of Man and Animal, p. 279-292.

Gavrilov, L.R., "Use of Focused Ultrasound for Stimulation of Nerve Structures," Ultrasonics, p. 132-138, May 1984.

Graham, S.J et al., "Quantifying Tissue Damage Due to Focused Ultrasound Heating Observed by MRI" Magnetic Resonance in Medicine vol. 41, p. 321-328, 1999.

Goldberg, S. Nahum et al., "Radiofrequency Tissue Ablation: Increased Lesion Diameter with a Perfusion Electrode," Acad. Radiol. Vol. 3, No. 8, p. 636-644, Aug. 1996.

Hacker, Axel et al., "Extracorporeal Organotripsy for Renal Tumours," Current Opinion in Urology, vol. 13, p. 221-225, 2003.

Hausberg, Martin et al., "Sympathetic Nerve Activity in End-Stage Renal Disease," Circulation, vol. 106, p. 1974-1979, 2002.

Ho, Siew Yen et al., "Anatomy of the Left Atrium: Implications for Radiofrequency Ablation of Atrial Fibrillation," J Cardiovasc Electrophysiol, vol. 10, p. 1525-1533, Nov. 1999.

Israel, Gary M et al., "MRI of the Kidney and Urinary Tract," Journal of Magnetic Resonance Imaging, vol. 24, p. 725-734, 2006.

Jiang, S.C et al., "Effects of Thermal Properties and Geometrical Dimensions on Skin Burn Injuries," Burns, vol. 28, p. 713-717, 2002.

Kaye, David M et al., "Functional and Neurochemical Evidence for Partial Cardiac Sympathetic Reinnervation After Cardiac Transplantation in Humans," Circulation, vol. 88, No. 3, Sep. 1993.

Keane, David, "New Catheter Ablation Techniques for the Treatment of Cardiac Arrhythmias," Cardiac Electrophysiology Review vol. 6, No. 4, p. 341-348, 2002.

Kennedy, J.E et al., "High Intensity Focused Ultrasound: Surgery of the Future?", The British Journal of Radiology, vol. 76, p. 590-599, Sep. 2003.

Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.

Lauder, Lucas et al., "Renal Denervation in the Management of Hypertension," EuroIntervention, vol. 20, pg. e467-e478, 2024.

Lele, p. P., "Effects of Focused Ultrasonic Radiation on Peripheral Nerve, with Observations on Local Heating," Experimental Neurology, vol. 8, p. 47-83, 1963.

Liao, Qingyao et al., "Optimal Strategy for HIFU-Based Renal Sympathetic Denervation in Canines," Frontiers in Cardiovascular Medicine vol. 8, p. 1-11, Oct. 2021.

Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.

Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.

Mahfoud, Felix et al., "Device Therapy of Hypertension," Circulation Research nol. 128, p. 1080- 1099, Apr. 2021.

Makin, Inder Raj. S et al., "Miniaturized Ultrasound Arrays for Interstitial Ablation and Imaging," Ultrasound in Med. & Biol. Vol. 31, No. 11, p. 1539-1550, 2005.

Malcolm, A.L et al., "Ablation of Tissue vols. Using High Intensity Focused Ultrasound" Ultrasound in Med. & Biol. Vol. 22 no. 5 p. 659-669, 1996.

Manolis, Antonis S et al., "Radiofrequency Catheter Ablation for Cardiac Tachyarrhythmias," Annals of Internal Medicine, vol. 131, No. 6, p. 452-461, Sep. 1994.

Mitchell, G.A.G et al., "An Anatomical Evaluation of Operations for Hypertension," Proceedings of the Anatomical Society vol. LIV., No. 10, p. 545-560.

Mompeo, Blanca et al., "The Gross Anatomy of the Renal Sympathetic Nerves Revisited," Clinical Anatomy vol. 29, p. 660-664, Apr. 2016.

Moore, J.H et al., "The Biophysical Effects of Ultrasound on Median Nerve Distal Latencies," Electromyogr. Clin. Neurophysiol., vol. 40, p. 169-190, 2000.

Nath, Sunil et al., "Basic Aspects of Radiofrequency Catheter Ablation," Journal of Cardiovascular Electrophysiology vol. 5, No. 10, p. 863-876, Oct. 1994.

Nath, Sunil et al., "Biophysics and Pathology of Catheter Energy Delivery Systems," Progress in Cardiovascular Diseases, vol. XXXVII, No. 4, p. 185-204, January/Feb. 1995.

Nau, William H et al., "MRI-Guided Interstitial Ultrasound Thermal Therapy of the Prostate: A Feasibility Study in the Canine Model," Medical Physics vol. 32, No. 3, p. 733-743, Mar. 2005.

Nikfarjam, Mehrdad et al., "Mechanisms of Focal Heat Destruction of Liver Tumors," Journal of Surgical Research, vol. 127, No. 2, p. 208-223, Aug. 2005.

Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.

Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.

Papademetriou, Vasilios et al., "Renal Nerve Ablation for Resistant Hypertension, How Did We Get Here, Present Status, and Future Directions," Circulation, No. 129, p. 1440-1451, 2014.

Pozzoli, Alberto et al., "Electrophysiological Efficacy of Epicor High-Intensity Focused Ultrasound," European Journal of Cardio-Thoracic surgery, vol. 42, p. 129-134, 2012.

Riis, Thomas et al., "Effective Ultrasonic Stimulation in Human Peripheral Nervous System," IEE Transactions on Biomedical Engineering, vol. XX, No. XX, p. 1-8, XXXX 2021.

Roux, N et al., "The Myocardial Sleeves of the Pulmonary Veins: Potential Implications for Atrial Fibrillation," Surg. Radiol. Anat., vol. 26, p. 285-289, Feb. 2004.

Schuarte, Patrick et al., "Catheter Ablation of Cardiac Autonomic Nerves for Prevention of Vagal Atrial Fibrillation," Circulation vol. 102, p. 2774-2780, 2000.

(56) References Cited

OTHER PUBLICATIONS

Tellez, Armando et al., "Renal Artery Nerve Distribution and Density in the Porcine Model: Biologic Implications for the Development of Radiofrequency Ablation Therapies," Translational Research vol. 162 no.6, p. 381-389, Dec. 2013.

Ter Haar, G., "Ultrasound Focal Beam Surgery," Ultrasound in Med. & Biol., vol. 21, No. 9, p. 1089- 1100, 1995.

Ter Haar, G.R et al., "Ultrasonic Heating of Mammalian Tissues In vivo," Br. J. Cancer vol. 45, Supp. V., p. 65-67, 1982.

Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.

Trippodo, Nick C et al., "Similarities of Genetic (Spontaneous) Hypertension," Circulation Research vol. 48, No. 3, p. 309-319, Mar. 1981.

Urban, Bruce A et al., "Three-dimensional vol. rendered CT Angiography of the Renal Arteries and Veins: Normal Anatomy, Variants, and Clinical Applications," RG vol. 21 no. 2, p. 373-386, March-Apr. 2001.

Wang, Shyh-Hau et al., "Effects of Low Intensity Ultrasound on the Conduction Property of Neural Tissues," IEEE International Ultra-sonics, Ferroelectrics, and Frequency Control Joint 50th Anniversary Conference, p. 1824-1827, 2004.

Weld, Kyle J et al., "Comparison of Cryoablation, Radiofrequency Ablation and High-Intensity Focused Ultrasound for Treating Small Renal Tumours" BJU International vol. 96, p. 1224-1229, 2005.

Wells, p. N.T., "Functional Modification: Clinical Applications," Biomedical Ultrasonics, p. 470-504, 1977.

Winternitz, Sherry R et al., "Importance of the Renal Nerves in the Pathogenesis of Experimental Hypertension," Hypertension (supp. III), vol. 4, No. 5, pg. III-08- III-115, September-Oct. 1982.

Wulff, V.J et al., "Effects of Ultrasonic Vibrations on Nerve Tissues," p. S.E.B.M., vol. 76, p. 361- 366, 1951.

Yarmolenko, Pavel S et al., "Thresholds for thermal damage to normal tissues: An update," Int. J. Hyperthermia, vol. 27 no.4, p. 320-343, Jun. 2011.

Young, Robert R et al., "Functional Effects of Focused Ultrasound on Mammalian Nerves," Science, vol. 134, p. 1521-1522, Nov. 1961.

Zimmer, J.E et al., "The Feasibility of Using Ultrasound for Cardiac Ablation," IEEE Transactions on Biomedical Engineering, vol. 42, No. 9, p. 891-897, Sep. 1995.

* cited by examiner

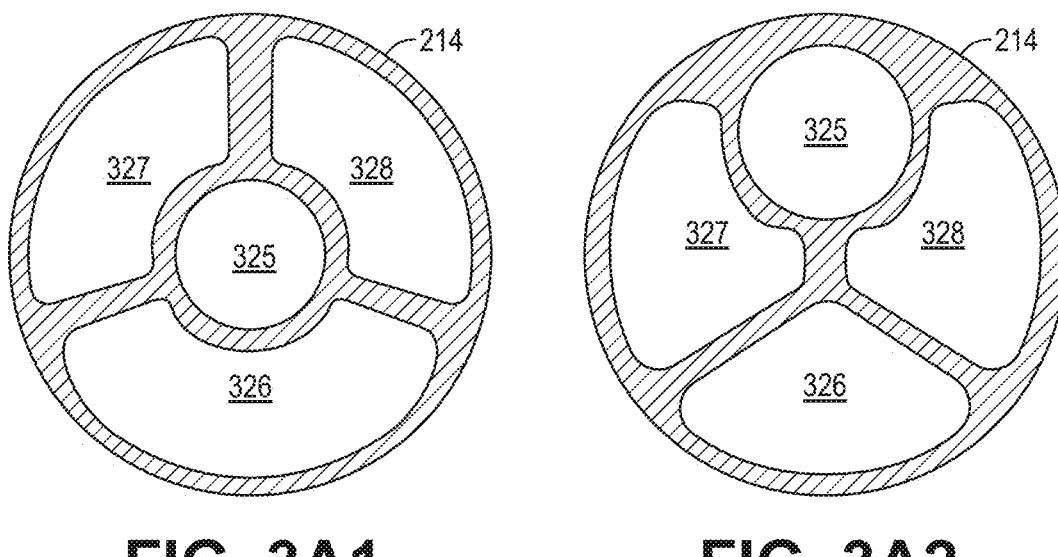
FIG. 3A1          FIG. 3A2
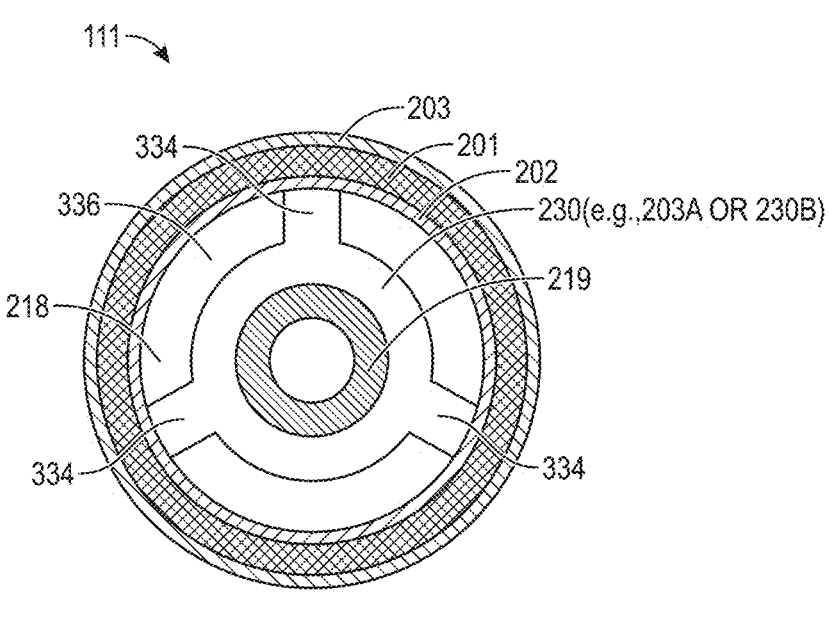
FIG. 3B

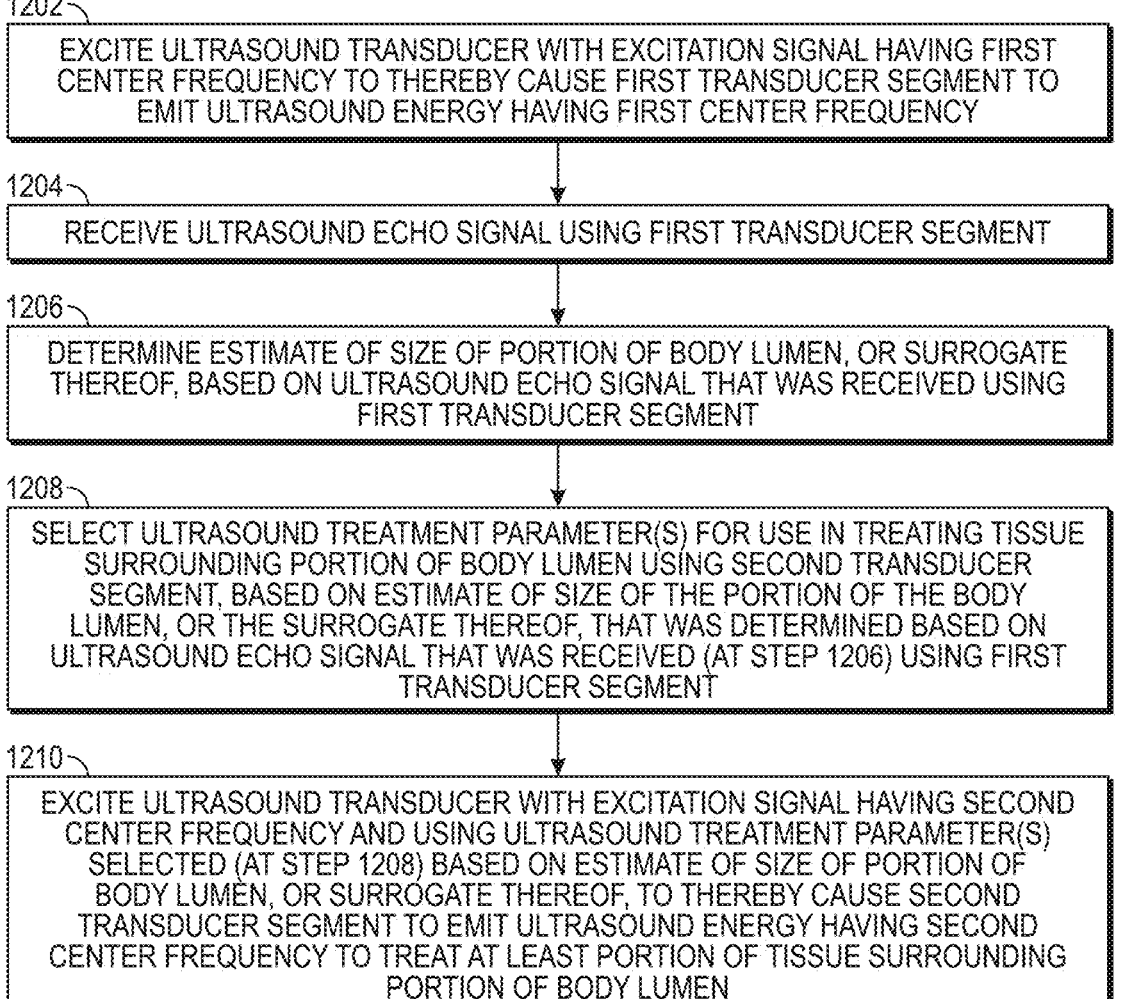

1202 —
EXCITE ULTRASOUND TRANSDUCER WITH EXCITATION SIGNAL HAVING FIRST CENTER FREQUENCY TO THEREBY CAUSE FIRST TRANSDUCER SEGMENT TO EMIT ULTRASOUND ENERGY HAVING FIRST CENTER FREQUENCY

1204 —
RECEIVE ULTRASOUND ECHO SIGNAL USING FIRST TRANSDUCER SEGMENT

1206 —
DETERMINE ESTIMATE OF SIZE OF PORTION OF BODY LUMEN, OR SURROGATE THEREOF, BASED ON ULTRASOUND ECHO SIGNAL THAT WAS RECEIVED USING FIRST TRANSDUCER SEGMENT

1208 —
SELECT ULTRASOUND TREATMENT PARAMETER(S) FOR USE IN TREATING TISSUE SURROUNDING PORTION OF BODY LUMEN USING SECOND TRANSDUCER SEGMENT, BASED ON ESTIMATE OF SIZE OF THE PORTION OF THE BODY LUMEN, OR THE SURROGATE THEREOF, THAT WAS DETERMINED BASED ON ULTRASOUND ECHO SIGNAL THAT WAS RECEIVED (AT STEP 1206) USING FIRST TRANSDUCER SEGMENT

1210 —
EXCITE ULTRASOUND TRANSDUCER WITH EXCITATION SIGNAL HAVING SECOND CENTER FREQUENCY AND USING ULTRASOUND TREATMENT PARAMETER(S) SELECTED (AT STEP 1208) BASED ON ESTIMATE OF SIZE OF PORTION OF BODY LUMEN, OR SURROGATE THEREOF, TO THEREBY CAUSE SECOND TRANSDUCER SEGMENT TO EMIT ULTRASOUND ENERGY HAVING SECOND CENTER FREQUENCY TO TREAT AT LEAST PORTION OF TISSUE SURROUNDING PORTION OF BODY LUMEN

FIG. 12

1902 ─╮
CIRCULATE COOLING FLUID THROUGH A BALLOON PRIOR TO INSERTING THE BALLOON INTO THE BODY LUMEN

1904 ─╮
DETECT A FLUID PARAMETER OF THE COOLING FLUID PRIOR TO INSERTING THE BALLOON INTO THE BODY LUMEN

1906 ─╮
GENERATE A REFERENCE CURVE BASED ON THE DETECTED FLUID PARAMETER PRIOR TO INSERTING THE BALLOON INTO THE BODY LUMEN (A)

METHODS AND SYSTEMS FOR DETERMINING BODY LUMEN SIZE

This application claims the benefit of priority under 35 U.S.C. § 119(e) to U.S. Provisional Application No. 63/223, 517, filed Jul. 19, 2021, titled ONE-SIZE-FITS-ALL RENAL ARTERY TREATMENT SYSTEM, U.S. Provisional Application No. 63/223,519, filed Jul. 19, 2021, titled METHODS AND SYSTEMS FOR DETERMINING BODY LUMEN SIZE, and U.S. Provisional Application No. 63/367,119 filed Jun. 27, 2022, titled CATHETER HAVING COMPLIANT BALLOON all of which are incorporated herein by reference in their entireties to provide continuity of disclosure.

BACKGROUND

Field

This application relates generally to minimally-invasive apparatuses, the systems and methods that provide energy delivery to a targeted anatomical location of a subject, and more specifically, to catheter-based, intraluminal apparatuses for the treatment of tissue, such as nerve tissue.

Background Information

According to the Centers for Disease Control and Prevention (CDC), about one in every three adults suffer from high blood pressure, also known as hypertension. Left untreated, hypertension can result in renal disease, arrhythmias and heart failure. In recent years, the treatment of hypertension has focused on minimally invasive interventional approaches to inactivate the renal nerves surrounding the renal artery. Autonomic nerves tend to follow blood vessels to the organs that they enervate. Catheters may reach specific structure that may be proximate to the lumens in which they travel. For example, one system employs a radio frequency (RF) generator connected to a catheter having multiple electrodes placed against the intima of the renal artery and used to create an electrical field in the vessel wall and surrounding tissue that results in resistive (ohmic) heating of the tissue to a temperature sufficient to ablate the tissue and the renal nerve passing through that tissue. To treat all the renal nerves surrounding the renal arteries, the RF electrodes are repositioned several times around the inside of the renal artery. However, the relatively confined electric fields created by the RF electrodes may miss some of the renal nerves, leading to an incomplete treatment. Additionally, to heat the renal nerves, the RF electrodes must contact the intima, posing a risk of damage or necrosis to the intima, which in turn can lead to thrombus formation, fibrosis of the vessel wall, mechanical weakening of the vessel and possible vessel dissection.

Another approach to renal nerve deactivation is the use of high-intensity focused ultrasound (HIFU), which relies on vibrational energy to cause frictional heating and disruption of the tissue, and in turn, raise the tissue temperature sufficiently to cause ablation or remodeling.

U.S. Pat. Nos. 9,943,666, 9,981,108, and 10,039,901 to Warnking, U.S. Pat. Nos. 9,700,372, 9,707,034, and 10,368, 944 to Schaer, and U.S. Pat. Nos. 10,350,440 and 10,456, 605 to Taylor, the entire contents of each of which is incorporated by reference herein, disclose a system that uses unfocused ultrasound to ablate nerves. Embodiments of the system include an ultrasound transducer positioned along a distal end of a catheter designed to be inserted into a blood vessel (e.g., the renal artery). Electrical cabling, which is received within a cabling lumen of the catheter, can be used to power the ultrasound transducer. The ultrasound transducer emits one or more therapeutic doses of unfocused ultrasound energy, which heats the tissue adjacent to the body lumen within which the transducer is disposed. The system may also include a balloon mounted at the distal end of the catheter used to circulate cooling fluid both prior to, during, and after activation of the transducer to cool the transducer and help prevent thermal damage to the interior surface of the blood vessel wall while the nerves are being heated and damaged at depth.

Such a design enables creation of one or more ablation zones sufficient to achieve long-term nerve inactivation at different locations around the circumference of the blood vessel, thereby treating a patient's hypertension while mitigating damage to the blood vessel and surrounding organs.

The ultrasound transducer may include first and second electrodes which are arranged on either side of a cylindrical piezoelectric material, such as lead zirconate titanate (PZT). To energize the transducer, a voltage is applied across the first and the second electrodes at frequencies selected to cause the piezoelectric material to resonate, thereby generating vibration energy that is emitted radially outward from the transducer. The transducer is designed to provide a generally uniform and predictable emission profile For various reasons, it is important to know the inner diameter (size) of a body lumen (e.g., a renal artery, a hepatic artery, or a pulmonary artery) into which an ultrasound transducer and/or balloon is inserted, or is to be inserted. For example, an appropriate dose of neuromodulation, e.g., ultrasound and/or RF energy, may be selected and used for a treatment based on a body lumen size.

SUMMARY

The present invention is defined in the independent claims. Further embodiments of the invention are defined in the dependent claims.

A tissue treatment system is provided herein. The tissue treatment system comprises a catheter comprising a balloon mounted on a catheter shaft, one or more syringes to fill the balloon with fluid and a non-transitory computer readable memory storing instructions. The system also comprises one or more processors configured to execute the stored instructions to cause the tissue treatment system to fill the balloon with fluid within a body lumen and detect a fluid parameter of the fluid over a period of time. The tissue treatment system is also caused to determine a parameter curve of the fluid parameter, wherein the parameter curve includes the fluid parameter versus an independent variable over the period of time. The tissue treatment system is further caused to compare the parameter curve of the fluid parameter to a reference curve, and determine, based on the comparison, a size of the body lumen or a neuromodulation parameter corresponding to the size of the body lumen.

A method is provided herein. The method includes filling a balloon within a body lumen with a fluid. The method includes detecting a fluid parameter of the fluid over a period of time. The method includes determining a parameter curve of the fluid parameter. The parameter curve includes the fluid parameter versus an independent variable over the period of time. The method includes comparing the parameter curve of the fluid parameter to a reference curve. The method includes determining, based on the comparison, a size of the body lumen or a neuromodulation parameter corresponding to the size of the body lumen.

A non-transitory computer readable medium storing instructions is provided herein. The instructions, when executed by one or more processors of the tissue treatment system summarized above, cause the tissue treatment system to perform the method summarized above.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIG. 2A-1 illustrates a side view of selected components of the ultrasound-based tissue treatment system introduced in FIG. 1, in accordance with an embodiment.

FIG. 2A-2 illustrates a side view of selected components of the ultrasound-based tissue treatment system introduced in FIG. 1, in accordance with an embodiment.

FIG. 3A1 illustrates a cross-sectional view of a catheter shaft, along the line A-A in FIG. 2C, in accordance with an embodiment.

FIG. 3A2 illustrates a cross-sectional view of the catheter shaft, along the line A-A in FIG. 2C, in accordance with an embodiment.

FIG. 3B illustrates a cross-sectional view of the ultrasound transducer along the line B-B shown in FIG. 2C, in accordance with an embodiment.

FIG. 12 is a flowchart that is used to summarize a method of the present technology that can be used to determine an estimate a size of a portion of body lumen, or a surrogate thereof, using a transducer inserted therein, in accordance with an embodiment.

DETAILED DESCRIPTION

Figure 1:
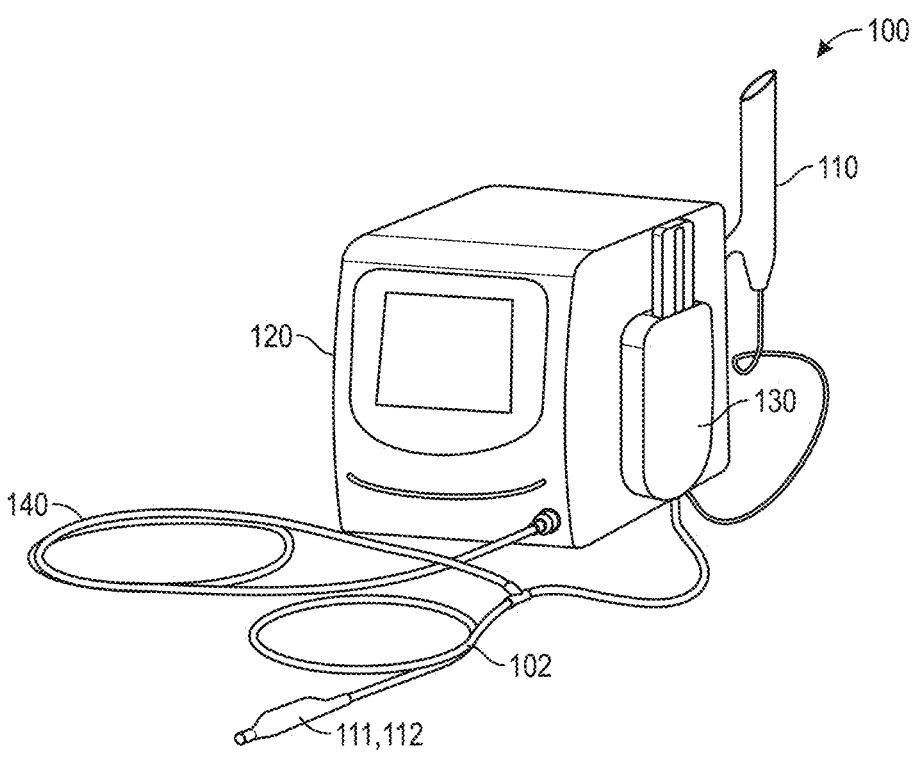
FIG. 1 illustrates selected components of an ultrasound-based tissue treatment system, in accordance with an embodiment.

Existing methods of sizing vessels includes fluoroscopy and/or computed tomography (CT) imaging with contrast agent. However, the use of fluoroscopy and CT imaging with contrast agent has limitations. For example, fluoroscopy can expose patients to radiation. Certain embodiments of the present technology described herein relate to methods that overcome such limitations by using a tissue treatment system to provide a catheter-based method of vessel sizing. More particularly, the use of the tissue treatment system can determine the vessel size directly and accurately, and without exposing the patient to as much radiation as fluoroscopy requires. The tissue treatment system can include a catheter having an ultrasound transducer and a balloon surrounding the ultrasound transducer. The tissue treatment system includes a fluid supply subsystem configured to provide cooling fluid from the fluid supply subsystem to the balloon. The tissue treatment system can both estimate a vessel size and use the estimation to treat the vessel.

Balloon ablation treatment apparatuses, the systems, and portions thereof, and methods of using the same are provided herein. In certain embodiments, acoustic-based tissue treatment transducers, apparatuses, the systems, and portions thereof, are provided. In certain embodiments, the ablation treatment apparatus comprising a balloon having electrodes and/or piezoelectric material attached thereto. Preferably, the systems are catheter-based. The system may be delivered intraluminally (e.g., intravascularly) so as to place a transducer within a target anatomical region of the subject, for example, within a suitable body lumen such as a blood vessel. Once properly positioned within the target anatomical region, the transducer can be activated to deliver unfocused ultrasonic energy radially outward so as to suitably heat, and thus treat, tissue within the target anatomical region. The transducer or piezoelectric material can be activated at a frequency, duration, and energy level suitable for treating the targeted tissue. In one non-limiting example, unfocused ultrasonic energy generated by the transducer or piezoelectric material or radio frequency (RF) energy transmitted by the electrodes may target select nerve tissue of the subject, and may heat such tissue in such a manner as to neuromodulate (e.g., fully or partially ablate, necrose, or stimulate) the nerve tissue. In a manner such as described in the Warnking, Schaer, and Taylor patents mentioned above, neuromodulating renal nerves may be used to treat various conditions, e.g., hypertension, chronic kidney disease, atrial fibrillation, autonomic nervous system for use in treating a variety of medical conditions, arrhythmia, heart failure, end stage renal disease, myocardial infarction, anxiety, contrast nephropathy, diabetes, metabolic disorder and insulin resistance, etc. However, it should be appreciated that the balloon catheters suitably may be used to treat other nerves and conditions, e.g., sympathetic nerves of the hepatic plexus within a hepatic artery responsible for blood glucose levels important to treating diabetes, or any suitable tissue, e.g., heart tissue triggering an abnormal heart rhythm, and is not limited to use in treating (e.g., neuromodulating) renal nerve tissue. In another example, a tissue treatment catheter is used to ablate sympathetic nerves of the renal arteries and a hepatic artery to treat diabetes or other metabolic disorders. In certain embodiments, the tissue treatment catheters are used to treat an autoimmune and/or inflammatory condition, such as rheumatoid arthritis, sepsis, Crohn's disease, ulcerative colitis, and/or gastrointestinal motility disorders by neuromodulating sympathetic nerves within one or more of a splenic artery, celiac trunk, superior or inferior mesenteric artery. In certain embodiments, the tissue treatment catheter is used to ablate nerve fibers in the celiac ganglion and/or renal arteries to treat hypertension. In certain embodiments, the transducers are used to treat pain, such as pain associated with pancreatic cancer, by, e.g., neuromodulating nerves that innervate the pancreas. Ultrasound or RF energy may also be used to ablate nerves of both the pulmonary vein and the renal arteries to treat atrial fibrillation. In still other examples, ultrasound or RF energy may additionally or alternatively be used to ablate nerves innervating a carotid body in order to treat hypertension and/or chronic kidney disease.

In intraluminal systems, ultrasound transducers may be disposed within balloons that are filled with a cooling fluid before and during treatment. Alternatively, an ultrasound transducer may be exposed directly to the bloodstream, without a surrounding balloon, in what may be referred to as balloonless embodiments. In certain balloonless embodiments, blood in the body lumen, e.g., renal artery, is relied upon to cool both the transducer and the artery lumen. In certain balloonless embodiments, the transducer may still be cooled using cooling fluid. For example, cooling fluid may flow through and/or around the body of the ultrasonic transducer without using a balloon, for example by using a hollow region on the outside and/or inside of the transducer for fluid to flow. In certain embodiments, a balloon may surround the transducer, and the balloon may contact the interior surface (e.g., intima) of the body lumen. In certain embodiments, the transducer may be used to output an acoustic signal when the balloon fully occludes a body lumen, and the cooling fluid within the balloon may be used to cool both the body lumen and the transducer. In certain embodiments, the balloon may surround the transducer in order to cool the transducer during sonications, but the balloon may not contact or occlude the body lumen, and the blood within the body lumen may be relied upon to cool the body lumen instead of the cooling fluid.

In certain embodiments, the balloon ablation treatment apparatus comprising a balloon at the distal end of a catheter having electrodes on the external surface of the balloon spaced apart longitudinally along a longitudinal axis and/or radially around a circumference of the distal end of the ablation treatment apparatus. The electrodes may also comprise a spiral pattern, zig-zag pattern, etc. In an embodiment, the electrodes comprise two pairs of two electrodes, wherein each pair of electrodes are located 180 degrees apart from each other along the circumference of the balloon and the other pair of electrodes are also located 180 degrees apart from each other along the circumference of the balloon and are on the opposite side of the balloon. In certain embodiments, the electrodes comprise first and second helical electrodes attached to opposite ends of the balloon around the circumference of the balloon in a spiral manner. The electrodes may be activated as monopolar or bipolar electrodes. In certain embodiments, balloon ablation treatment apparatus comprises a two bipolar electrode pairs disposed on the outer surface of the balloon. Bipolar electrode pairs provide for both a more controlled ablation and a shallower ablation than a monopolar electrode embodiment. The electrodes may be connected to a controller using one or more electrically conductive wires. The controller may be configured to apply power or deliver electrical signals to the electrodes. In an embodiment, the controller generates radiofrequency (RF) signals to the electrodes. The balloon ablation treatment apparatus may comprise one or more lumens, e.g., a guidewire lumen, one or more fluid lumens, and/or a cable lumen.

In certain embodiments, a catheter may be used that comprises an ultrasound balloon catheter that includes both a transducer configured to transmit ultrasound thermal energy and electrodes attached to the balloon configured to deliver RF energy and/or detect nerve signals. The electrodes comprise material and/or a thickness that does not interfere with the sonication.

In certain embodiments, a catheter may be used that comprises piezoelectric material attached to the balloon configured to deliver ultrasound ablative energy.

Overview of System Components and Features

Figures 1, 2A:
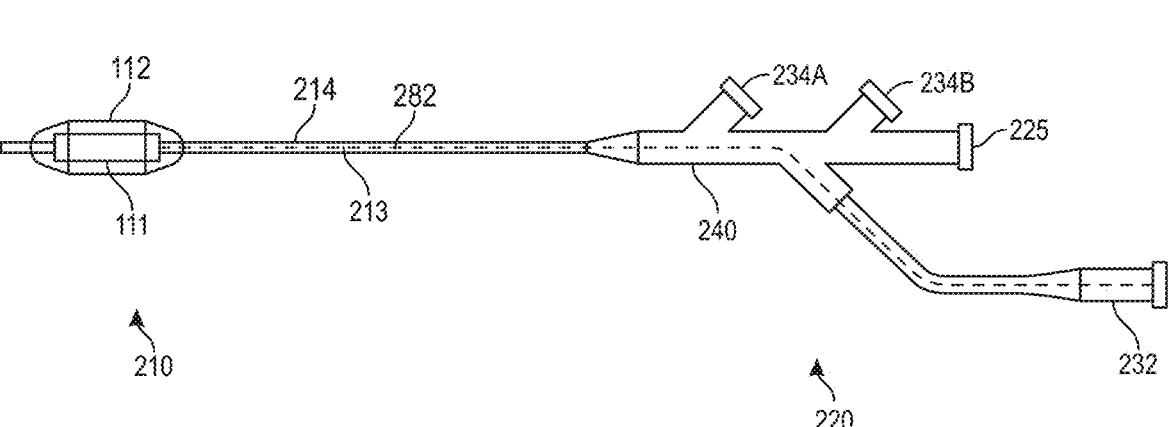
Figures 2, 2A:
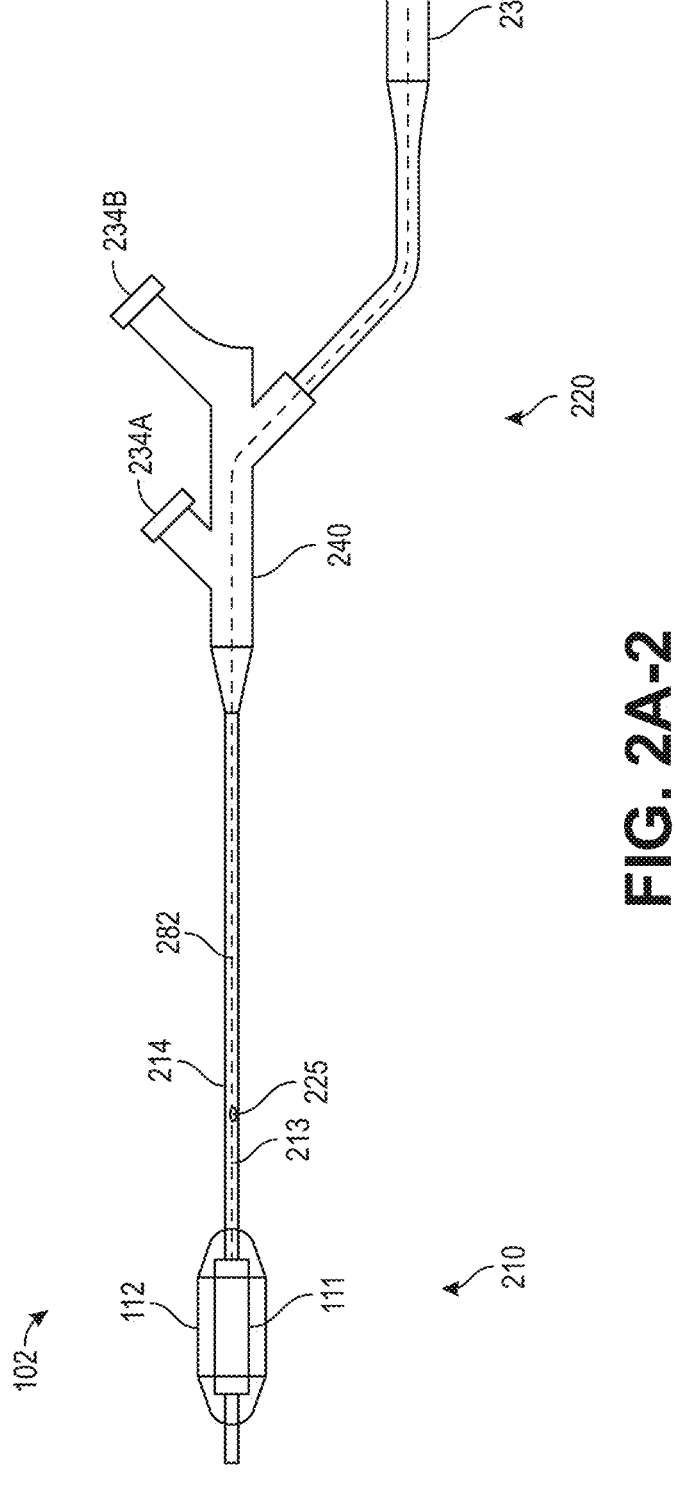
Figure 2B:
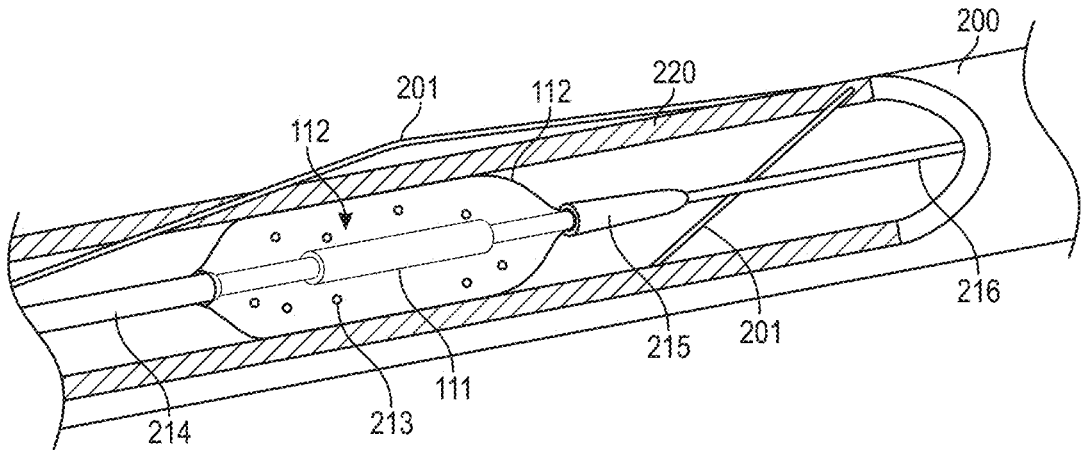
FIG. 2B illustrates a perspective view of additional selected components of the ultrasound-based tissue treatment system inserted into a body lumen, in accordance with an embodiment.

FIGS. 1, 2A, and 2B illustrate features of an ultrasound-based tissue treatment system 100, according to various configurations provided herein. Referring initially to FIG. 1, the system 100 is shown as including a catheter 102, a controller 120, and a connection cable 140. In certain embodiments, the system 100 further includes an ultrasound transducer 111 within a balloon 112, a reservoir 110, a fluid transfer cartridge 130, and a control mechanism, such as a handheld remote control. In certain embodiments, which can be referred to as "balloonless" embodiments, the system 100 does not include the balloon 112. In certain such balloonless embodiments, the system 100 also does not include the reservoir 110 and the cartridge 130. In certain other balloonless embodiments, the system 100 does include the reservoir 110 and/or the cartridge 130.

In the embodiment shown in FIG. 1, the controller 120 is shown as being connected to the catheter 102 through the cartridge 130 and the connection cable 140. In certain embodiments, the controller 120 interfaces with the cartridge 130 to provide a cooling fluid to the catheter 102 for selectively inflating and deflating the balloon 112. The balloon 112 can be made from, e.g., nylon, a polyimide film, a thermoplastic elastomer (such as those marked under the trademark PEBAX™), a medical-grade thermoplastic polyurethane elastomer (such as Pellethane®, Isothane®, or other suitable polymers or any combination thereof), but is not limited thereto.

Referring now to FIG. 2A-1, the tissue treatment catheter 102 can include a distal region 210 and a proximal region 220. The catheter 102 may have a length that depends on a treatment application. For example, in certain embodiments suitable for, e.g., renal denervation through a femoral access delivery method, the catheter 102 can have a working length (measured from a distal tip of the catheter 102 to a proximal hub 240 of the catheter 102) of 80 to 90 cm, e.g., 85 cm, in the femoral access delivery method. In embodiments suitable for, e.g., renal denervation through a radial access delivery method, the catheter 102 can have a working length of a comparatively longer length. More particularly, the working length can be 150 to 160 cm, e.g., 155 cm. Furthermore, an overall length of the catheter 102 for such application, including a length of cabling extending to an electrical coupling 232, can be longer. More particularly, the cabling can have a length of about 305 cm from the proximal hub 240 to the electrical coupling 206.

The catheter 102 can have a profile that is suitable to accessing a renal artery through the femoral and radial access locations. For example, the catheter 102 may be 4 to 6 French in diameter, e.g., 5 French. The profile is facilitated in part by a catheter shaft 214 having an outer diameter in a range of 0.050 to 0.060 inch, e.g., 0.057 inch.

The distal region 210 of the tissue treatment catheter 102 may be a portion of the device that is advanced into a target anatomy, e.g., a target vessel having a vessel wall, to treat the target vessel. The distal region 210 can include the balloon 112 mounted on a catheter shaft 214. The catheter shaft 214 can be an elongated tubular structure that extends longitudinally from a proximal end to a distal end. The balloon 112 can be mounted and supported on the catheter shaft 214 at the distal end. Furthermore, the ultrasound transducer 111 can be mounted on the catheter shaft 214 and contained within the balloon 112. Accordingly, the catheter shaft 214 can facilitate delivery of a cooling fluid to the balloon 112 and delivery of electrical energy to the transducer 111.

The catheter shaft 214 can include one or more lumens (FIGS. 3A-1 to 3B) that may be used as fluid conduits, electrical cabling passageways, guidewire lumens, and/or the like. In an embodiment, for example, the catheter shaft 214 can include a guidewire lumen 213 that is shaped, sized and otherwise configured to receive a guidewire. In an embodiment, the guidewire lumen 213 is an over-the-wire type guidewire lumen, extending from a distal tip of the catheter 102 through an entire length of the catheter shaft 214 to an exit port 225 in the proximal hub 240 of the catheter 102. As described below, the lumen(s) of the catheter shaft 214 may also communicate inflation/cooling fluid from the proximal region 220 to the balloon 112 during balloon expansion.

In an embodiment, a transducer 111 is mounted on the catheter shaft 214 at the distal region 210, within an interior of the balloon 112. The transducer 111 can be an ultrasound transducer used to emit energy toward the vessel wall. For example, the transducer 111 can emit ultrasound energy circumferentially, e.g., 360 degrees, around the vessel wall. In an embodiment, electric cabling 282 extends from the proximal region 220 to the distal region 210, and is connected to the transducer 111 to generate energy for emission to target tissue.

The ultrasound transducer 111 may include first and second electrodes that are arranged on either side of a cylindrical piezoelectric material, such as lead zirconate titanate (PZT). To energize the transducer 111, a voltage is applied across the first and the second electrodes at frequencies selected to cause the piezoelectric material to resonate, thereby generating vibration energy that is emitted radially outward from the transducer 111. The transducer 111 is designed to provide a generally uniform and predictable emission profile, to inhibit damage to surrounding non-target tissue. In addition, a cooling fluid is circulated through the balloon 112, both prior to, during, and after activation of the transducer 111, so as to reduce heating of an inner lining of the body lumen and to cool the transducer 111. In this manner, the peak temperatures achieved by tissue within the cooling zone remain lower than for tissue located outside the cooling zone.

The proximal region 220 may include one or more connectors or couplings. The connectors or couplings can be electrically connected to the transducer 111 via the electric cabling 282. For example, the proximal region 220 may include one or more electrical coupling 232 that connects to a proximal end of the electric cabling 282. A distal end of the electric cabling 282 can be connected to the transducer 111.

The catheter 102 may be coupled to the controller 120 by connecting the electrical coupling 232 to the connection cable 140. The connection cable 140 may be removably connected to the controller 120 and/or the catheter 102 via a port on the controller 120 and/or the catheter 102. Accordingly, the controller 120 can be used with several catheters 102 during a procedure by disconnecting the coupling of a first catheter, exchanging the first catheter with a second catheter, and connecting a coupling of the second catheter to the controller 120. In certain embodiments, e.g., where only one catheter needs to be used during a procedure, the connection cable 140 may be permanently connected to the controller 120.

In certain embodiments, the proximal region 220 of the catheter 102 may further include one or more fluidic ports. For example, the proximal hub 240 can include a fluidic inlet port 234A and a fluidic outlet port 234B, via which an expandable member, e.g., the balloon 112, may be fluidly coupled to the reservoir 110 (FIG. 1). The reservoir 110 can therefore supply cooling fluid to the balloon 112 through the fluidic ports. The reservoir 110 optionally may be included with the controller 120, e.g., attached to the outer housing of the controller 120 as shown in FIG. 1. Alternatively, the reservoir 110 may be provided separately.

Referring now to FIG. 2A-2, a side view of selected components of the ultrasound-based tissue treatment system introduced in FIG. 1, in accordance with an embodiment. In an embodiment, the catheter 102 can have a rapid-exchange type guidewire lumen 213. More particularly, the guidewire lumen 213 can extend from the distal tip of the catheter 102 through a partial length of the catheter shaft 214 to an exit port 225 in the distal portion 210 of the catheter 102. For example, a distance from the distal tip to the rapid exchange port may be in a range of 20 to 30 cm, e.g., 23 cm. The proximal hub 240 illustrated in FIG. 2B may differ from the proximal hub 240 illustrated in FIG. 2A, given that the exit port 250 may be moved from the proximal portion 220 to the distal portion 210. Other components of rapid exchange version of the catheter 102 may be similar to those of the over-the-wire version of the catheter 102, and thus, the descriptions of the components illustrated in FIG. 2A can apply to similarly numbered components illustrated in FIG. 2B.

FIG. 2B illustrates a perspective view of selected components of the catheter 102, e.g., components of the distal portion 210 as may be inserted into a body lumen of a subject. In FIG. 2B, the body lumen is a blood vessel (e.g., a renal artery) that has a plurality of nerves 201 in an outer layer (e.g., adventitia layer) of the blood vessel. As illustrated in FIG. 2B, the distal portion 210 may include the ultrasound transducer 111, the balloon 112 filled with a cooling fluid 213, the catheter shaft 214, and/or a guidewire support tip 215 configured to receive a guidewire 216.

The transducer 111 may be disposed partially or completely within the balloon 112, which may be inflated with a cooling fluid 213 so as to contact the interior surface (e.g., intima) of the body lumen. In certain embodiments, the transducer 111 may be used to output an acoustic signal when the balloon 112 fully occludes a body lumen of a target vessel 200. The balloon 112 may center the transducer 111 within the body lumen. In certain embodiments, e.g., suitable for renal denervation, the balloon 112 is inflated while inserted in the body lumen of the patient during a procedure at a working pressure of about 10 to about 30 psi using the cooling fluid 213. The balloon 112 may be or include a compliant, semi-compliant or non-compliant medical balloon. The balloon 112 is sized for insertion in the body lumen and, in the case of insertion into the renal artery, for example, the balloon 112 may be selected from available sizes including outer diameters of 3.5, 4.2, 5, 6, 7, or 8 mm, but not limited thereto. In some embodiments, balloon 112 is a compliant balloon configured to inflate between a first inflation diameter, e.g., 3.5 mm, and a second inflation diameter, e.g., 8 mm, using an inflation pressure between a first inflation pressure, e.g., 10 psi, and a second inflation pressure, e.g., 30 psi, such that the outer diameter is directly correlated with the pressure of the balloon 112. In some embodiments, the balloon 112 is a compliant balloon configured to inflate to a first inflation diameter, e.g., 3.5 mm, a second inflation diameter, e.g., 8 mm, using a constant inflation pressure, e.g., 10 psi. In some embodiments, balloon 112 may have a nominal outer diameter, e.g., 4 mm, and when the balloon 112 is used in a body lumen less than or equal to that nominal diameter of the balloon 112, e.g., a renal artery that is less than and up to 4 mm in diameter, the balloon 112 is inflated to a first inflation pressure, e.g., 10 psi. When the balloon 112 is used in a body lumen larger than the nominal size of the balloon 112, e.g., a renal artery that is more than 4 mm in diameter, the balloon 112 is inflated using a second inflation pressure, e.g., 30 psi, to increase the size of the balloon, such that the balloon is in apposition with the body lumen. In other embodiments, two compliant balloons may be used to cover a range of lumen sizes. For example, a balloon that ranges between 3 to 5 mm using an inflation pressure between 10 psi and 30 psi and a second balloon that ranges between 4 to 8 mm using an inflation pressure between 10 psi and 30 psi may be used in order to cover the typical range of the renal artery, which is between 3 and 8 mm in diameter. One of skill in the art will understand that the particular inflation pressures and balloon diameters would be adjusted depending on the particular body lumen(s) BL(s) of interest. In certain embodiments, a balloon 112 may have different compliance curves (the inflation diameter as a function of pressure may shift) depending on the number of sonications that the balloon has been through. As depicted below in FIG. 18, the inflation diameters may predictably become larger at the same balloon pressures as the balloon goes through sonications.

In some embodiments, as shown in FIG. 2B, when inflated by being filled with the cooling fluid 213 under the control of the controller 120, the outer wall of the balloon 112 may be generally parallel with the outer surface of the transducer 111. Optionally, the balloon 112 may be inflated sufficiently as to be in apposition with the body lumen. For example, when inflated, the balloon 112 may at least partially contact, and thus be in apposition with, an inner surface of a vessel wall 220 of the body lumen. When the balloon 112 is in apposition with the body lumen, and more specifically the interior circumferential wall of the body lumen, the balloon 112 can substantially stop blood within the body lumen from following past the balloon.

In other configurations, the balloon 112 is configured not to contact the body lumen when expanded. The balloon 112 may surround the transducer in order to cool the transducer during sonications, but the balloon may not contact or occlude the body lumen, and the blood within the body lumen may be relied upon to cool the body lumen instead of the cooling fluid. In addition, instead of relying on the balloon 112 to center the transducer, in certain embodiments, one or more flexible baskets that expand proximal and distal of the transducer 111 may be used to center the transducer 111. In an alternative embodiment, at least one balloon that expands proximal and distal of the transducer 111 may be used to center the transducer 111. In another embodiment, a basket that surround the transducer 111 and balloon 112 may be used to center the transducer, which basket is preferably made of a material that does not interfere with the sonication.

To reduce a likelihood of interfering with sonication, a basket can have a structure such that the basket material is outside of an acoustic window of the transducer 111. For example, the basket, rather than being concentric with the transducer 111, can be asymmetrically disposed relative to the transducer 111. In an embodiment, a gap is disposed between the transducer and a target ablation region, and the basket is not positioned within the gap. Accordingly, ablation energy directed to the target ablation region by the transducer 111 may pass through the gap without encountering the basket.

In certain embodiments, wherein the balloon 112 surrounds the transducer, but the balloon does not contact or occlude the body lumen, the balloon 112 is non-compliant. In certain embodiments, the balloon 112 comprises nylon. The catheter may use a single size non-compliant balloon/ sheath coupled with centering mechanisms located proximal and distal to the balloon to center the device within the vessel such that native flow of the blood is not obstructed. The cooling of the artery wall is provided by the native blood flow while cooling and the isolation of the transducer from the blood stream is provided within the balloon. In an embodiment, the non-compliant balloon of a fixed diameter that is less than or equal to the minimum vessel size to be treated, e.g., a 3.5 mm balloon may be used for an artery that is at least 3.5 mm in diameter. For vessels greater than the non-compliant balloon size, centering mechanisms can be provided such that the ultrasound treatment zone and blood flow within the vessel is unobstructed. This mechanism prevents vessel overstretching at the treatment site during ablation. The cooling can be provided to the vessel wall by the native blood flow that exists within the vessel during treatment.

For a blood vessel that matches the balloon diameter, the non-compliant balloon (e.g., 112) can act as the centering mechanism. The cooling of the vessel wall can be managed by a cooling system of the generator by flowing water or other cooling fluid, such as dextrose or saline, through the balloon if necessary. A non-compliant balloon advantageously offers tighter control of balloon design. The non-compliant balloon (e.g., 112) may be advantageously constructed such that the balloon surface, which is without wrinkles when under inflation, does not interfere with sonication, and holds the desired shape. Additionally, or alternatively, the balloon 112 may be maintained at a specified size by pushing cooling fluid into and pulling cooling fluid out of the balloon 112 at a specified flow rate. In balloonless embodiments, the transducer 111 is not disposed within a balloon.

Figure 2C:
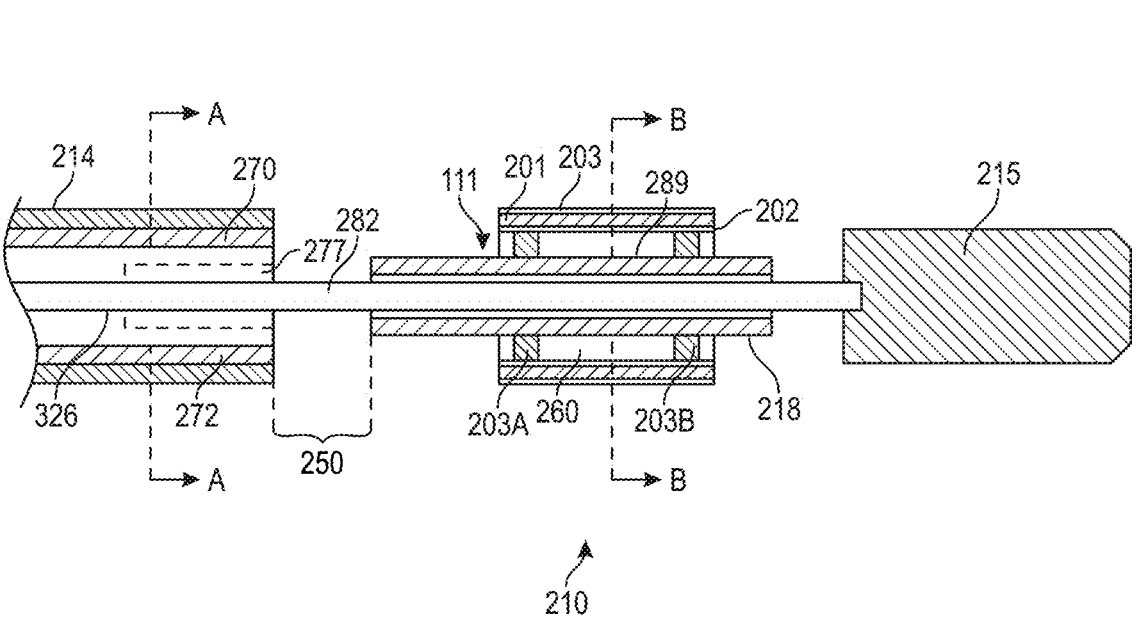
FIG. 2C illustrates a longitudinal cross-sectional view of a distal portion of a catheter of the ultrasound-based tissue treatment system, in accordance with an embodiment.

FIG. 2C illustrates a longitudinal cross-sectional view of the distal portion 210 of the catheter 102. FIG. 3A1 illustrates a cross-sectional view of the catheter shaft 214 along the line A-A shown in FIG. 2C, according to an embodiment. FIG. 3A2 illustrates a cross-sectional view of the catheter shaft 214 along the line A-A shown in FIG. 2C, according to an alternative embodiment. FIG. 3B illustrates a cross-sectional view of the ultrasound transducer 111 along the line B-B shown in FIG. 2C, according to an embodiment. In certain embodiments, the catheter shaft 214 may be about 1.8 mm in diameter. The catheter shaft 214 includes one or more lumens that may be used as fluid conduits, an electrical cabling passageway, a guidewire lumen and/or the like, as described in further detail below with reference to FIGS. 3A1 and 3A2. In certain embodiments suitable, e.g., for renal denervation, the guidewire 216 has a diameter of about 0.36 mm and a length of from about 180 cm to about 300 cm, and is delivered using a 7 French guide catheter, having a minimum inner diameter of 2.06 mm and a length less than about 80 cm. In certain embodiments, a 6 French guide catheter is used to deliver the guidewire 216. In certain embodiments, the guide catheter has a length of about 55 cm. In certain embodiments, the guide catheter has a length of about 85 cm and a hemostatic valve is attached to the hub of the guide catheter to allow for continuous irrigation of the guide catheter to decrease the risk of thromboembolism.

Referring again to FIG. 2C, the ultrasound transducer 111 may include a cylindrical hollow tube made of a piezoelectric material (e.g., lead zirconate titanate (PZT), etc.), with inner and outer electrodes 202, 203 disposed on the inner and outer surfaces of the cylindrical tube, respectively. Such a cylindrical hollow tube of piezoelectric material is an example of, and thus can be referred to as, a piezoelectric transducer body 201. The piezoelectric transducer body 201 can have various other shapes and need not be hollow. In certain embodiments suitable, e.g., for renal denervation, the piezoelectric material, of which the piezoelectric transducer body 201 is made, is lead zirconate titanate 8 (PZT8), which is also known as Navy III Piezo Material. Raw PZT transducers may be plated with layers of copper, nickel and/or gold to create electrodes on surfaces (e.g., the inner and outer surfaces) of the piezoelectric transducer body (e.g., 201). Application of a voltage and alternating current across inner and outer electrodes 202, 203 causes the piezoelectric material to vibrate transverse to the longitudinal direction of the cylindrical tube 201 and radially emit ultrasonic waves. While the ultrasound transducer 111 in FIG. 2C is not shown as being surrounded by a balloon, it is noted that the ultrasound transducer 111 can be positioned within a balloon (e.g., 112), e.g., as shown in FIG. 2A.

As shown in FIG. 2C, the ultrasound transducer 111 can be generally supported via a backing member or post 218. In certain embodiments, the backing member 218 comprises stainless steel coated with nickel and gold, wherein nickel is used as a bonding material between the stainless steel and gold plating. In certain embodiments suitable, e.g., for renal denervation, an outer diameter of the transducer 111 is about 1.5 mm, an inner diameter of the transducer 111 is about 1 mm, and the transducer 111 has a length of about 6 mm. Transducers having other inner diameters, outer diameters, and lengths, and more generally dimensions and shapes, are also within the scope of the embodiments described herein. Further, it is noted that the drawings in the FIGS. are not necessarily drawn to scale, and often are not drawn to scale.

As illustrated in FIG. 2C, the backing member 218 may extend from the distal portion 210 of the catheter shaft 214 to a distal tip 215. For example, the distal end of the backing member 218 may be positioned within an adjacent opening in the tip 215, and the proximal end of the backing member 218 may be moveably coupled to the distal portion 210 of the catheter shaft 214 via the electrical cabling 282. In other embodiments, there is a gap 250 between the distal end of the catheter shaft 214 and the proximal end of the ultrasound transducer 111. Additional details of the electrical cabling 282, and how the electrical cabling may be electrically coupled to the transducer 111, are described below.

In order to permit liquid cooling along both the inner and outer electrodes 202, 203, the backing member 218 may include one or more stand-off assemblies 230a and 230b. The stand-off assemblies 230a, 230b may define one or more annular openings through which cooling fluid 213 may enter the space of the transducer 111 (which may be selectively insulated) between the backing member 218 and the inner electrode 202. Accordingly, the backing member 218 may serve as a fluid barrier between the cooling fluid 213 circulated within the balloon 112 and the lumen of the backing member 218 that receives the guidewire 216. As shown schematically in FIG. 2C, for example, the stand-off assemblies 230a, 230b of the backing member 218 may be positioned along or adjacent to each longitudinal end of the ultrasound transducer 111 (separated by a main post body 289) and couple the cylindrical tube 201 of the ultrasound transducer 111 to the backing member 218. With reference to FIG. 3B, a stand-off assembly 230 (230a or 230b) may have a plurality of lugs, ribs, or attachment points that engage the inner electrode 202 of the transducer 111. In certain embodiments, the attachment points are soldered to the inner electrode 202 of the transducer 111. The number, dimensions, and placement of the ribs may vary, as desired or required. For example, as illustrated in FIG. 3B, a total of three ribs can be generally equally-spaced apart from one another at an angle of 120 degrees apart from one another, defining openings through which a cooling fluid or blood may enter an interior space 260 of the cylindrical tube 201 between the inner electrode 202 disposed along the inner surface of the cylindrical tube 201 and the backing member 218. In certain embodiments, the maximum outer diameter of stand-off assemblies 230a and 230b is about 1 mm, the outer diameter of the main post body 289 is about 0.76 mm, and the inner diameter of backing member 218 is about 0.56 mm.

In accordance with certain embodiments, the stand-off assemblies 230a, 230b are electrically conductive, so as to electrically couple the inner electrode 202 of the ultrasound transducer 111 to the backing member 218. One or more conductors of the electrical cabling 282 may be electrically coupled to the backing member 218. Thus, as the controller 120 is activated, current may be delivered from the electrical cabling 282 to the inner electrode 202 of the ultrasound transducer 111 via the backing member 218 and the stand-off assemblies 230a, 230b, which advantageously eliminates the need to couple the cabling 282 directly to the inner electrode 202 of the transducer 111. In other embodiments, the backing member 218 and the stand-off assemblies 230a, 230b are made of one or more electrical insulator material(s), or if made of an electrically conductive material(s) are coated with one or more electrical insulator material(s). In certain embodiments, one or more electrical conductors of the cabling 282 are directly coupled (e.g., soldered) to the inner electrode 202 of the transducer 111.

Moreover, as illustrated in FIG. 2C, the backing member 218 may have an isolation tube disposed along its interior surface so as to prevent or reduce the likelihood of electrical conduction between the guidewire 216 (shown in FIG. 2B) and the backing member 218, for use in embodiments where such an electrical conduction is not desired. The isolation tube can be formed of a non-electrically conductive material (e.g., a polymer, such as polyimide), which can also be referred to as an electrical insulator. As illustrated in FIG. 2C, the isolation tube may extend from the catheter shaft 214 through the lumen of the backing member 218 within the transducer 111 to the tip 215. In this manner, the transducer 111 is distally offset from the distal end of the catheter shaft 214.

As illustrated in FIGS. 2C, the catheter 102 may also include a bore 277 extending from the distal end of the catheter 102 proximally within the catheter 102, and sized and shaped to receive at least a portion of the backing member 218, thereby electrically insulating the isolation tube and/or the ultrasound transducer 111. Accordingly, during delivery of the catheter 102 to the anatomical region being treated, the backing member 218, the isolation tube, and/or the ultrasound transducer 111 may be at least partially retracted within the bore 277 of the catheter 102, e.g., by retracting the electrical cabling 282, thereby providing sufficient stiffness to the catheter 102 such that the catheter 102 may be delivered in a safe manner.

Figure 2D:
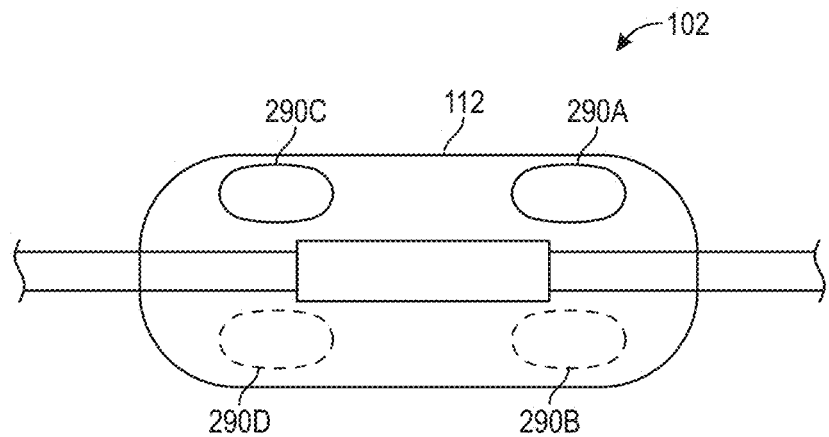
FIG. 2D is a side view of a distal portion of a catheter of a tissue treatment system, in accordance with an embodiment.

In certain embodiments, balloon catheter comprising electrodes may be used to generate RF ablative energy, detect artery size, sense nerves and/or map nerves. Impedance between the electrodes may also be measured in order to aid in measuring the body lumen size. As illustrated in FIG. 2D, the catheter 102 may comprise a plurality of electrodes 290A, B, C, and D, but not a transducer. In certain embodiments, the catheter 102 comprises both electrodes attached to the balloon and a transducer inside the balloon.

The catheter shaft 214 includes one or more lumens that may be used as fluid conduits. For example, the catheter shaft 214 may include fluid lumens for transferring the inflation/cooling fluid, e.g., water, sterile water, saline, 5% dextrose (D5 W), other liquids or gases, etc., from and to a fluid source, e.g., the reservoir 110, at the proximal region 220 of the catheter 102 external to the patient. The catheter shaft 214 can include one or more fluid channels to move fluid into or out of a balloon 112. For example, the fluid channel(s) can include an inlet channel 270 to deliver the inflation fluid from the inlet port 234a to the balloon 112 under control of the controller 120. Similarly, the fluid channel(s) can include an outlet channel 272 to return the inflation fluid from the balloon to the outlet port 234b. Accordingly, the inlet channel 234a and the outlet channel 234b are in fluid communication with the balloon 112 to circulate fluid through the balloon 112 at a flow rate selected to inflate the balloon 112. The flow rate also controls heat transfer between the balloon 112 and the vessel wall 220 to reduce a likelihood of overheating tissue during treatment. For example, the flow rate can provide for active cooling of about the first millimeter of tissue to preserve the integrity of, e.g., the renal arterial wall.

As illustrated in FIGS. 3A1 and 3A2, the catheter shaft 214 includes one or more lumens that can be used as fluid conduits, electrical cabling passageways, guidewire lumens, and/or the like. For example, as illustrated in FIGS. 3A1 and 3A2, the catheter shaft 214 may comprise a guidewire lumen 325 that is shaped, sized and otherwise configured to receive the guidewire 216. In certain embodiments, as illustrated in FIG. 3A1, the guidewire lumen 325 is located in the center of the catheter shaft 214 in order to center the transducer 111 within the catheter shaft 214. Alternatively, the guidewire lumen 325 can be offset from the center of the catheter shaft 214, e.g., as shown in FIG. 3A2. The catheter shaft 214 may also include a cable lumen 326 for receiving electrical cabling 282. Further, the catheter shaft 214 can include one or more fluid lumens 327, 328 for transferring the cooling fluid 213 (e.g., water, sterile water, saline, 5% dextrose (D5 W)), other liquids or gases, etc., from and to a fluid source, e.g., the reservoir 110 and fluid transfer cartridge 130, at the proximal portion 220 of the catheter 102 (external to the patient) to the balloon 112 under control of the controller 120. Active cooling of about the first millimeter of tissue is designed to preserve the integrity of the blood vessel wall, e.g., the renal vessel wall. The guidewire lumen 325 can extend longitudinally through the entire catheter shaft 214, parallel to the fluid lumens 327, 328. Alternatively, the guidewire lumen 325 may extend longitudinally through only a portion of the catheter shaft 214, e.g., where catheter 102 is a rapid exchange (RX) type catheter.

The catheter 102 may include only a single fluid lumen or two or more fluid lumens (e.g., 3, 4, more than 4, etc.), as desired or required. As illustrated in FIG. 3A1, in an embodiment, the fluid lumens 327 and 328 and the cable lumen 326 all have a kidney-shaped or D-shaped cross-sections configured to maximize efficiency of fluid flow delivery and distribute fluid uniformly across the ultrasound transducer 111 by maximizing area, while minimizing the perimeter of the fluid lumens 327 and 328. In certain embodiments, each of the fluid lumens 327 and 328 and the cable lumen 326 are substantially symmetrical, the same size, the same geometry, and/or are interchangeable, e.g., as shown in FIG. 3A1. Changes in fluid flow rate within the catheter can lead to delayed, incomplete, or over treatment. In certain embodiments, the catheter shaft 214 is configured to enable a fluid flow rate of about 40 mL/min. In certain embodiments, the catheter shaft 214 is configured to enable a fluid flow rate of about 35 to 45 mL/min. In certain embodiments, the catheter shaft 214 is configured to enable a fluid flow rate of about 20 to 45 mL/min. In certain embodiments, e.g., suitable for radial delivery during a renal denervation procedure, the catheter shaft 214 is configured to enable a fluid flow rate of about 10 to 20 mL/min. Each of one or more lumens (e.g., 272) may be in fluid communication with the same or separate, individual fluid sources external to the patient at the proximal portion 220 of the catheter 102.

As another example, the catheter shaft 214 may include any suitable number of fluid lumens for transferring the cooling fluid to and from the balloon 112 (or to the transducer 111 in balloonless embodiments) from the reservoir 110 and cartridge 130 responsive to instructions executed by the controller 120. In certain balloonless embodiments, the catheter shaft 214 may omit fluid lumens 327, 328 and the system 100 may omit the reservoir 110 and the cartridge 130. In certain balloonless embodiments, the catheter shaft 214 includes the fluid lumens 327, 328 and the system 100 includes the reservoir 110 and the cartridge 130.

In certain embodiments, as illustrated in FIG. 3A2, the guidewire lumen 325 is located proximal to and/or shares a wall with the catheter shaft 214 so as to enable expedited exchange of the catheters during a procedure. In such embodiments, the cable lumen 326 may be located opposite the guidewire lumen 225 and also share a wall with the catheter shaft 214. The cable lumen 326 may be, e.g., triangular or rectangular in shape, and may be configured to maximize the area available for and minimize the perimeter of the fluid lumens 327 and 328, thereby enabling a higher flow rate for the same pressure. The fluid lumens 327 and 328 may be shaped so as to optimize flow rate and reduce, and preferably minimize, fluidic friction. In such embodiments, the area of fluid lumens 327 and 328 may not be maximized, but instead the walls of the fluid lumens 327 and 328 may be rounded to avoid pockets that may otherwise cause fluidic friction, thereby optimizing flow rate of the cooling fluid 213 within the fluid lumens 327 and 328.

The catheter shaft 214 may include within at least the cable lumen 326, the electrical cabling 282 (e.g., a coaxial cable, parallel coaxial cables, a shielded parallel pair cable, one or more wires, or one or more other electrical conductors) coupling the inner and outer electrodes 202, 203 of the ultrasound transducer 111 to the controller 120, such that the controller 120 may apply a suitable voltage across such electrodes so as to cause the piezoelectric material of the transducer 111 to emit ultrasonic energy to a subject. In certain embodiments, the cable lumen 326 is shaped, sized and otherwise configured to receive the electrical cabling 282 (e.g., coaxial cable(s), wire(s), other electrical conductor(s), etc.). The electrical cabling 282 permits the electrodes 202, 203 of the ultrasound transducer 111 to be selectively activated in order to emit acoustic energy to a subject. More specifically, the electrical cabling 282 can allow for the communication of transducer information, such as operating frequency and power, from the catheter 102 to the controller

120 and/or vice versa, as well as the transfer of electrical energy to the ultrasound transducer 111 during a procedure.

The distal portion 210 of the catheter 102 may be percutaneously delivered to the target anatomical location (e.g., at a specified location within the body lumen) via any suitable intraluminal access route, e.g., via a gastrointestinal route or via an intravascular route such as the femoral or radial route. In certain embodiments, the controller 120 is configured so as to fill the balloon 112 with the cooling fluid 213 only after the distal portion 210 of the catheter 102 is suitably positioned at the target anatomical location. The catheter 102 may be delivered through the body lumen with or without the assistance of a guide sheath and/or a guidewire. For example, the catheter 102 and the balloon 112 may be delivered over the guidewire 216 (shown in FIG. 2B) and through a renal guide catheter (also referred to as a guide sheath). For further examples of guidewire-based delivery of ultrasound transducers, see U.S. Pat. No. 10,456,605, which was incorporated herein by reference above. However, it should be appreciated that any suitable steerable catheter or sheath, or any other suitable guiding device or method, may be used to deliver the distal portion 210 of the catheter 102 to a target anatomical location of the subject. Once delivered to a suitable location within the body lumen, the balloon 112 may be inflated with the cooling fluid 213 (e.g., under control of controller 120), and the transducer 111 may be actuated (e.g., by applying a voltage across the inner and outer electrodes 202, 203 under control of the controller 120) so as to deliver unfocused ultrasonic energy to the target anatomical location. The transducer 111 is sized for insertion in the body lumen and, in the case of insertion of the renal artery, for example, the transducer 111 may have an outer diameter of less than 2 mm, for example, about 1.5 mm and an inner diameter of less than 1.8 mm, for example, about 1 mm. As described in greater detail below, the length of the transducer 111 optionally may be selected such that the ultrasonic waves that it generates has a near field depth suitable for generating a lesion only within a desired region relative to the wall of a target body lumen.

It will be appreciated that the frequency, power, and amount of time for which the transducer 111 is actuated suitably may be selected based on the treatment to be performed. For example, the frequency optionally is in a range of from 1 to 20 MHz, e.g., 1-5 MHz, 5-10 MHz, 8.5-9.5 MHz, 10-15 MHz, 15-20 MHz, or 8-10 MHz, for example, about 9 MHz. Or, for example, the frequency optionally is in a range of below 1 MHz, e.g., 0.1-0.2 MHz, 0.2-0.3 MHz, 0.3-0.4 MHz, 0.4-0.5 MHz, 0.5-0.6 MHz, 0.6-0.7 MHz, 0.7-0.8 MHz, 0.8-0.9 MHz, or 0.9-1.0 MHz. Or, for example, the frequency optionally is in a range of above 20 MHz, e.g., 20-25 MHz, 25-30 MHz, or above 30 MHz. In an embodiment suitable for renal denervation, a frequency of about 9 MHz is used. Optionally, the power may be in a range of 5 to 80 W (e.g., 5 to 50 W, 5 to 10 W, 12.1-16.6 W, 10 to 20 W, 20 to 30 W, 30 to 40 W, 40 to 50 W, 50 to 60 W, 60 to 70 W, or 70 to 80 W, or may be more than 80 W). The specific power level that is selected and used for treatment may depend on various factors, such as, but not limited to, the particular design of the transducer, the size of the portion of the body lumen in which the transducer is located, and/or the like. In an embodiment suitable for renal denervation, a power of between about 26 W (for a renal artery that is about 3.5 mm in diameter) to about 36 W (for a renal artery that is about 8 mm in diameter) is used. As is known in the art, the acoustic power of the transducer can be determined using an acoustic radiation force balance (RFB) or derived by integrating the intensity field scanned with a hydrophone. The period of time during which the transducer 111 is actuated may be sufficient to complete the particular treatment being performed, and may depend on factors such as the power at the transducer, the frequency of ultrasonic energy emitted, the size of the body lumen in which the transducer is inserted, the size of the tissue region being treated, the age, weight and gender of the patient being treated, and/or the like. Illustratively, in some configurations the time period for which the transducer 111 may be actuated may be in a range of about 3 seconds to 5 minutes, e.g., 3-10 seconds, 3-30 seconds, 30 seconds to 1 minute, 30 seconds to 5 minutes, 1 to 3 minutes, about 2 minutes, 10 seconds to 1 minute, 1 to 2 minutes, 2 to 3 minutes, 3 to 4 minutes, or 4 to 5 minutes. Or, for example, the transducer 111 may be actuated for less than 10 seconds (s), e.g., 0.1-10 s, 1-2 s, 2-3 s, 3-4 s, 4-5 s, 5-6 s, 6-7 s, 7-8 s, 8-9 s, or 9-10 s. Or, for example, the transducer 111 may be actuated for more than 5 minutes (m), e.g., 5-6 m, 6-7 m, 7-8 m, 8-9 m, 9-10 m, 10-15 m, 15-20 m, or for more than 20 minutes. In specific embodiments, the period of time (also referred to as a duration) during which the transducer 111 is actuated can be of a fixed duration, e.g., 7 seconds, and an appropriate acoustic output power level may be selected based on the size of the portion of the body lumen in which the transducer 111 is located, so that the treatment is tailored to the specific tissue to be treated.

In various configurations, the delivery of ultrasound energy during the treatment may be continuous or substantially continuous, e.g., without any interruptions or fluctuations in frequency, power, duty cycle and/or any other parameters. Alternatively, one or more of the frequency, power, duty cycle, or any other parameter may be modified during the treatment. For example, in some configurations, the delivery of ultrasonic energy is modulated, e.g., between on and off, or between a relatively high level and a relatively low level, so as prevent or reduce the likelihood of overheating of adjacent (e.g., targeted or non-targeted) tissue. For examples of such modulation, see U.S. Pat. No. 10,499, 937 to Warnking, the entire contents of which are incorporated herein by reference.

In example configurations in which nerve tissue is to be treated, e.g., the nerves N illustrated in FIG. 2B, the transducer 111 may be positioned and configured so as to deliver ultrasonic energy through the wall of a body lumen that is adjacent to that nerve tissue, e.g., through the wall of the body lumen. In one non-limiting example, renal nerves to be treated using the transducer 111 may be located about 0.5 mm to 8 mm (e.g., about 1 mm to 6 mm) from the inner wall of the renal artery. In other examples, nerve tissue to be treated may be located less about 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, less than 0.5 mm, or more than 8 mm from the inner wall of a body lumen in which transducer is disposed. Under control of the controller 120, the transducer 111 generates unfocused ultrasonic energy that heats any suitable nerve tissue so as to at least partially neuromodulate such nerve tissue, e.g., cause complete or partial ablation, necrosis, or stimulation of such nerve tissue. The ultrasonic energy generated by the transducer 111 may radiate radially outward so as to target the nerve tissue regardless of the radial orientation of such nerve tissue relative to the body lumen. In some configurations, the unfocused ultrasonic energy is emitted along an entire, continuous circumference of the transducer 111. In other configurations, the ultrasonic energy is emitted non-continuously or intermittently around the circumference of the transducer 111. It should be appreciated that nerve tissue, and more specifically the renal nerves, are only one example of tissue that may be treated using an ultrasound transducer. Other examples of target anatomical regions that may be treated with an ultrasound transducer 111 are described elsewhere herein.

Additional options regarding designs and uses of ultrasound transducers and catheter-based ultrasound delivery systems are provided in the following patents and published applications, the entire contents of each of which are incorporated by reference herein: U.S. Pat. Nos. 6,635,054; 6,763,722; 7,540,846; 7,837,676; 9,707,034; 9,981,108; 10,350,440; 10,456,605; 10,499,937; and PCT Publication No. WO 2012/112165.

In accordance with certain embodiments of the present technology, the piezoelectric transducer body of the ultrasound transducer comprises a hollow tube of piezoelectric material having an inner surface and an outer surface. In certain such embodiments, a first electrode is disposed on one of the inner and outer surfaces of the hollow tube of piezoelectric material, and a second electrode is disposed on the other one of the inner and outer surfaces of the hollow tube of piezoelectric material. The hollow tube of piezoelectric material can be cylindrically shaped, such that it has a circular shaped radial cross-section. In certain embodiments suitable, e.g., for renal denervation, the piezoelectric material, of which the piezoelectric transducer body is made, is lead zirconate titanate 8 (PZT8), which is also known as Navy III Piezo Material. Raw PZT transducers may be plated with layers of copper, nickel and/or gold to create electrodes on surfaces (e.g., the inner and outer surfaces) of the piezoelectric transducer body. In alternative embodiments the hollow tube of piezoelectric material can have other shapes besides being cylindrical with a circular cross-section. Other cross-sectional shapes for the hollow tube of piezoelectric material, and more generally the piezoelectric transducer body, include, but are not limited to, an oval or elliptical cross-section, a square or rectangular cross-section, pentagonal cross-section, a hexagonal cross-section, a heptagonal cross-section, an octagonal cross-section, and/or the like. In still other embodiments, the piezoelectric transducer body is not hollow, e.g., can have a generally solid rectangular shape, or some other solid shape. The piezoelectric transducer body can be configured, e.g., to deliver acoustic energy in a frequency range of 8.5 to 9.5 MHz, but is not limited thereto. In accordance with certain embodiments, the piezoelectric transducer body is configured to produce an acoustic output power within a range of 5 to 45 Watts in response to an input electrical power within a range of 10 to 80 Watts, but is not limited thereto.

Figure 4A:
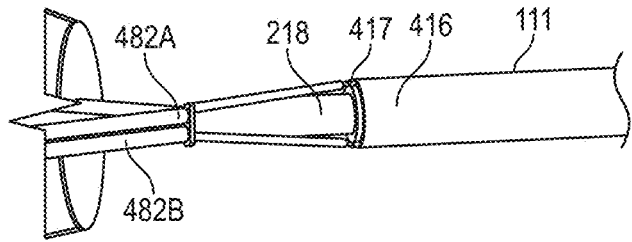
FIG. 4A illustrates a side view of a distal portion of the catheter, in accordance with an embodiment.
Figure 4B:
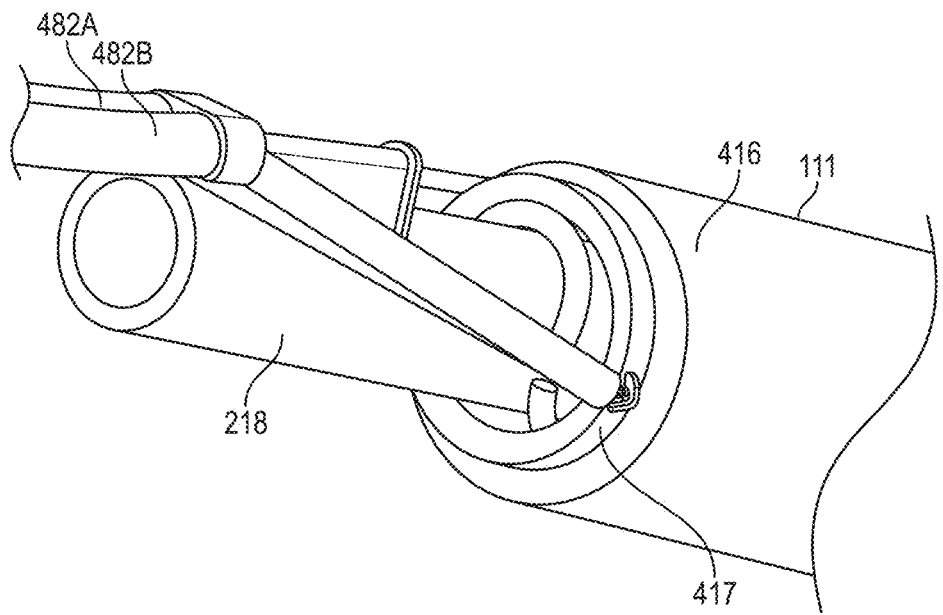
FIG. 4B illustrates a perspective view of the distal portion of the catheter shown in FIG. 4A, in accordance with an embodiment.

FIGS. 4A and 4B illustrate, respectively, side and perspective views of a distal portion of the catheter 102 according to an embodiment. As can be seen in FIGS. 4A and 4B, in accordance with certain embodiments, the ultrasound transducer 111 includes a non-stepped portion 416 and a stepped portion 417. In certain embodiments, the axial length of stepped portion 417 is about 0.4 mm and the axial length of a non-stepped portion 416 is about 6 mm. The non-stepped portion 416 of the transducer 111 can also be referred to as the main portion of the transducer 111. In certain embodiments, the non-stepped portion 416 of the transducer 111 is the portion of the transducer that produces the bulk of the ultrasonic energy delivered from the catheter 101. In certain embodiments, the stepped portion 417 has a different outer-diameter than the non-stepped portion 416 and behaves in a different manner than the non-stepped portion 416. In certain embodiments, a cylindrical portion of the balloon 112 (shown, e.g., in FIG. 2B) is at least as long as the length of non-stepped portion 416 in order to provide cooling protection equivalent to the length of the transducer 111. In certain embodiments, wherein the axial length of a non-stepped portion 416 is about 6 mm, the cylindrical portion 255 of balloon 112 has a length at least about 6 mm.

Figure 5:
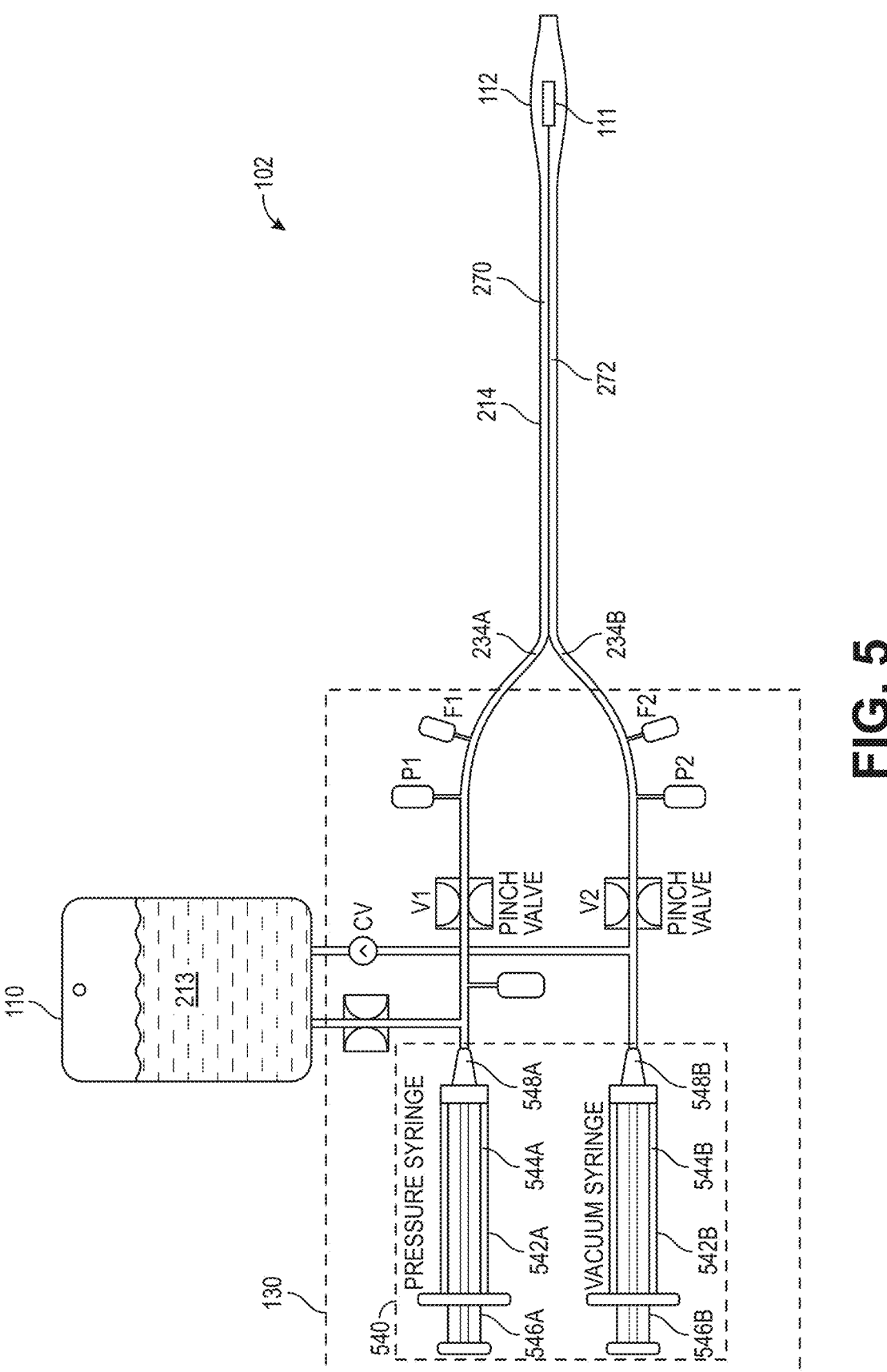
FIG. 5 illustrates example details of a fluid supply subsystem, in accordance with an embodiment.

Example details of the cartridge 130 and the reservoir 110, which were introduced above in the above discussion of FIG. 1, will now be described with reference to FIG. 5. The cartridge 130 and/or reservoir 110 can be parts of a fluid supply subsystem. However, it is noted that alternative fluid supply subsystems can alternatively be used to supply cooling fluid to and circulate cooling fluid through the balloon 112, while still being within the scope of the embodiments of the present technology described herein. Referring to FIG. 5, the reservoir 110 is shown as being implemented as a fluid bag, which can be the same or similar to an intravenous (IV) bag in that it can hang from a hook, or the like. The reservoir 110 and the cartridge 130 can be disposable and replaceable items.

The reservoir 110 is fluidically coupled to the cartridge 130 via a pair of fluidic paths, one of which is used as a fluid outlet path (that provides fluid from the reservoir to the cartridge), and the other one of which is used as a fluid inlet path (the returns fluid from the cartridge to the reservoir). The cartridge 130 is shown as including a syringe pump 540, which includes a pressure syringe 542*a* and a vacuum syringe 542*b*. The pressure syringe 542*a* includes a barrel 544*a*, a plunger 546*a*, and a hub 548*a*. Similarly, the vacuum syringe 542*b* includes a barrel 544*b*, a plunger 546*b*, and a hub 548*b*. The hub 548*a*, 548*b* of each of the syringes 542*a*, 542*b* is coupled to a respective fluid tube or hose. The cartridge 130 is also shown as including pinch valves V1, V2 and V3, pressure sensors P1, P2, and P3, and a check valve CV. While not specifically shown in FIG. 3C, the syringe pump 540 can include one or more gears and step-motors, and/or the like, which are controlled by the controller 120 (in FIG. 1) to selectively maneuver the plungers 546 of the pressure syringe 542*a* and the vacuum syringe 542*b*. Alternatively, the gear(s) and/or step-motor(s) can be implemented within the controller 120, and can be used to control the syringe pump 540.

In order to at least partially fill the barrel of the pressure syringe 542*a* with a portion of the cooling fluid that is stored in the reservoir 110, the pinch valves V1 and V2 are closed, the pinch valve V3 is opened, and the plunger 546*a* of the pressure syringe 542*a* is pulled upon to draw cooling fluid 213 into the barrel 544*a* of the of the pressure syringe 542*a*. The pinch valve V3 is then closed and the pinch valves V1 and V2 are opened, and then the plunger 546*a* of the pressure syringe 542*a* is pushed upon to expel cooling fluid from the barrel 544*a* of the pressure syringe 542*a* through the fluid tube attached to the hub 548*a* of the pressure syringe 542*a*. The cooling fluid expelled from the pressure syringe 542*a* enters the fluid lumen 270 (in the catheter shaft 214), via the fluidic inlet port 234*a* of the catheter 102, and then enters and at least partially fills the balloon 112. Simultaneously, the plunger 546*b* of the vacuum syringe 542*b* can be pulled upon to pull or draw cooling fluid from the balloon into the fluid lumen 272 (in the catheter shaft), through the fluidic outlet port 235*b* of the catheter 102, and then through fluid tube attached to the hub 548*b* of the vacuum syringe 542*b* and into the barrel 544*b* of the vacuum syringe 542*b*. In this manner, the cooling fluid can be circulated through the balloon 112. The balloon 112 can be inflated by supplying more cooling fluid to the balloon than is removed from the balloon. One or more of the pressure sensors P1, P2, and P3 can be used to monitor the pressure in the balloon 112 to achieve a target balloon pressure, e.g., of 10 pounds per square inch (psi), but not limited thereto. Once the balloon is inflated to a target pressure, e.g., between 10 psi and 30 psi, and/or size, the cooling fluid can be circulated through the balloon without increasing or decreasing the amount of fluid within the balloon by causing the same amount of fluid that is removed from the balloon 112 to be the same as the amount of fluid that is provided to the balloon 112. Also, once the target balloon pressure is reached, the ultrasound transducer 111 can be excited to emit ultrasound energy to treat tissue that surrounds the portion of the body lumen (e.g., a portion of a renal artery) in which the balloon 112 and the transducer 111 are inserted. When the ultrasound transducer 111 is emitting ultrasound energy it can also be said that the ultrasound transducer 111 is performing sonication, or that sonication is occurring. During the sonication, cooling fluid should be circulated through the balloon by continuing to push on the plunger 546*a* of the pressure syringe 542*a* and continuing to pull on the plunger 546*b* of the vacuum syringe 542*b*.

After the sonication is completed, and the balloon 112 is to be deflated so that the catheter 102 can be removed from the body lumen, the cooling fluid should be returned from the barrel 544*b* of the vacuum syringe 542*b* to the reservoir 110. In order to return the cooling fluid from the barrel 544*b* of the vacuum syringe 542*b* to the reservoir 110, the pinch valves V1, V2, and V3 are all closed, and the plunger of the vacuum syringe 542*b* is pushed on to expel the cooling fluid out of the barrel of the vacuum syringe 542*b*, past the check valve CV, and into the reservoir 110.

The pressure sensors P1, P2, and P3 can be used to monitor the fluidic pressure at various points along the various fluidic paths within the cartridge 130, which pressure measurements can be provided to the controller 120 as feedback that is used for controlling the syringe pump 540 and/or for other purposes, such as, but not limited to, determining the fluidic pressure within the balloon 112. Additionally, flow rate sensors F1 and F2 can be used, respectively, to monitor the flow rate of the cooling fluid that is being injected (also referred to as a pushed, provided, or supplied) into the balloon 112, and to monitor the flow rate of the cooling fluid that is being drawn (also referred to as a pulled or removed) from the balloon 112. The pressure measurements obtained from the pressure sensors P1, P2, and P3 can be provided to the controller 120 so that the controller 120 can monitor the balloon pressure. Additionally, flow rate measurements obtained from the flow rate sensors F1 and F2 can be provided to the controller 120 so that the controller 120 can monitor the flow rate of cooling fluid being pushed into and pulled from the balloon 112. It would also be possible for one or more pressure sensors and/or flow rate sensors to be located at additional or alternative locations along the fluidic paths that provide cooling fluid to and from the balloon 112.

Figure 6:
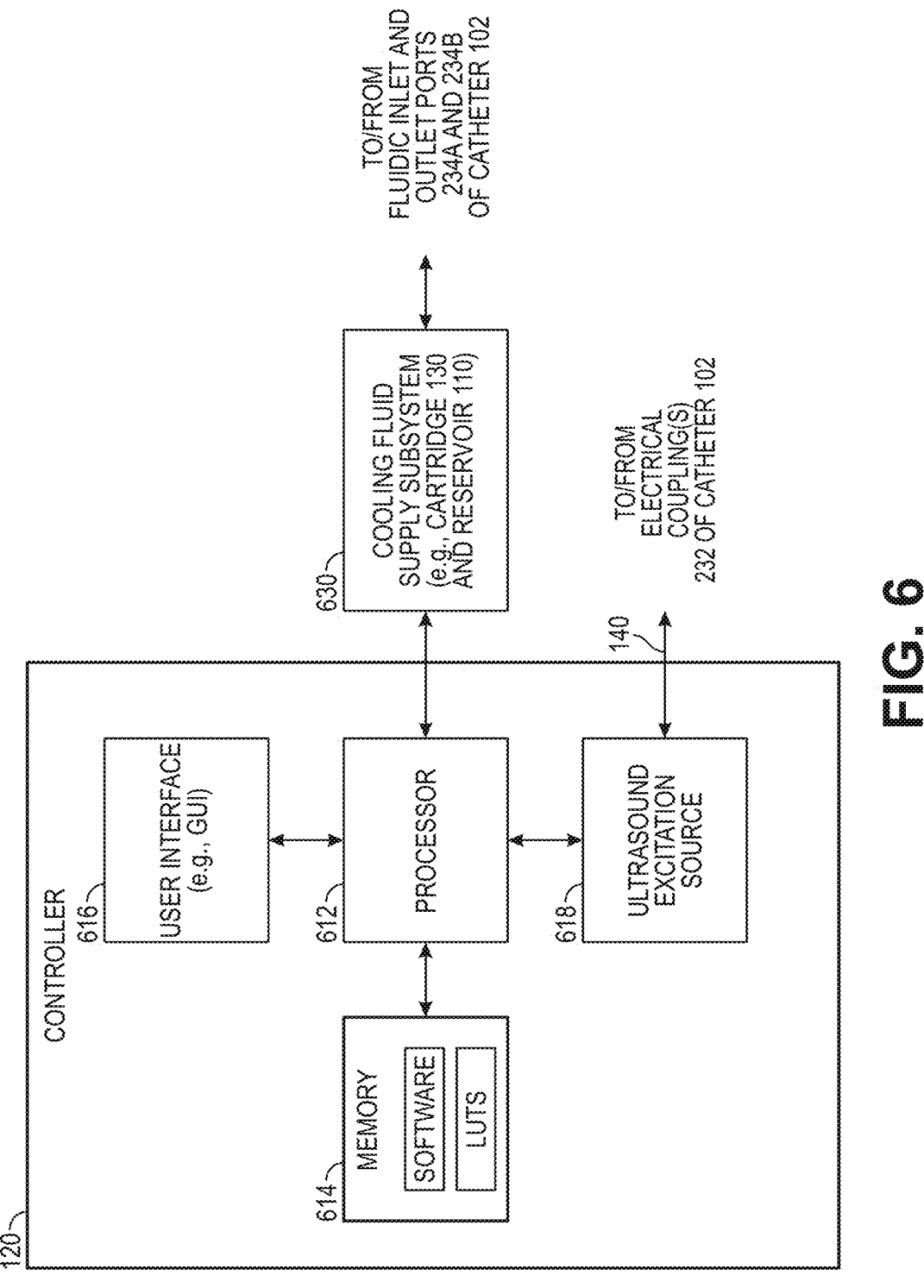
FIG. 6 illustrates example details of a controller, in accordance with an embodiment.

FIG. 6 will now be used to describe an example implementation of the controller 120, which was introduced in FIG. 1. Referring to FIG. 6, the controller 120 is shown as including one or more processors 612, a memory 614, a user interface 616, and an ultrasound excitation source 618, but can include additional and/or alternative components. While not specifically shown, a processor 612 can be located on a control board, or more generally, a printed circuit board (PCB) along with additional circuitry of the controller 120. The processor 612 can communicate with the memory 614, which can be a non-transitory computer-readable medium storing instructions. The processor 612 can execute the instructions to cause the system 100 to perform the methods described herein. The user interface 616 interacts with the processor 612 to cause transmission of electrical signals at selected actuation frequencies to the ultrasound transducer 111 via wires of the connection cable 140 and the cabling 282 that extends through the catheter shaft 112. These wires electrically couple the controller 120 to the transducer 111 so that the controller 120 can send electrical signals to the transducer 111, and receive electrical signals from the transducer 111. The processor 612 can control the ultrasound source 618 to control the amplitude and timing of the electrical signals so as to control the power level and duration of the ultrasound signals emitted by transducer 111. More generally, the controller 120 can control one or more ultrasound treatment parameters that are used to perform sonication. In certain embodiments, the excitation source 618 can also detect electrical signals generated by transducer 111 and communicate such signals to the processor 612 and/or circuitry of a control board. While the ultrasound excitation source 618 in FIG. 6 is shown as being part of the controller, it is also possible that the ultrasound excitation source 618 is external to the controller 120 while still being controlled by the controller 120, and more specifically, by the processor 612 of the controller 120.

The user interface 616 can include a touch screen and/or buttons, switches, etc., to allow for an operator (user) to enter patient data, select treatment parameters, view records stored on a storage/retrieval unit (not shown), and/or otherwise communicate with the processor 612. The user interface 616 can include a voice-activated mechanism to enter patient data or may be able to communicate with additional equipment so that control of the controller 120 is through a separate user interface, such as a wired or wireless remote control. In some embodiments, the user interface 616 is configured to receive operator-defined inputs, which can include, e.g., a duration of energy delivery, one or more other timing aspects of the energy delivery pulses (e.g., frequency, duty cycle, etc.), power, body lumen length, mode of operation, patient parameter, such as height and weight, and/or verification of artery diameter, or a combination thereof. Example modes of operation can include (but are not limited to): system initiation and set-up, catheter preparation, balloon inflation, verification of balloon apposition, pre-cooling, sonication, post-cooling, balloon deflation, and catheter removal, but are not limited thereto. In certain embodiments, the user interface 616 provides a graphical user interface (GUI) that instructs a user how to properly operate the system 100. The user interface 616 can also be used to display treatment data for review and/or download, as well as to allow for software updates, and/or the like.

The controller 120 can also control a cooling fluid supply subsystem 630, which can include the cartridge 130 and reservoir 110, which were described above with reference to FIGS. 1 and 5, but can include alternative types of fluid pumps, and/or the like. The cooling fluid supply subsystem 630 is fluidically coupled to one or more fluid lumens (e.g., 270 and 272) within catheter shaft 214 which in turn are fluidically coupled to the balloon 112. The cooling fluid supply subsystem 630 can be configured to circulate a cooling liquid through the catheter 102 to the transducer 111 in the balloon 112. The cooling fluid supply subsystem 630 may include elements such as a reservoir 110 for holding the cooling fluid 213, pumps (e.g., syringes 542a and 542b), a refrigerating coil (not shown), or the like for providing a supply of cooling fluid to the interior space of the balloon 112 at a controlled temperature, desirably at or below body temperature. The processor 612 interfaces with the cooling fluid supply subsystem 630 to control the flow of cooling fluid into and out of the balloon 112. For example, the processor 612 can control motor control devices linked to drive motors associated with pumps for controlling the speed of operation of pumps (e.g., syringes 542a, 542b). Such motor control devices can be used, for example, where the pumps are positive displacement pumps, such as peristaltic pumps. Alternatively, or additionally, a control circuit may include structures such as controllable valves connected in the fluid circuit for varying resistance of the circuit to fluid flow (not shown). The processor 612 can monitor pressure measurements obtained by the pressure sensors (e.g., P1, P2 and P3) to monitor and control the cooling fluid through the catheter 102 and the balloon 112. The pressure sensors can also be used to determine if there is a blockage and/or a leak in the catheter 102. While the balloon 112 is in an inflated state, the pressure sensors can be used to maintain a desired pressure in the balloon 112, e.g., at a pressure of between 10 psi and 30 psi, but not limited thereto. As will be described in additional detail below, the processor 612 can use sensor measurements from one or more of the pressure sensors and/or other sensors to determine when the balloon 112 is in apposition with a body lumen as well as to estimate an inner diameter of a body lumen in order to select an appropriate dose of ultrasound energy to be delivered to treat tissue surrounding the body lumen.

Estimating Body Lumen Size

As noted above, for various reasons, it is important to know the inner diameter (size) of a body lumen (e.g., a renal artery) into which an ultrasound transducer and/or balloon is inserted, or is/are to be inserted, e.g., so that an appropriate dose of neuromodulation energy, e.g., ultrasound energy, is selected and used for a treatment. Vessel sizing previously has been done through, e.g., computed tomography (CT) imaging with contrast agent, fluoroscopy, magnetic resonance imaging (MRI), diagnostic intravascular ultrasound, optical coherence tomography (OCT), intracardiac echocardiography (ICE).

However, such imaging techniques have limited resolution or require additional equipment, time, and money or is not real time. Certain embodiments of the present technology are directed to techniques for estimating the inner diameter of a body lumen, or a surrogate thereof, without using CT imaging, MRI, OCT, ICE, fluoroscopy, separate intravascular diagnostic ultrasound equipment. Certain embodiments of the present technology use CT imaging, MRI, OCT, ICE, fluoroscopy and/or separate diagnostic ultrasound equipment to confirm and/or add more accuracy to the novel techniques of measuring body lumen diameter described herein.

Certain such embodiments described herein utilize balloon pressure measurements obtained from one or more pressure sensors to estimate a body lumen diameter or a surrogate thereof. Other embodiments described herein utilize fluid flow rate measurements obtained from one or more flow rate sensors to estimate a body lumen diameter or a surrogate thereof. Still other embodiments utilize sensor measurements from additionally or alternative types of sensors, such as a microphone or an accelerometer, to estimate a body lumen diameter or a surrogate thereto. Still further embodiments rely on ultrasound reflections to estimate a body lumen size or surrogate thereof. Certain embodiments use one or more (e.g., all) of the novel techniques of measuring body lumen diameter described herein. Certain embodiments use one or more (e.g., all) of the novel techniques of measuring body lumen diameter described herein, together with one or more of CT imaging, fluoroscopy, and/or separate diagnostic ultrasound equipment.

Use of Pressure Measurements to Estimate Body Lumen Size and/or Select Ultrasound Treatment Parameters Embodiments of the present technology that utilize balloon pressure measurements, obtained from one or more pressure sensors (e.g., P1 and/or P2) to estimate a body lumen diameter or a surrogate thereof, will now be described with reference to FIGS. 5, 7A, 7B, and 8. It will be appreciated that the linear piecewise representation of the figures may be an approximation of real data. That is, real data may not have such clean lines and discrete inflections. The conceptual approximation may, however, be generated by filtering real data, and provides an illustration of the concept described below.

Figure 7A:
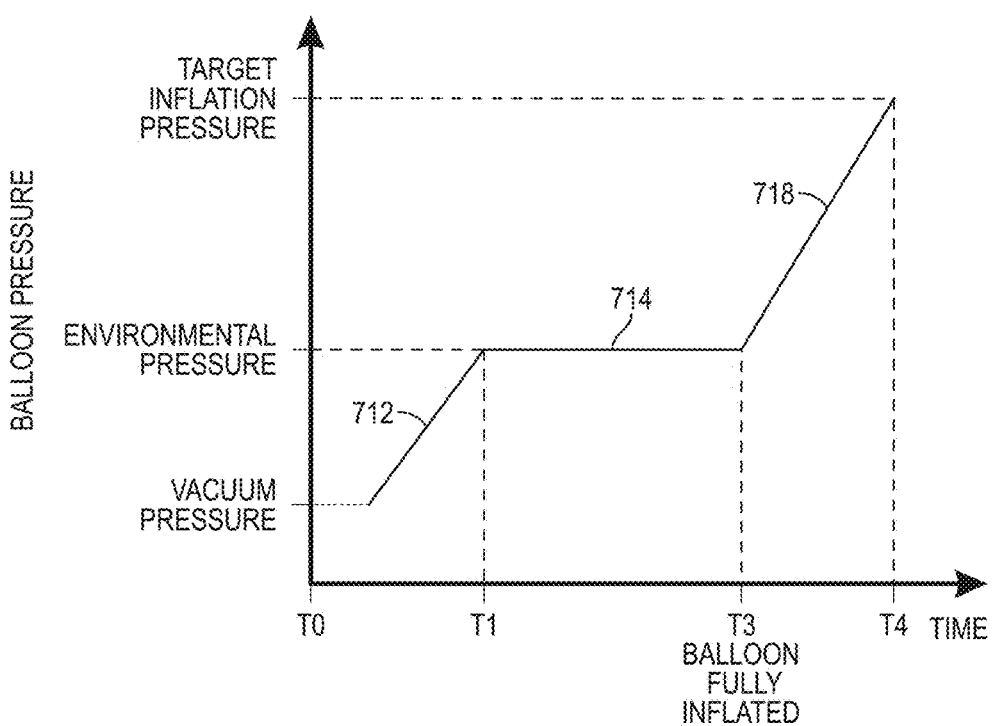
FIGS. 7A and 7B illustrate example graphs of balloon pressure versus time, which are used to explain how pressure within a non-compliant balloon, which is being filled with a fluid, changes over time as the fluid is being provided to the balloon, in accordance with an embodiment.
Figure 7B:
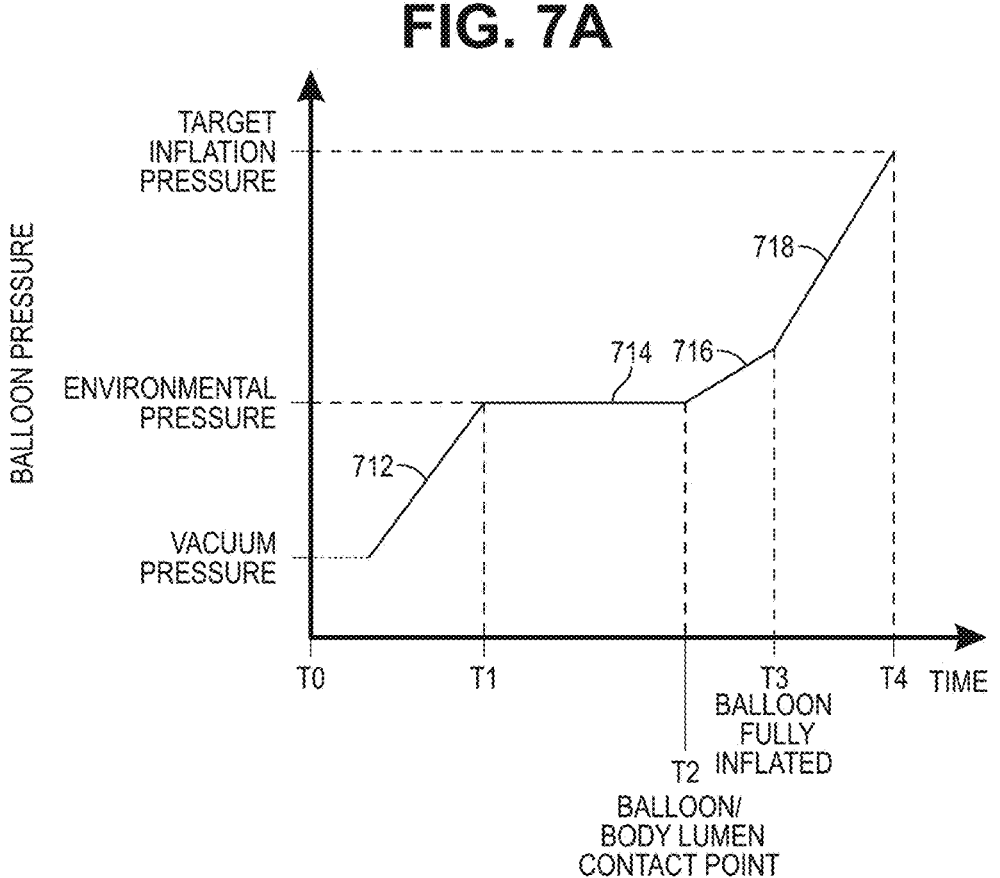

FIGS. 7A and 7B, which are example graphs of balloon pressure versus time, are used to explain how pressure within a balloon that is being filled with a fluid (e.g., a cooling fluid) can change over time as the fluid is injected into the balloon. More specifically, the pressure versus time curve in FIG. 7A is for a catheter that has not been inserted into a body lumen, i.e., is in vitro, and the pressure versus time curve in FIG. 7B is for the same catheter after it has been inserted into a body lumen. For the purpose of discussing FIGS. 7A and 7B, it is assumed that the catheter is provided with a non-compliant balloon that once fully filled with fluid does not expand in volume any further, but may increase in pressure as additional fluid is injected into the balloon. It is also assumed that the diameter of the non-compliant balloon, when fully inflated, is greater than the potential maximum inner diameter of the body lumen into which the non-compliant balloon is to be inserted. The volume of such a non-compliant balloon, when fully inflated with cooling fluid, can be, e.g., 1-2 milliliters (mL).

When the balloon 112 is devoid of fluid, it is at a negative pressure (also referred to as a vacuum pressure) relative to environmental pressure, and while the balloon is being filled with fluid that is being injected into the balloon, the pressure in the balloon 112 can gradually rise in accordance with a positive slope (indicative of balloon pressure versus time). The slope corresponds to a rate of pressure change, e.g., a change in pressure over a period of time. It is noted that the terms balloon pressure, pressure within the balloon, pressure within the interior of the balloon, and the like, as used herein, are used interchangeably. It is also noted that the units of balloon pressure can be pounds per square inch (psi), or in Newtons per square meter, which is also known as a Pascal, but are not limited thereto. Unless stated otherwise, it is assumed that the pressure measurements are in pounds per square inch (psi).

Referring to FIGS. 7A and 7B, the portion of the curves labeled 712, which has a positive slope, corresponds to the period of time (between times t0 and t1) during which the pressure within the balloon is increasing, without the volume of the balloon increasing, until the pressure in the balloon reaches environmental pressure (at time t1). The portion of the curves labeled 714, which is substantially constant or static and has substantially no slope, corresponds the period of time (between times t1 and t3 in FIG. 7A, or between times t1 and t2 in FIG. 7B) during which the balloon is being filled with the cooling fluid and the cooling fluid is expanding the volume of the balloon without increasing the pressure in the balloon beyond the environmental pressure. More particularly, over the so-called minimal slope segment between times t1 and t3 in FIG. 7A and times t1 and t2 in FIG. 7B, pressure within the balloon remains essentially the same as the volume of the balloon increases during the inflation process. It is noted that when the balloon is not inserted into a body lumen, i.e., is in vitro, the environment pressure is atmospheric pressure. After the balloon has been inserted into a body lumen, the environment pressure is the blood pressure within the body lumen, which may vary within a relatively small range over each cardiac cycle, but is substantially constant. The portion of the curves labeled 718, which has a positive slope, corresponds to the period of time (following time t3) after which the balloon has been fully inflated such that as additional cooling fluid is injected into the balloon the volume of the balloon does not increase but the pressure in the balloon increases. The time t4 in the FIGS. 7A and 7B is the time at which the balloon 112 reaches its target pressure. The target balloon pressure can be, e.g., 10 psi, but higher or lower target inflation pressures can alternatively be used. It is noted that the times t1, t2, t3, and t4 in the graphs are temporal variables that correspond to specific inflection points in the curves, wherein such times are capable of being determined, e.g., by the controller 120, based on pressure measurements that are obtained using one or more pressure sensors (e.g., P1 and/or P2) and provided to the controller 120.

The curve inflections, as described herein, correspond to changes in a fluid parameter, such as pressure that is above a threshold change. For example, the threshold change can be a change in a rate of pressure change that exceeds a predetermined rate. When the instantaneous rate of change exceeds the predetermined level at a particular point in time, then the transition between the segment leading to the particular point and the segment going away from the particular point can be identified as an inflection in the curve. The inflections can define the start and stop of curve segments. For example, the minimal slope segment can extend between a start inflection and a stop inflection.

In addition to determining inflection points in the curves, the controller may also determine durations, slopes, or inclines for each of the curve segments. For example, the controller can determine that the curve segment between times t1 and t3 in FIG. 7A (or between times t1 and t2 in FIG. 7B) has a slope and/or incline that is less than the slope(s) of adjacent segments. The slope of the segment between times t1 and t3 can be substantially equal to zero, and the adjacent slopes can be greater than zero. Accordingly, the curve segment may be referred to as a zero-slope segment, or a minimal slope segment. Similarly, the controller can determine that the curve segment between times t3 and t4 in FIG. 7A (or between times t2 to t3 and t3 to t4 in FIG. 7B) has a slope and/or incline that is negative or positive in value. Accordingly, the curve segments adjacent to the minimal slope segment may be referred to as non-zero-slope segments, or non-minimal slope segments.

In FIG. 7B, the portion of the curve labeled 716, which has a positive slope, corresponds to the period of time between when the not yet fully inflated balloon comes into apposition (at time t2) with the body lumen into which the balloon is inserted and when the balloon is fully inflated (at time t3). The inflection point in the curve in FIG. 7B that corresponds to the time t2 (which is a variable) is the point in time where the balloon has been sufficiently inflated such that an outer circumference of the balloon comes into apposition with an inner circumference of the body lumen in which the balloon is positioned. Accordingly, it can be said that the inflection point at time t2 corresponds to when the balloon becomes in apposition with the body lumen. The reason the pressure begins to increase at the time t2 is that once the balloon becomes in apposition with the body lumen, the interior circumferential surface of the body lumen pushes back against the outer circumferential surface of the balloon as additional fluid is injected into the balloon.

There are various different types of body lumens into which the balloon 112 may be inserted, such as, but not limited to, a renal artery. For most patients, their renal arteries will have an inner diameter within the range of 3 mm to 8 mm. Further, it is noted that the diameter of a renal artery may vary along the length of the renal artery. For the purpose of this discussion, it is presumed that the body lumen, into which the catheter and balloon are being inserted, has an inner diameter within the range of 3 mm to 8 mm. However, it is noted that need not be the case if the catheter and the balloon are intended to be used with other types of body lumens. Further, for the purpose of this discussion, it is presumed that the outer diameter of the balloon at the target balloon pressure does not exceed 8 mm. However, it is noted that need not be the case if the catheter and the balloon are intended to be used with other types of body lumens. Examples of other types of body lumens into which the balloon 112 and the transducer 111 (or the transducer 111 without a balloon 112 or a balloon 112 without a transducer) can be inserted, include, but are not limited to, a hepatic artery, a splenic artery, a celiac trunk, a superior mesenteric artery, or an inferior mesenteric artery.

Between times t2 and t3, the pressure within the balloon that is not yet fully inflated, continues to increase due to the resistance of the interior surface body lumen against the exterior surface of the balloon. Further, between times t2 and t3, as the diameter and the volume of the balloon expands (until the balloon is fully inflated at time t3), the exterior surface of the balloon pushes against the interior surface of the body lumen thereby stretching or expanding the body lumen. Assuming a constant flow rate of the fluid being injected into the balloon, it should be appreciated that the time between times t1 and t2 is dependent upon the size of the body lumen in which the balloon is inserted. More specifically, presuming the balloon is being inflated at a fixed predetermined rate, the shorter the length of time between times t1 and t2 (and more specifically, the corresponding inflections points in the curve in FIG. 7B), the smaller the inner diameter of the body lumen, and the longer the length of time between times t1 and t2 the larger the inner diameter of the body lumen. It is noted that whenever a diameter of a body lumen is being discussed herein, the diameter being referred to is the inner diameter of the body lumen, and thus, an inner diameter of a body lumen can be referred to more succinctly herein as the diameter of the body lumen.

In accordance with certain embodiments of the present technology described below, measurements of the pressure within the balloon, obtained using one or more pressure sensors (e.g., P1, P2 and/or P3 in FIG. 5), are used to determine an estimate of the size (i.e., inner diameter) of a body lumen, or a surrogate thereof. The estimate of the body lumen size (or the surrogate thereof) can then be used to select one or more treatment parameters, such as a therapeutically effective neuromodulation energy, fluid flow rate, or desired balloon pressure (the balloon pressure used during sonication). In an embodiment, the estimate of the body lumen size (or the surrogate thereof) can then be used to select one or more ultrasound treatment parameters, such as, but not limited to, a level of voltage or power that is provided to an ultrasound transducer (within the balloon) to cause the ultrasound transducer to emit ultrasound energy that is used to treat patient tissue surrounding the body lumen and/or the cooling fluid flow rate and/or the optimal pressure of the balloon 112. Such measurements of the pressure within the balloon 112 can also be referred to herein as balloon pressure measurements, or more succinctly, as pressure measurements. Alternatively, rather than initially estimating the body lumen size or the surrogate thereof based on pressure measurements, and then using the estimate of the body lumen size to select the treatment parameter(s), the treatment parameter(s) can instead be determined based on the pressure measurements. In other words, the operation of estimating the body lumen size based on pressure measurements can be eliminated, if so desired, where the sole purpose of estimating the body lumen size is to select the appropriate level of voltage, power, cooling fluid flow rate, and/or desired (energy delivery/sonication) balloon pressure. Rather, an analysis of the pressure measurements themselves can be used to select the treatment parameter(s), while skipping the intermediate operation of estimating the body lumen size. It is noted that phrases such as determining an estimate of the size of a body lumen, and estimating the size of a body lumen, and the like, are used interchangeably herein. Further, unless stated otherwise, it is assumed that a size of a portion of a body lumen refers to an inner diameter of the body lumen.

In an embodiment, a graphic user interface may be used to display the determined body lumen diameter and/or the treatment parameters. In an embodiment, the graphic user interface may ask the user to confirm the body lumen diameter and/or the treatment parameters prior to providing a therapeutically-effective neuromodulation energy, e.g., thermally ablative ultrasound or RF energy.

In an embodiment, the controller determines an inflection point t4, the point in time when the balloon pressure reaches a target balloon pressure, e.g., 10 psi, but not limited thereto, and automatically generates a therapeutically-effective neuromodulation energy, e.g., thermally ablative ultrasound or RF energy to a treatment site.

Referring briefly back to FIG. 5, shown therein is a pressure sensor P1 that is located within or adjacent to the fluid output path of the cartridge 130 and a pressure sensor P2 that is located within or adjacent to the fluid return path of the cartridge 130, which fluid output and return paths are used to transfer cooling fluid between the cartridge 130 and the balloon 112. This enables the controller 120 to obtain measurements of the fluid output pressure and the fluid return pressure in real-time or near-real-time. Because the system is a closed system with substantially symmetric flow, with the balloon 112 being in the center of the flow path, averaging the fluid output pressure (also referred to as a fluid supply pressure) and the fluid return pressure, obtained respectively by the pressure sensors P1 and P2, provides for a good estimate of the balloon pressure. The balloon pressure is monitored, using such pressure sensors, while the cooling fluid is being injected into the balloon at a fixed rate using the pressure syringe 542a, or some other type of fluid pump. Accordingly, real-time or near-real-time measurements of balloon pressure are being obtained by the controller 120 while the cooling fluid is being used to inflate the balloon 112, which enables the controller 120 to identify the various inflection points and phases or time periods described above with reference to FIGS. 7A and 7B. More specifically, the controller 120 can identify the various inflection points (e.g., at times t1, t2, and/or t3) and the various phases or segments (e.g., between times t0 and t1, between times t1 and t2, between times t2 and t3, and between times t3 and t4) that correspond to the portions of the curve in FIG. 7B labeled 712, 714, 716, and 718. Referring to FIG. 7B, the inflection point at time t1 corresponds to the point in time when the balloon pressure transitions from vacuum pressure to environmental pressure, the inflection point at time t2 corresponds to the point in time when the balloon becomes in apposition with the body lumen, and the inflection point at time t3 corresponds to the point in time when the balloon becomes fully inflated. The time t4, as noted above, is the point in time when the balloon pressure reaches a target balloon pressure, e.g., 10 psi, but not limited thereto.

The controller 120 can identify the various inflection points or segments mentioned above based on the pressure measurements obtained from one or more of the pressure sensors (e.g., P1 and/or P2). For example, the inflection point at time t1 (that corresponds to the point in time when the balloon pressure transitions from vacuum pressure to environmental pressure) can be identified when pressure measurements transition from gradually increasing over time to staying substantially constant over time. For another example, the inflection point at time t2 (that corresponds to the point in time when the balloon becomes in apposition with the body lumen) can be identified when the pressure measurements transition from staying substantially constant over time to gradually increasing over time. In certain embodiments, a running average of the pressure measurements (e.g., a running average of the N most recent pressure measurements, where N is an integer that is at least 2) is determined by the controller 120, and the controller 120 analyzes the running average to identify the inflection points. Alternatively, or additionally, the pressure measurements can be filtered, e.g., by a low pass filter (LPF), before being analyzed by the controller 120 to identify the various inflection points.

In accordance with certain embodiments of the present technology, the controller 120 identifies the inflection points in the pressure versus time curve (shown in FIG. 7B) that corresponds to the times t1 and t2, so that the length of time (also referred to as a duration) corresponding to the substantially flat portion of the curve 714 can be determined. The duration between times t1 and t2 can be determined by determining a difference between the times t2 and t1. Alternatively, the controller 120 can start a timer when the inflection point at time t1 is identified and can stop the timer when the inflection point at time t2 is identified, in which case the duration would be the value of the time when the timer is stopped. Other ways for determining the duration of time between the times t1 and t2 are also possible and within the scope of the present technology.

The time t4 in the FIGS. 7A and 7B is the time at which the balloon 112 reaches its target pressure. The target balloon pressure can be, e.g., 10 psi, but higher or lower target inflation pressures can alternatively be used. It is noted that the times t1, t2, t3, and t4 in the graphs are temporal variables that correspond to specific inflection points in the curves, wherein such times are capable of being determined, e.g., by the controller 120, based on pressure measurements (or other parameter measurements) that are obtained or detected using one or more sensors, such as pressure sensors (e.g., P1 and/or P2), and provided to the controller 120.

Figure 8:
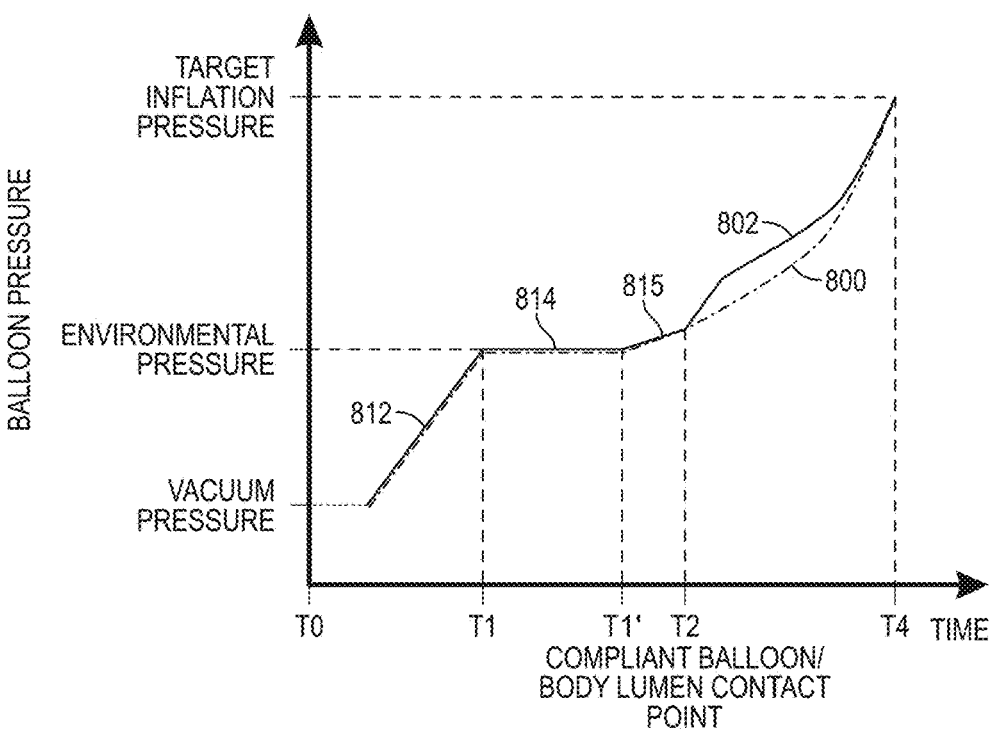
FIG. 8 illustrates an example graph of balloon pressure versus time, which is used to explain how pressure within a compliant balloon, which is being filled with a fluid, changes over time as the fluid is being provided to the balloon, in accordance with an embodiment.

As noted above, the example curve shown in FIG. 7B, of pressure versus time, is for a non-compliant balloon. As also noted above, once a non-compliant balloon is fully inflated with fluid, the non-compliant balloon does not expand in volume any further, but may increase in pressure as additional fluid is injected into the balloon. A curve of pressure versus time can look somewhat different for a compliant balloon that continues to increase in size as additional fluid is injected into the balloon. Referring to FIG. 8, the dashed-line curve 800 is for a compliant balloon that has not been inserted into a body lumen, i.e., is in vitro, and the solid line curve 802 is for the same compliant balloon after it has been inserted into a body lumen. The portion of the curves labeled 812, which has a positive slope, corresponds to the period of time (between times t0 and t1) during which the pressure within the compliant balloon is increasing, without the volume of the compliant balloon increasing, until the pressure in the balloon reaches environmental pressure (at time t1). The portion of the curves labeled 814, which is substantially constant or static and has substantially no slope, corresponds the period of time (between times t1 and t1') during which the balloon is being filled with the cooling fluid and the cooling fluid is expanding the volume of the balloon without increasing the pressure in the balloon beyond the environmental pressure. It is noted that when the balloon is not inserted into a body lumen, i.e., is in vitro, the environment pressure is atmospheric pressure. After the balloon has been inserted into a body lumen, the environment pressure is the blood pressure within the body lumen, which may vary within a relatively small range over each cardiac cycle, but is substantially constant. The portion of the curves labeled 815, which has a positive slope, corresponds to the period of time (following time t1') after which the balloon has been sufficiently inflated such that as additional cooling fluid is supplied to the balloon the volume of the balloon and the pressure in the balloon both increase. In other words, at the point in time t1' the material from which the balloon is made begins to be stretched. Following time t1', if the compliant balloon that has not been inserted into a body lumen then its pressure versus time curve can follow the dashed-line curve 800. However, if the compliant balloon has been inserted into a body lumen, then there is a point in time, labeled t2, that the compliant balloon can come into apposition with the body lumen, at which point the pressure versus time curve 802 can begin to deviate from the in vitro pressure versus time curve 800. By providing the controller 120 with sufficient information about the in vitro pressure versus time curve 800 for the compliant balloon, the controller 120 can detect the inflection point at time t2 (that corresponds to the point in time when the balloon becomes in apposition with the body lumen wall) based on pressure measurements obtained from one or more of the pressure sensors (e.g., P1 and/or P2). In other words, the controller 120 can detect the inflection point at time t2 (that corresponds to the point in time when the balloon becomes in apposition with the body lumen wall) by detecting when the pressure versus time curve of the balloon inserted into a body lumen deviates from the pressure versus time curve that the balloon would experience if not constrained at all by a circumferential inner wall of a body lumen.

Regardless of whether the balloon 112 is a non-compliant balloon, or a compliant balloon, by knowing how much fluid is being supplied to the balloon, and how much time occurred between the times t1 and t2, the controller 120 can determine the amount of fluid that was supplied to the balloon between the times t1 and t2. For example, if the balloon is being inflated at a rate of 5 milliliters per second (mL/sec), and there is 2.2 seconds (sec) between times t1 and t2, then the controller 120 can calculate that 11 mL of cooling fluid was supplied to the balloon between times t1 and t2 (i.e., 5 mL/sec*2.2 sec=11 mL). An equation or look-up-table can be produced and stored in the memory of the controller 120, which can be used to determine an estimate of the diameter of a body lumen based on the amount of fluid that supplied to the balloon 112 between the times t1 and t2. An example of such a look-up-table is shown in Table 1 below. It is noted that if the cooling fluid is being removed from the balloon at the same time that cooling fluid is being provided to the balloon, as could likely be the case, then the amount of fluid being supplied to the cooling fluid at any given time can be the differential flow rate. For an example, if 6 mL/sec of cooling fluid is being injected into the balloon while 1 mL/sec of cooling fluid is being removed from the balloon, then the differential flow rate would be 5 mL/sec, and it can be said that a net of 5 mL/sec of cooling fluid is being supplied to the balloon and used to inflate the balloon.

TABLE 1

| Volume of Fluid supplied to the balloon between times t1 and t2 | Estimate of body lumen diameter |
|---|---|
| Volume-a | Diameter-a |
| Volume-b | Diameter-b |
| Volume-c | Diameter-c |
| . | . |
| . | . |
| . | . |
| Volume-z | Diameter-z |

Alternatively, if the flow rate or differential flow rate is constant, then an equation or look-up-table can be produced and stored, which can be used to determine an estimate of a diameter of a body lumen based on the length of time between the times t1 and t2. An example of such a look-up-table is shown below in Table 2.

TABLE 2

| Time between times t1 and t2 | Estimate of body lumen diameter |
|---|---|
| Time-a | Diameter-a |
| Time-b | Diameter-b |
| Time-c | Diameter-c |
| . | . |
| . | . |
| . | . |
| Time-z | Diameter-z |

The above described look-up-tables can be generated, for example, through experimentation, calculations and/or simulations, and a different respective look-up-table can be generated for each of a plurality of different types and/or sizes of balloons that may be used.

In certain embodiments, a patient's blood pressure measurement is entered into the memory of the controller 120. A timer is initiated when the balloon 112 is at a known pressure, e.g., a negative or vacuum pressure, (time t0), whereupon the controller begins to inflate the balloon 112. The controller 120 identifies the inflection point in the pressure versus time curve that corresponds to the time t2. In certain embodiments, the memory of controller 120 includes a look-up-table that correlated the time it takes for balloon 112 to go from the known pressure (e.g., vacuum pressure) at t0 to environmental pressure (t1) using the inputted patient's blood pressure. Controller 120 then subtracts the time between t0 to t1 from time t0 to t2 to determine the time between t1 and t2 and uses the time between t1 and t2 to determine an estimate of a size of the portion of the body lumen, or a surrogate thereof. By how much time occurred between the times t1 and t2, the controller 120 can determine the amount of fluid that was supplied to the balloon between the times t1 and t2. For example, if the balloon is being inflated at a rate of 5 milliliters per second (mL/sec), and there is 2.2 seconds (sec) between times t1 and t2, then the controller 120 can calculate that 11 mL of cooling fluid was supplied to the balloon between times t1 and t2 (i.e., 5 mL/sec*2.2 sec=11 mL). An equation or look-up-table can be produced and stored in the memory of the controller 120, which can be used to determine an estimate of the diameter of a body lumen based on the amount of fluid supplied to the balloon 112. The controller then displays on the user interface, the estimated size of the portion of the body lumen, or the surrogate thereof.

In accordance with certain embodiments, rather than estimating the diameter of the body lumen based on the duration of time between the times t1 and t2, discussed with reference to FIGS. 7B-8, the body lumen diameter can be estimated using the following equations:

$$\text{Total injected volume} = \text{pump flow rate}*\text{time}. \tag{1}$$

$$\text{Volume of system} = \text{volume of pumps and flow tubes/manifold flow path (cartridge,known)} + \text{volume of the catheter (known)} + \text{volume of inflated balloon (calculated)}. \tag{2}$$

$$\text{Volume of inflated balloon} = 4\pi*\text{balloon diameter}^2*\text{balloon length}. \tag{3}$$

$$\text{Body lumen inner diameter} = \text{balloon diameter at apposition} = \text{sqrt(total injected volume} - \text{volume of cartridge} - \text{volume of the catheter)/}(\tfrac{1}{4}\pi*\text{balloon length}). \tag{4}$$

One of ordinary skill in the art reading this disclosure would appreciate that various other equations and/or look-up-tables, besides those specifically described herein, can alternatively be used to determine an estimate of a diameter of a body lumen while being within the scope of the embodiments described herein.

In accordance with certain embodiments, once an estimate of a body lumen diameter is determined, an equation or look-up-table can be used to select a level of voltage or power that is provided to an ultrasound transducer (that is positioned within the balloon) to cause the ultrasound transducer to emit ultrasound energy that is used to treat patient tissue surrounding the body lumen. An example of such a look-up-table is shown below in Table 3. More generally, once an estimate of the body lumen diameter is determined, one or more tissue treatment parameters can be selected based thereon.

TABLE 3

| Estimate of body lumen diameter | Voltage level applied between electrodes of ultrasound transducer |
|---|---|
| Diameter-a | Voltage-a |
| Diameter-b | Voltage-b |
| Diameter-c | Voltage-c |
| . | . |
| . | . |
| . | . |
| Diameter-z | Voltage-z |

Instead of specifying a voltage level (to be applied between electrodes of an ultrasound transducer), for each of a plurality of different body lumen diameters, a look-up-table can specify the acoustic output power level, in watts (W), that is to be output for each of a plurality of different lumen diameters, and optionally can specify addition values, such as respective lesion target values and acoustic energy densities. An example of such a look-up-table is shown in Table 4 below.

TABLE 4

| Estimated body lumen diameter (mm) | Lesion Target Volume (mL) | Acoustic Output Power (W) |
|---|---|---|
| Diameter-a | Volume-a | Power-a |
| Diameter-b | Volume-b | Power-b |
| Diameter-c | Volume-c | Power-c |
| . | . | |
| . | . | |
| . | . | |
| Diameter-z | Volume-z | Power-z |

Where an estimated body lumen diameter falls between two diameters included in the look-up-table, the appropriate acoustic output power can be determined by determining an average (which may be a weighted average) of two of the acoustic output power values included in the table, or an interpolation can be used to select the appropriate acoustic output power. For a simple example, if Diameter-b were 5 mm and Diameter-c were 6 mm, and the estimated body lumen diameter is 5.5 mm, then the acoustic output power level to be applied can be determined by averaging the acoustic output power level that would be used associated with Diameter-b and Diameter-c, i.e., by determining the average of Power-b and Power-c. If the estimated body lumen diameter is 5.2 mm, then the acoustic output power level to be applied can be determined by determining a weighted average of the acoustic output power level that would be used if the diameter were 5 mm and the acoustic output power level that would be used if the diameter were 6 mm, e.g., by calculating Power-b*0.8+Power-c*0.2. These are just a few examples of how averaging or interpolation can be performed, which are not intended to be all encompassing. The controller 120 can then use an equation or further look-up-table to determine the voltage level that is to be applied between electrodes of the ultrasound transducer, i.e., to determine what voltage level is needed to achieve the desired acoustic output power.

An alternative look-up-table can specify the acoustic output power level that is to be output for each of a plurality of different durations of time between the times t1 and t2, whereby the duration is a surrogate of the body lumen size, and optionally can specify additional values, such as respective lesion target values and acoustic energy densities. An example of such a look-up-table is shown in Table 5 below. The controller 120 can then use an equation or further look-up-table to determine the voltage level that is to be applied between electrodes of the ultrasound transducer, i.e., to determine what voltage level is needed to achieve the desired acoustic output power. It is noted that the acoustic output powers shown in Tables 4 and 5 are generalized, non-limiting examples, and that actual values of acoustic output power are dependent upon various factors in addition to body lumen diameter, such as sonication duration, frequency, transducer shaped, target depth, balloon pressure, cooling fluid flow rate, and/or the like.

TABLE 5

| Time between times t1 and t2) | Lesion Target Volume (mL) | Acoustic Output Power (W) |
|---|---|---|
| Time-a | Volume-a | Power-a |
| Time-b | Volume-b | Power-b |
| Time-c | Volume-c | Power-c |
| . | . | |
| . | . | |
| . | . | |
| Time-z | Volume-z | Power-z |

In embodiments where controller 120 uses a look-up-table, such as the one shown in Table 4 above, to select the appropriate acoustic output power, the controller 120 selects the acoustic output power based on an estimated body lumen diameter. In embodiments where controller 120 uses a look-up-table, such as the one shown in Table 5 above, to select the appropriate acoustic output power, the controller 120 selects the acoustic output power based on the time duration between times t1 and t2, which is a surrogate of an estimate of the body lumen diameter. That is, the amount of time it takes for the pressure to transition from the inflection point at time t1 (that corresponds to the point in time when there is a transition from vacuum pressure to environmental pressure) to the inflection point at time t2 (that corresponds to the point in time when the balloon becomes in apposition with the body lumen wall) is an example of a surrogate of an estimate of a body lumen size (and more specifically, diameter). Another example of a surrogate of an estimate of a body lumen size (and more specifically, diameter) is the volume of fluid in the balloon 112 when the balloon 112 becomes in apposition with the body lumen. Either fluid parameter can be detected, monitored, and/or measured to estimate the body lumen size.

In certain embodiments, the controller 120 may verify that the correct size balloon has been deployed based on deviations in the balloon pressure-time curve. For a non-compliant balloon or a balloon that does not otherwise expand the entire range of body lumen diameters (e.g., a balloon that does not expand between a diameter of 3 mm and 8 mm, the normal range of the renal artery), it may be important that the correct size balloon be used so that the balloon occludes the body lumen (to, e.g., center the transducer and/or maintain contact between the wall of the body lumen and the electrodes), but extra material causing wrinkles in the balloon does not interfere with the sonication. The controller 120 may include a look-up table in its memory that includes the expected balloon-pressure time curve for each size balloon. A larger balloon can require a higher pressure to reach a target diameter, and a smaller balloon can reach the diameter at a lower pressure. If a smaller than expected balloon is employed (e.g., a 6 mm balloon is input into the controller 120, but a 3 mm balloon is inserted into the patient instead), the balloon may never occlude the artery and the expected inflection point at t2 (indicated by a gradual increase in slope) where the balloon would be expected to occlude the body lumen may never occur. Instead, the pressure may suddenly spike (indicated by a sudden increase in slope) when the balloon becomes fully inflated at inflection point t3. The shape of the balloon-pressure curve may follow the slopes depicted in FIG. 7A. An error message may then be displayed on the user interface, and the controller 102 may prompt the user to deflate and move the catheter to a different, size appropriate location and/or remove and replace the balloon catheter.

In another example, if a larger than expected balloon size is used (e.g., a 6 mm balloon is input into the controller 120, but an 8 mm balloon is inserted into the patient instead), the required pressure to occlude the body lumen can be higher than expected. In addition, the expected inflection point at t3 (where the balloon would be fully inflated if a 6 mm balloon had been used) may be delayed. The expected duration between t1 and t3 (and/or t2 and t3) for each size balloon may be input into the controller 120. The controller 120 may set a timer at the beginning of t1 and/or t2 that may time out at the expected t3 if the inflection point on the pressure curve is undetected. An error message may then be displayed on the user interface, and the controller 102 may prompt the user to deflate and move the catheter to a different, size appropriate location and/or remove and replace the balloon catheter.

If the detected curve matches the expected curve, the controller 120 may display a message of the graphical user interface confirming the balloon size detected.

Acoustic output power is just one example of an ultrasound excitation parameter, or more generally, a treatment parameter that can be selected and used for exciting an ultrasound transducer to treat tissue that surrounds the portion of the body lumen within which the balloon 112 and the transducer 111 are inserted. Embodiments of the present technology described herein can alternatively, or additionally, be used to select other ultrasound excitation parameters besides acoustic output power. Examples of such other types of treatment parameters, include, but are not limited to, sonication duration, cooling fluid flow rate during sonication, excitation signal duty cycle, cooling time before and after sonication, balloon deflation time (the faster the balloon is deflated, the faster heat is wicked away), temperature of the cooling fluid, recommended number of ablations per body lumen. For example, a renal artery diameter of 8 mm is often associated with a renal artery length sufficient to render three or more ablations. This information may be combined with data regarding the patient's height, weight, presence of heart disease, atherosclerosis, lifestyle (e.g., diet, exercise, smoking, and sleep), blood pressure, cholesterol, presence of metabolic syndrome, family history, diabetes, kidney disease, peripheral artery disease, coronary heart disease, carotid artery disease, coronary artery calcium score, and/or other imaging information, e.g., from fluoroscopy, to provide a recommendation as to the number of sonications that should be provided. Controller 120 may determine, recommend the delivery and/or deliver the number of ablations based on the artery diameter and length to maximize the number of ablations delivered, while minimizing the number of changes in required catheter size (also referred to as a balloon size). As described further herein, a nerve probe may be used to determine that not all the planned ablations are required in order to effectively treat the patient.

In another example, where proximal renal artery branching is present, and the diameter of a renal artery branch is determined to be ≥3 mm, the controller 120 may determine that one sonication should be delivered in the branch at a location at least 5 mm from the kidney parenchyma, and at least 10 mm from adjacent arteries. In another example, where an accessory artery is present and has a treatable artery diameter≥3 mm, the controller 120 may determine that one sonication should be delivered at least one radiopaque transducer length distal to the accessory artery/aorta ostium.

Figure 9:
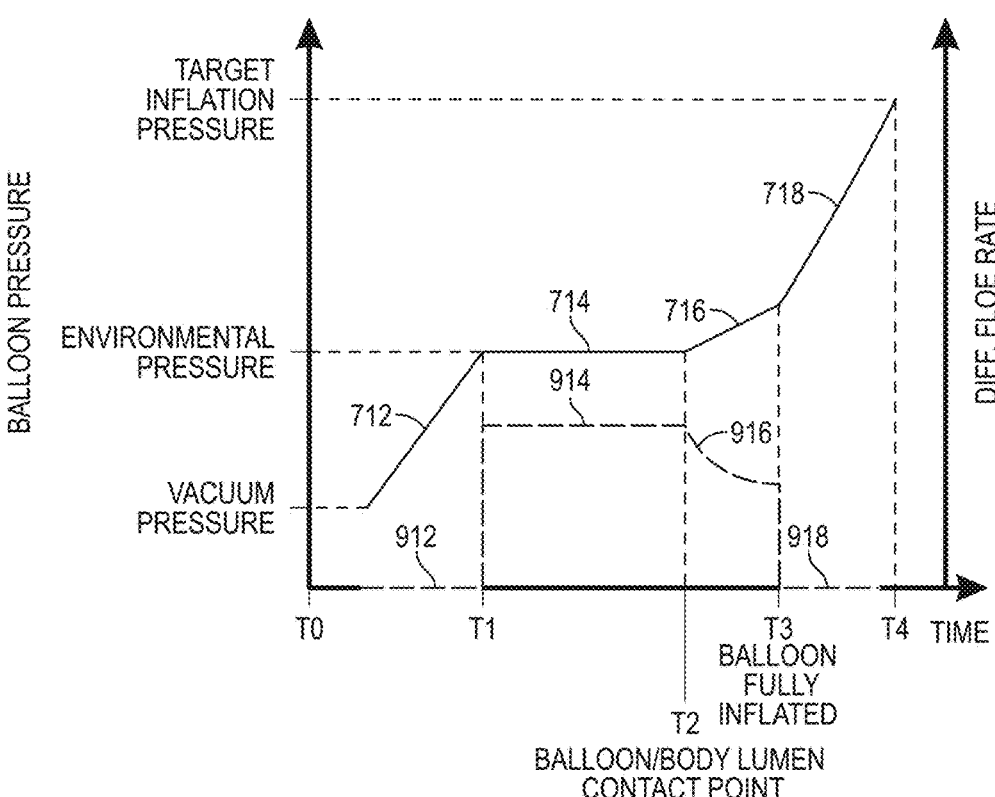
FIG. 9 illustrate an example graph of differential flow rate versus time, which is used to explain how a difference between the flow rate of fluid being provided to a balloon and being removed from the balloon changes over time as the fluid is circulated through the balloon, in accordance with an embodiment.

Instead of (or in addition to) using pressure measurements to determine an estimate of a size of a portion of the body lumen, another fluid parameter, such as flow rate measurements, can be used to determine an estimate of a size of a portion of the body lumen, or a surrogate thereof. Referring to FIG. 9, the same curve (shown in a solid line) of balloon pressure versus time that was shown in FIG. 7B discussed above is provided, but also includes an additional curve (shown in a thick dashed line) of differential flow rate versus time, wherein the differential flow rate is the difference in the flow rate of the fluid being injected into the balloon 112 (e.g., using the pressure syringe 542*a*) and the flow rate of the fluid being drawn from the balloon 112 (e.g., using the vacuum syringe 542*b*). Referring briefly back to FIG. 5, measurements of the flow rate of the fluid being injected into the balloon 112 (e.g., using the pressure syringe 542*a*) can be measured using the flow rate sensor F1, and the flow rate of the fluid being drawn from the balloon 112 (e.g., using the vacuum syringe 542*b*) can be measured using the flow rate sensor F2. The differential flow rate at any given time can be determined, e.g., by subtracting a flow rate measurement obtained using the flow rate sensor F1 from a flow rate measurement obtained using the flow rate sensor F2. Referring to the differential flow rate curve in FIG. 9, the portion of the curve labeled 912 corresponds to the period of time (between times t0 and t1) during which the pressure within the balloon is increasing, without the volume of the balloon increasing, until the pressure in the balloon reaches environmental pressure (at time t1). During this period of time (between times t0 and t1) the rate of flow of the fluid being removed from the balloon 112 (as measured using the flow rate sensor F2) is the same as the rate of flow of the fluid being injected into the balloon (as measured using the flow rate sensor F1), which means the differential flow rate is substantially zero, which is why the portion of the curve labeled 912 has a substantially zero or no slope. Starting at time t1, when the pressure in the balloon reaches environmental pressure, the flow rate of the fluid being injected in the balloon 112 can become greater than the flow rate of the fluid being removed from the balloon 112, causing there to be positive differential flow rate, as represented by the portion of the curve labeled 914. This differential flow rate can remain about the same until the balloon becomes in apposition with the body lumen at time t2. Starting at time t2, because expansion of the balloon 112 is being resisted by the body lumen, the flow rate of the fluid being injected into the balloon 112 can be reduced while the flow rate of the fluid being removed from the balloon 112 remains the same, resulting in the differential flow rate being reduced, as represented by the portion of the curve labeled 916. At the point in time that the balloon becomes fully inflated, at time t3, the differential flow rate can return to being substantially zero, as represented by the portion of the curve labeled 918. The curve in FIG. 9 that is shown in the thick dashed line is an example of a differential flow rate curve for a noncompliant balloon. The curve can look a little different for a compliant balloon, but there can still be an inflect point (at time t2) that can be identified in a differential flow rate curve for a compliant balloon.

The controller 120, or some other device, can use the measures of flow rate to estimate the volume of the balloon when the balloon 112 becomes in apposition with the body lumen, and such an estimate of the volume can be used to determine an estimate of the body lumen size, or a surrogate thereof, either of which can be used to select an ultrasound treatment parameter that can be selected and used for exciting the ultrasound transducer 111 to treat tissue that surrounds the portion of the body lumen within which the balloon 112 and the transducer 111 are inserted. For example, a look-up-table similar to Table 4 shown and discussed above, can be used to select an appropriate acoustic output power and/or another ultrasound treatment parameter.

In accordance with certain embodiments of the present technology, the controller 120 identifies the inflection points in the differential flow rate versus time curve (shown in the thick dashed curve in FIG. 9) that corresponds to the times t1 and t2, so that the length of time (also referred to as a duration) corresponding to the substantially flat portion of the curve 914 can be determined. The duration between times t1 and t2 can be determined by determining a difference between the times t2 and t1. Alternatively, the controller 120 can start a timer when the inflection point at time t1 is identified and can stop the timer when the inflection point at time t2 is identified, in which case the duration would be the value of the time when the timer is stopped. Other ways for determining the duration of time between the times t1 and t2 are also possible and within the scope of the present technology. Once the time duration is determined, a look-up-table similar to Table 5 shown and discussed above, can be used to select an appropriate acoustic output power and/or another ultrasound treatment parameter.

In some of the above described embodiments, a change in balloon pressure or a change in differential flow rate of fluid being provided to and removed from the balloon were used to determine an estimate of a body lumen size, or a surrogate thereof, which in turn was used to select one or more ultrasound treatment parameters. Further, in some of the above described embodiments, the pressure and the flow rate sensors that were used were shown and described as being part of the cooling fluid supply subsystem 630, or more specifically, part of the cartridge 130. The pressure sensors and/or flow rate sensors can alternatively be part of the catheter 102, e.g., by being included within or adjacent to the fluid lumens 270 and/or 272.

In still other embodiments, one or more sensors can be located on a distal portion of a guide sheath that is used to insert the distal portion of the catheter 102, which includes the balloon 112 and the transducer 111, into a portion of a body lumen. In such an embodiment, one of more sensors on the distal portion of the guide sheath can be used to determine when the balloon 112 becomes in apposition with the body lumen. The volume in the balloon at that point in time, or the duration of time that it took to get to that point in time, can then be used to determine an estimate of the body lumen size, or a surrogate thereof. For example, a pressure sensor can be located at the distal end of a guide sheath that is used to insert the distal portion of the catheter 102 into a portion of a body lumen. Presuming the body lumen is an artery (e.g., a renal artery) that is providing blood from the heart to some other organ (e.g., a kidney) or region of the body, then such a pressure sensor can be used to monitor the blood pressure proximate to (i.e., upstream of) the balloon 112 and transducer 111, and can be used to detect when the balloon 112 becomes in apposition with the body lumen. This is because when the balloon 112 becomes in apposition with the body lumen, the balloon 112 can begin to block blood from flowing past the balloon 112, thereby causing the blood pressure upstream of the balloon 112 (as sensed by the pressure sensor located on a distal portion of the guide sheath) to rapidly increase so that a corresponding inflection point in a pressure versus time curve can be identified. If the body lumen were instead a vein that is providing blood back to the heart, then the blood pressure sensed by a pressure sensor on a distal portion of a guide sheath should instead rapidly decrease when the balloon 112 becomes in apposition with the body lumen, such that a corresponding inflection point in a pressure versus time curve can be identified.

For another example, a flow rate sensor can be located at the distal end of a guide sheath that is used to insert the distal portion of the catheter 102 (which includes the balloon 112 and the transducer 111) into a portion of a body lumen. Presuming the body lumen is an artery (e.g., a renal artery) that is providing blood from the heart to some other organ (e.g., a kidney) or region of the body, then such a blood flow sensor can be used to monitor the blood pressure proximate to (i.e., upstream of) the balloon 112 and transducer 111, and can be used to detect when the balloon 112 becomes in apposition with the body lumen. This is because when the balloon 112 becomes in apposition with the body lumen, the balloon 112 can begin to block blood from flowing past the balloon 112, thereby causing the blood flow rate upstream of the balloon 112 (as sensed by the flow rate sensor located on a distal portion of the guide sheath) to rapidly decrease so that a corresponding inflection point in a blood flow rate versus time curve can be identified.

Instead of placing a pressure sensor and/or a flow rate sensor on a distal portion of a guide sheath, which enables blood pressure and/or blood flow rate to be monitored proximal the balloon 112 and transducer 111, a pressure sensor and/or a flow rate sensor can instead by located on a distal portion of a guidewire, which would enable blood pressure and/or blood flow at the proximal side of the balloon 112 to be monitored. Such a sensor can similarly be used to detect when the balloon 112 comes into apposition with the body lumen. If a pressure sensor is on the distal portion of the guidewire, and the body lumen is an artery (e.g., a renal artery) that is providing blood from the heart to some other organ (e.g., a kidney) or region of the body, then such a pressure sensor can be used to monitor the blood pressure distal (i.e., downstream of) the balloon 112 and transducer 111, and can be used to detect when the balloon 112 becomes in apposition with the body lumen. This is because when the balloon 112 becomes in apposition with the body lumen, the balloon 112 can begin to block blood from flowing past the balloon 112, thereby causing the blood pressure downstream of the balloon 112 (as sensed by the pressure sensor located on a distal portion of the guidewire) to rapidly decrease so that a corresponding inflection point in a pressure versus time curve can be identified.

If a flow rate sensor is on the distal portion of the guidewire, and the body lumen is an artery that is bringing blood to an organ, then such a flow rate sensor can be used to monitor the blood flow rate sensor distal the balloon 112 and transducer 111, and can be used to detect when the balloon 112 becomes in apposition with the body lumen. This is because the blood flow rate at a distal portion of the guidewire, which is distal the balloon, should also rapidly decrease when the balloon 112 becomes in apposition with the body lumen, such that a corresponding inflection point in a flow rate versus time curve can be identified.

Other types of sensors besides pressure sensors and flow rate sensors can alternatively, or additionally, be used to detect when the balloon 112 becomes in apposition with a body lumen. For example, an accelerometer, a microphone, and/or a hydrophone that is located on a distal portion of a guide sheath or a distal portion of a guidewire can detect a change in blood flow (i.e., changes in the sound of the blood flow) that occurs when the balloon 112 becomes in apposition with a body lumen, because measurements obtained by such alternative types of sensors should similarly rapidly increase or decrease, depending on the type of sensor and where the sensor is located, when the balloon 112 becomes in apposition with a body lumen. It would also be possible to use the transducer 111 itself as a microphone type of sensor, where the transducer is made of a piezoelectric material. In certain embodiments, transducer 111 is optimized to improve its audio response. For example, transducer 111 may be used as a hydrophone and system 100 may include a preamplifier as close to transducer 111 as possible to improve the signal to noise ratio. In certain embodiments, a preamplifier is located on the proximal portion 220 of the catheter 102, e.g., adjacent to electrical coupling(s) 232. One of ordinary skill in the art reading this disclosure would appreciate that still other types of force sensors can additionally or alternatively be used to detect when the balloon 112 becomes in apposition with a body lumen, which are also within the scope of the embodiments described herein.

Figure 10:
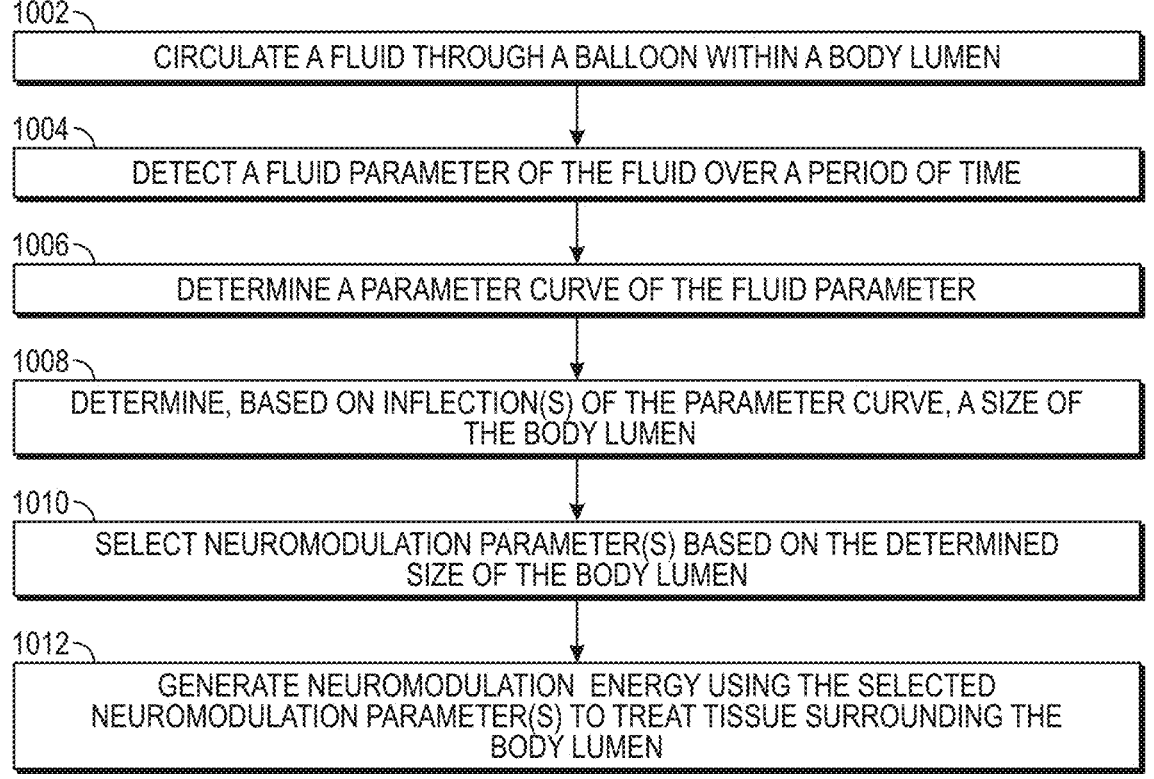
FIG. 10 is a flowchart of a method of sizing a body lumen, in accordance with an embodiment.

The flowchart of FIG. 10 will now be used to summarize various methods of the present technology that are used to estimate a size of a portion of a body lumen, or surrogate thereof, to thereby select one or more ultrasound treatment parameters for use in treating tissue that surrounds the portion of the body lumen. Such methods are for use with a tissue treatment system (e.g., 100) that comprises a catheter (e.g., 102) including a catheter shaft (e.g., 214) having a distal end and a proximal end, first and second lumens (e.g., 270, 272) extending longitudinally through the catheter shaft between the distal and the proximal ends thereof, an ultrasound transducer (e.g., 111) distally positioned relative to the distal end of the catheter shaft, a balloon (e.g., 112) surrounding the ultrasound transducer, and a fluid supply subsystem (e.g., 110 and 130, or 630), wherein the first lumen is configured to provide cooling fluid (e.g., 213) from the fluid supply subsystem to the balloon, and the second lumen is configured to return cooling fluid from the balloon to the fluid supply subsystem.

Referring to FIG. 10, at operation 1002, a cooling fluid is circulated through the balloon within the body lumen. The operation involves inflating the balloon using the cooling fluid, while the ultrasound transducer and the balloon are inserted into a portion of the body lumen, e.g., a renal artery. Alternatively, the body lumen can be a hepatic artery, a splenic artery, a celiac trunk, a superior mesenteric artery, or an inferior mesenteric artery, but is not limited thereto. Prior to operation 1002, a guide sheath and/or a guidewire may be used to guide the distal portion of the catheter shaft and the transducer and the balloon into the portion of the body lumen, as is known in the art.

Still referring to FIG. 10, at operation 1004, a fluid parameter of the cooling fluid is detected over a period of time. For example, while the balloon is being inflated, one or more sensors is/are used to produce sensor measurements indicative of the flow parameter of the cooling fluid being supplied to the balloon and/or being removed from the balloon. The flow parameter may be a pressure of the cooling fluid. Alternatively, the flow parameter may be a flow rate of the cooling fluid. For example, the flow rate can be a differential flow rate, which is a difference an injection flow rate of cooling fluid being injected into the balloon and a withdrawal flow rate of the cooling fluid being withdrawn from the balloon.

Referring briefly back to FIG. 5, the pressure sensor P1 is an example of a sensor that can be used to produce sensor measurements indicative of the pressure of the cooling fluid being supplied to the balloon 112, and the pressure sensor P2 is an example of a sensor that can be used to produce sensor measurements indicative of the pressure of the cooling fluid being removed from the balloon 112. Still referring briefly back to FIG. 5, the flow rate sensor F1 is an example of a sensor that can be used to produce sensor measurements indicative of the flow rate of the cooling fluid being supplied to the balloon 112, and the flow rate sensor F2 is an example of a sensor that can be used to produce sensor measurements indicative of the flow rate of the cooling fluid being removed from the balloon 112.

Alternatively, at operation 1004, while the balloon is being inflated, one or more sensors is/are used to produce sensor measurements indicative of pressure and/or flow rate of blood within the body lumen in which the ultrasound transducer and the balloon are inserted. Such a sensor can be a pressure sensor located on a distal portion of a guide sheath, a flow rate sensor located on a distal portion of a guidewire, a flow rate sensor located on a distal portion of a guide sheath, or a flow rate sensor located on a distal portion of a guidewire. In still other embodiments, operation 1004 can be performed using an accelerometer, microphone, or hydrophone type of sensor that produces sensor measurements indicative of blood flow. Such an accelerometer, microphone, and/or hydrophone can be located on a distal portion of a guide sheath or a guidewire. As noted above, it would also be possible for the piezoelectric transducer body of the ultrasound transducer 111 within the balloon 112 to be used as a microphone.

Referring again to FIG. 10, operation 1006 involves determining a parameter curve of the fluid parameter. The parameter curve can include the fluid parameter versus an independent variable over a period of time. For example, the independent variable can be time. Alternatively, the independent variable may be a volume of the circulated cooling fluid that is delivered to the balloon.

As described above, the parameter curve can include several inflections corresponding to changes in the fluid parameter. For example, an inflection in the parameter curve, such as those shown in FIGS. 7A-9, can correspond to a change in the change of pressure of the cooling fluid at a particular point in time (or at a particular inflation volume).

At operation 1008, a size of the body lumen is determined based on the parameter curve. The determination of body lumen size may be based on one or more inflections of the curve. For example, the analysis of the parameter curves described above can be used. In an embodiment, the parameter curve includes a minimal slope segment between a first inflection, e.g., at t1, and a second inflection, e.g., at t2. Determining the size of the body lumen can be based on a duration between the first inflection and the second inflection. For example, the time between the inflections, or the volume flowed through the balloon during that time, can be used to determine the balloon size (and thus, the vessel size) when the second inflection occurs.

As described above, the inflections can include a third inflection after the second inflection, e.g., at t3. Determining the size of the body lumen can be based on at least a portion of a duration between the second inflection and the third inflection. For example, the time between the first inflection and the third inflection, or the volume flowed through the balloon during that time, can be used to determine the balloon size (and thus, the vessel size). In an embodiment, the parameter curve includes a first slope between the first inflection and the second inflection, and a second slope between the second inflection and the third inflection. The determination can include detecting the second inflection, e.g., at t2, by determining that the second slope is greater than the first slope.

Using the techniques described above, the system determines, based on one or more of the sensor measurements, when the balloon is sufficiently inflated such that the balloon becomes in apposition with the portion of the body lumen. Details of how operation 1008 can be performed, according to various embodiments of the present technology, were discussed above with reference to FIGS. 7B, 8, and 9. For example, operation 1008 can include determining, based on pressure measurements, when the inflection point at the variable time t2 occurs in FIG. 7B or FIG. 8. For another example, operation 1008 can include determining, based on flow rate measurements of fluid being injected into the balloon 112, when the inflection point at the variable time t2 occurs in FIG. 9. Operation 1008 can alternately include using a pressure sensor, flow rate sensor, accelerometer, microphone and/or hydrophone to detect when blood pressure and/or blood flow in the body lumen rapidly increases or decreases due to the balloon becoming in apposition with the portion of the body lumen and stopping blood in the body lumen from flowing past the balloon, as was described in additional detail above.

Referring again to FIG. 10, operation 1008 involves determining an estimate of a size of the portion of the body lumen, or a surrogate thereof, based on sensor measurement(s) obtained when the balloon is sufficiently inflated such that the balloon becomes in apposition with the body lumen, or based on an amount of time it took for the balloon to change from atmospheric pressure to a pressure that is sufficient for the balloon to become apposed to the body lumen, e.g., a duration between times t1 and t2 in FIGS. 7B and 8. As explained above, operation 1008 can include, for example, determining an estimate of a volume of the balloon when the balloon is sufficiently inflated such that the balloon becomes in apposition with the body lumen, and determining the estimate of the size of the portion of the body lumen (or a surrogate thereof), based on the estimate of the volume of the balloon when the balloon is sufficiently inflated such that the balloon becomes in apposition with the body lumen. More specifically, based on the estimate of the volume of the balloon (when the balloon is sufficiently inflated such that the balloon becomes in apposition with the body lumen), an estimate of the diameter of the balloon at that point in time can be determined, and it can be presumed that the diameter of the balloon at that point in time is the same as the inner diameter of the portion of the body lumen in which the balloon is inserted. Alternatively, or additionally, operation 1008 can involve determining the estimate of the size of the portion of the body lumen (or a surrogate thereof), based on the amount of time it took for the balloon to be sufficiently inflated such that the balloon becomes in apposition with the body lumen. Indeed, in certain embodiments, the amount of time (it took for the balloon to be sufficiently inflated such that the balloon becomes in apposition with the body lumen) is itself the surrogate of the estimate of the size of the portion of the body lumen, and can be used to select one or more treatment parameters. Additional and alternative details of operation 1008 can be appreciated from the above discussion of FIGS. 7B, 8, and 9.

Optionally, the operation of determining the size of the body lumen may be in response to a determination of a type of balloon that is being used. For example, the balloon sizing technique may include determining whether the balloon is a non-compliant balloon or a compliant balloon, and then determining the size of the body lumen based on such determination. In an embodiment, when the balloon is determined to be a non-compliant balloon, e.g., based on a user input to the tissue treatment system, then the sizing can rely on curves such as those shown in FIGS. 7A-7B to determine the body lumen size. Alternatively, when the balloon is determined to be a compliant balloon, then the sizing can rely on curves such as the curve of FIG. 8 to determine the body lumen size. The determination of balloon type may also lead to the selection of other sizing techniques such as those described below with respect to FIGS. 19A-20.

Referring again to FIG. 10, at operation 1010, a neuromodulation parameter is selected based on the size of the body lumen. For example, at least one ultrasound treatment parameter for use in treating tissue surrounding the portion of the body lumen may be selected based on the estimate of the size of the portion of the body lumen, or the surrogate thereof. In certain embodiments, an acoustic output power is selected at operation 1010. Alternatively, or additionally, other types of ultrasound treatment parameters can be selected at operation 1010, including, but not limited to, sonication duration, cooling fluid flow rate during sonication, and/or excitation signal duty cycle.

It will be appreciated that the selection of the neuromodulation parameter may be performed directly as a determination at operation 1008. More particularly, rather than first estimating a size of the body lumen and then selecting the parameter based on the size, the neuromodulation parameter can be determined directly based on the inflection(s). For example, the duration between inflections can be correlated to neuromodulation parameters in a lookup table that is referenced to go directly from the sensor measurements of the inflections and associated time points to the neuromodulation parameters. Accordingly, the selection of the neuromodulation parameter as a secondary operation of estimating the body lumen size is illustrative and not limiting.

At operation 1012, neuromodulation energy is generated based on the neuromodulation parameter. The selected neuromodulation parameter is used to generate the neuromodulation energy to treat the tissue surrounding the body lumen. Generation of the neuromodulation energy involves exciting the ultrasound transducer, using the at least one ultrasound treatment parameter. In certain embodiments of the present technology, some or all of the operations summarized above with reference to FIG. 10 are performed fully- or semi-autonomously by the controller 120. Additional details of the methods summarized with reference to FIG. 10 could be appreciated by the above discussion of FIGS. 1-9.

In accordance with certain embodiments, the controller 120 and/or catheter 102 may be configured to actuate one or more blood flow sound sensors, e.g., upon delivery of a guidewire (e.g., 216) or a dedicated blood flow sound sensor wire into a body lumen, upon delivery of the distal end of the catheter 102 into a body lumen, upon the initiation of balloon inflation, upon the completion of balloon inflation, before an ablation, e.g., renal denervation, and/or after a programmed duration (e.g., after about 7 seconds of ablation of renal arteries).

In certain embodiments, one or more blood flow sound measurements is/are taken prior to inserting the catheter 102 into a body lumen and/or prior to inflating the balloon 112 around the transducer 111 using a blood flow sensor on the guidewire 216 or a dedicated sensor wire in order to determine the size of body lumen by analyzing the blood flow sound signals. In certain embodiments, the system may then use a look-up-table of a programmable logic block stored within memory 614 of the controller 120 or catheter 102, e.g., within erasable programmable read-only memory (EEPROM), wherein the programmable logic block is configured to select, in accordance with the inputted blood flow sound signals, a body lumen diameter, or a surrogate thereof. The system may further use the look-up-table or a separate look-up-table of a programmable logic block stored within memory of the controller or catheter, e.g., within erasable programmable read-only memory (EEPROM), wherein the programmable logic block is configured to select, in accordance with the inputted body lumen diameter a power, frequency, and/or duration settings of the catheter according to the body lumen diameter. Larger diameter body lumens normally require higher power setting. The system may further use this information to determine and communicate (e.g., on a graphic user interface and/or audio device) the size of a balloon, cooling fluid flow rate, balloon pressure, and/or balloon inflation diameter indicated according to a look-up-table that correlated body lumen diameter with required balloon requirements prior to inserting the catheter into body lumen and/or prior to inflating the balloon. After insertion of the catheter 102, the system 100 may measure blood flow sound to determine whether the transducer 111 is properly centered in the body lumen. When the transducer 111 is off-center, the blood flow sound may be altered in a range of ways compared to when the transducer 111 is centered. This range may also be affected by body lumen diameter. The system may use a look-up-table to correlate blood flow sound measurements with the angle of the transducer 111 and/or body lumen diameter and communicate (e.g., on a graphic user interface and/or audio device) required adjustments to the catheter 102 placement within body lumen accordingly. Also, after the catheter insertion, e.g., after the transducer 111 is centered, in certain embodiments, the ultrasound system 100 may then take blood flow sound measurements during inflation of a balloon (e.g., 112) to detect apposition within (e.g., occlusion) body lumen in order to more safely inflate the balloon 112, ensure adequate contact with body lumen for more efficient and even cooling on body lumen, and decrease the complexity of the procedure.

In certain embodiments, a patient's blood pressure measurement is entered into the memory of the controller 120. A timer is initiated when the balloon 112 is at a known pressure, e.g., a vacuum pressure (time t0), whereupon the controller begins to inflate the balloon 112. A sensor, e.g., accelerometer, hydrophone, and/or microphone, configured to detect blood flow sound is used to determine when the balloon is in apposition with the body lumen (time t2). In certain embodiments, the memory of controller 120 includes a look-up-table that correlated the time it takes for balloon 112 to go from the known pressure (e.g., pressure vacuum) at t0 to environmental pressure (t1) using the inputted patient's blood pressure. Controller 120 then subtracts the time between t0 to t1 from time t0 to t2 to determine the time between t1 and t2 and uses the time between t1 and t2 to determine an estimate of a size of the portion of the body lumen, or a surrogate thereof, the controller then displays on the user interface, the estimated size of the portion of the body lumen, or the surrogate thereof.

In certain embodiments, a sensor, e.g., accelerometer, hydrophone, and/or microphone, configured to detect the inflection point at t1, where the balloon begins to change from environmental pressure to an expanded state, by detecting the sound balloon 112 makes when it begins to expand and/or a change in the sound of blood flow when the balloon begins to expand. The sensor then detects time t2, when the balloon is in apposition with the body lumen by detecting the absence of the sound of blood flow at a point distal to the balloon. The controller may then use the time between t1 and t2 to determine an estimate of a size of the portion of the body lumen, or a surrogate thereof. The controller then displays on the user interface, the estimated size of the portion of the body lumen, or the surrogate thereof.

In certain embodiments, a sensor, e.g., accelerometer, hydrophone, and/or microphone, may be further configured to detect the inflection point at t3, where the non-compliant balloon is fully inflated, by detecting the sound balloon 112 makes when it stops expanding. In certain embodiments, this information is displayed on the user interface. In certain embodiments, t3 can be used to confirm that the body lumen measurement (determined by any of the methods described herein including by using balloon pressure, cooling fluid rate, or a sensor) is correct. For example, a look-up table may correlate a body lumen diameter with the time it should take for the balloon to fully inflate (e.g., at a given patient blood pressure) at a given cooling fluid flow rate.

In certain balloonless catheter embodiments, the body lumen diameter, or a surrogate thereof, may be measured before and/or after insertion catheter 102 in order to automatically program catheter 102 with appropriate parameters according to body lumen size with one or more blood flow sound sensors on, e.g., a dedicated blood flow sensor wire, guidewire 216, or catheter 102, etc.

In certain embodiments, the system may additionally or instead use blood flow sound sensor measurements to determine denervation, e.g., renal denervation, status. Without prejudice or limitation, it is theorized that change in blood flow rate sound in the renal artery resulting from the ablation is indicative of the efficacy of the renal denervation procedure.

An accelerometer may indicate a patient's physical activities and heart sounds in addition to blood flow sounds. A microphone may indicate heart sounds and environmental sounds of, e.g., the operating room noises and communication, in addition to the blood flow sounds. In certain embodiments, measurements taken at different times and/or with different blood flow sensors can be averaged and/or compared, such as to, e.g., filter out noise in the measurements and/or to provide more accurate measurements. For example, one or more baseline measurements may be taken using a blood flow sound sensor on the guidewire 216 or a dedicated sensor wire prior to inserting the catheter 102 into a body lumen, and/or by using a blood flow sensor on catheter 102 prior to balloon inflation, in order to filter out noise (e.g., patient activity, heart sounds, etc.). One of the sensors could be used to detect ambient conditions which could be used to subtract out common mode noise of a sensor closer to the target area.

The controller 120 and/or catheter 102 can be configured to control the operational mode of the catheter 102 using, for example, information from the blood flow sound sensor or other physiologic information. In certain examples, the system 100 can include a physiologic sensor, such as a respiration sensor, an activity sensor, a posture sensor, an electrocardiogram (ECG) sensor, an impedance sensor, etc. Such a physiologic sensor can be configured to provide physiologic information from the patient to controller 120 and/or catheter, for example, to filter out noise from the system. In certain embodiments, the controller 120 and/or catheter 102 are configured to screen blood flow sound signals to exclude values resulted from measurements performed when a background noise level exceeds a predetermined threshold. In one embodiment, a noise monitoring module measures the background noise level. In certain embodiments, a noise monitoring module may include an activity sensor that senses a patient's physical activities and an activity sensor interface module to convert the physical activities to the background noise level. In another specific embodiment, noise monitoring module includes further sensor interface modules coupled to blood flow sound sensor, which sense the patient's physical activities and the patient's cardiac mechanical activities, in addition to the acoustic energy related to blood flow sound. When blood flow sound sensor includes an accelerometer, the further sensor interface module includes an activity level detector to produce the background noise level signal indicative of the patient's physical activities. The activity level as indicated by the blood flow sound sensor signal has a distinctively higher amplitude than the blood flow sounds. Heart sounds as indicated by the blood flow sound sensor signal has a distinctively lower amplitude than the blood flow sounds. Thus, the activity level detector distinguishes the patient's physical activities and heart sounds from the blood flow sounds by using predetermined activity level and heart sound thresholds. In one embodiment, parameter generator includes a memory circuit to store the parameter values generated by measurement module. In another embodiment, memory stores only parameters screened by screening module.

Use of Ultrasound Transducer to Estimate Body Lumen Size

Figure 11A:
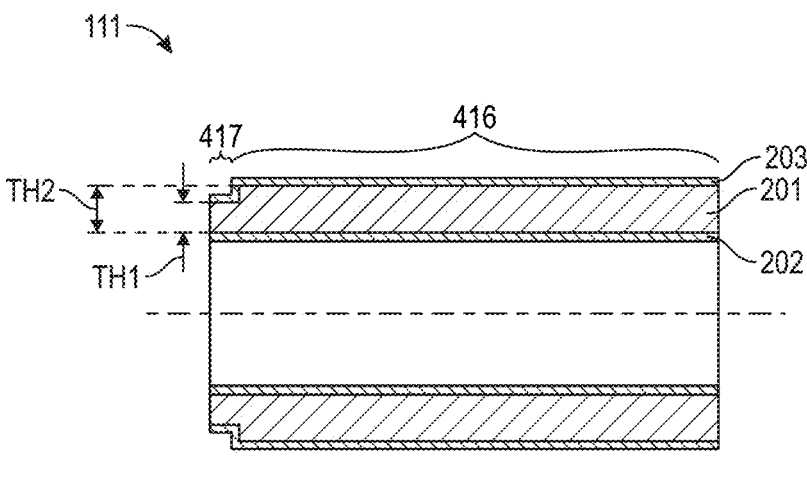
FIG. 11A is a longitudinal cross-sectional view of an ultrasound transducer having a single stepped segment, in accordance with an embodiment.

FIG. 11A is a longitudinal (also referred to as a axial) cross-sectional view of the ultrasound transducer 111 having a single stepped segment, according to certain embodiments of the present technology, wherein the ultrasound transducer 111 has a piezoelectric transducer body 201 and a pair of electrodes 202 and 203. More specifically, in the embodiment shown in FIG. 11A, the piezoelectric transducer body 201 comprises a hollow tube of piezoelectric material having an inner surface and an outer surface, with the inner electrode 202 is disposed on the inner surface of the hollow tube of piezoelectric material, and the outer electrode 203 is disposed on the outer surface of the hollow tube of piezoelectric material. In such embodiments, the hollow tube of piezoelectric material is an example of a piezoelectric transducer body 201. In FIG. 11A, and other figures, the hollow tube of piezoelectric material, or more generally the piezoelectric transducer body 201, is cylindrically shaped and has a circular radial cross-section. However, in alternative embodiments the hollow tube of piezoelectric material can have other shapes besides being cylindrical with a circular radial cross-section. Other cross-sectional shapes for the hollow tube of piezoelectric material, and more generally the piezoelectric transducer body 201, include, but are not limited to, an oval or elliptical cross-section, a square or rectangular cross-section, pentagonal cross-section, a hexagonal cross-section, a heptagonal cross-section, an octagonal cross-section, and/or the like. It is also possible for the transducer to not be hollow and to have various other shapes than those specifically described herein. Unless stated otherwise, it will be assumed for the following discussion that the piezoelectric transducer body 201 is cylindrically shaped and has a circular radial cross-section. The electrodes 202, 203 of the transducer 111 can also be referred to more generally as first and second electrodes, or a pair of electrodes.

The hollow tube of piezoelectric material, and more generally the piezoelectric transducer body 201, can be made from various piezoelectric materials, such as, but not limited to, lead zirconate titanate (PZT), piezoelectric single crystals or other piezoelectric ceramic materials. Other technologies such as piezoelectric Micromachined Ultrasonic Transducers (pMUT) and capacitive Micromachined Ultrasonic Transducers (cMUT) can also be used to construct such therapeutic devices. As depicted in FIG. 11A, the transducer 111 includes a stepped portion 417 and a non-stepped portion 416 (both of which are also shown in FIGS. 4A and 4B), wherein the non-stepped portion 416 can also be referred to as the main portion (or the medial segment given that it is between a pair of end segments) of the transducer 111. In certain embodiments, the stepped portion 417 on the proximal end of the transducer 111 allows for attachment of the electrical cabling 282, e.g., via parallel wires (e.g., 482a and 482b in FIGS. 4A and 4B), that delivers energy to the transducer 111. Such a stepped portion 417 can be incorporated into any of the transducers described herein. It would also be possible for both the proximal and distal ends of a transducer to include a stepped portion (the same as or similar to 417), which embodiments can be referred to as dual stepped embodiments. A dual stepped embodiment may advantageously provide a more uniform sonication, while also providing the system with a means of measuring artery diameter. In certain embodiments, stepped portions of the dual-stepped embodiments have a circular shape and are constructed of PZT, Piezoelectric micromachined ultrasound transducer (PMUT) or capacitive micromachined ultrasonic transducer (CMUT) so as to enable the stepped portions to measure the diameter of the body lumen, e.g., the renal artery.

In some embodiments, the stepped portion 417 can be fabricated or otherwise manufactured by machining and/or grinding away a proximal portion of the outer diameter of the piezoelectric tube. Such a step can include a uniform or constant outer diameter; however, in other embodiments, the stepped portion comprises a non-flat (e.g., rounded, curved, sloped, etc.) or irregular profile, as desired or required. In other embodiments, the stepped portion 417 can be fabricated or otherwise created by manufacturing the cylindrical tube as a single piece of material with the step integrated into the tube during formation (e.g., by casting or molding the step into the original design). In yet another embodiment, the cylindrical tube with the stepped portion can be created as two separate components (e.g., one with a larger diameter and one with the step diameter) which are bonded together (e.g., by welds, adhesives, rivets, screws, threaded couplings or features on the tube itself, press-fit connections, other mechanical or non-mechanical features, etc.). Additional details of how ultrasound transducers can be manufactured to include one or more stepped portions, and how electrical wires can be attached to a stepped portion, are disclosed in U.S. Pat. No. 10,456,605 to Taylor et al., titled "Ultrasound-based neuromodulation system," which is incorporated herein by reference. In certain embodiments, the axial length of the stepped portion 417 is about 0.4 mm and the axial length of a non-stepped (also referred to as a main) portion 416 is about 6 mm. In certain embodiments, the non-stepped (also referred to as a main) portion 416 of the transducer 111 is the portion of the transducer that produces the bulk of the ultrasonic energy delivered from the catheter 102.

Still referring to FIG. 11A, the main (also referred to as a non-stepped) portion 416 of the piezoelectric transducer body 201 (or more generally, the transducer 111) has a thickness of TH2, and the thickness of the stepped portion 417 has a thickness of TH1, wherein TH1 is less than TH2. The resonance frequency of an ultrasound transducer (or a portion thereof), such as the transducer 111 (or a portion thereof), is inversely proportional to the thickness of the piezoelectric transducer body 201 (or a portion thereof). Stated another way, the thickness of the piezoelectric transducer body 201 is proportional to the inverse of the central wavelength of the transducer. Accordingly, the thinner the piezoelectric transducer body 201 (or a portion thereof), the higher its resonance frequency. Thus, it should be appreciated that the resonance frequency of the stepped portion 417 of the transducer 111 is higher than the resonance frequency of the non-stepped (also referred to as a main) portion 416. For example, the thickness TH2 can be about 0.50 mm, and the thickness of TH1 can be about 0.23 mm. The terms "about" and "substantially", when used herein prior to a value, means plus or minus 10% of that value.

In an example embodiment, the thickness TH2 of the main (also referred to as a non-stepped) portion 416 of the transducer 111 is designed such that it has a resonance frequency of 9 MHz, and the thickness TH1 of the stepped portion 417 of the transducer 111 is designed such that it has a resonance frequency of 20 MHz. With such a transducer 111, the main portion 416 of the transducer 111 is most efficient when actuated at 9 MHz and the stepped portion 417 of the transducer 111 has a highest round-trip sensitivity at a 20 MHz frequency.

Explained another way, the main portion 416 of the transducer 111 can be configured to have a first characteristic frequency response such that when it is pinged with a broadband pulse it emits ultrasound energy at 9 MHz, and a stepped portion 417 of the transducer 111 can be configured to have a second characteristic frequency response such that when it is pinged with the broadband pulse it emits ultrasound energy at 20 MHz. If such a transducer 111 is excited with a 9 MHz signal, then the main portion 416 of the transducer 111 can emit ultrasound energy at 9 MHz, but the stepped portion can have essentially no response. Similarly, if the transducer is excited with a 20 MHz signal, then the stepped portion 417 of the transducer 111 can emit ultrasound energy at 20 MHz, but the main portion 416 can have essentially no response. In this manner, different portions of the transducer 111 can be selectively activated or excited by applying different excitation signals having different frequencies. The use of other thicknesses and frequencies are also within the scope of the embodiments of the present technology described herein.

It will be appreciated that the center frequency of different segments of the transducer 111 can be formed differently. For example, in addition to thickness differences, segments of the transducer 111 can have different core or backing materials that can affect the frequency. For example, the transducer 111 can be formed with a constant thickness over the transducer length, however, changing a position of a post within the transducer or a material backing the transducer, e.g., from an open, water-occupied space to a tungsten filled space, can reduce the frequency by half.

In accordance with certain embodiments, the mechanical quality factor Q of the main portion 416 of the transducer 111 is high to make it efficient for transmitting. The high Q may, however, be less desirable when used as a sensor resolving objects spatially due to the low bandwidth. By contrast, the Q of the stepped portion 417 of the transducer 111 is designed to be relatively low (compared to the Q for the main portion 416), which results in the stepped portion 417 having a relatively wide bandwidth to provide good axial resolution. For a specific example, the stepped portion 417 can be designed to have a center frequency response of 20 MHz, with a bandwidth of 10 MHz, such that the stepped portion 417 can receive return signals (also referred to as a echoes) between 15 MHz and 25 MHz, which provides for good resolution to enable objects in the radial direction to be discriminated between when the stepped portion 417 is being used to emit pulses and receive echoes thereof due to the pulses being reflected from an object, such as a wall of a portion of a body lumen. A duration of the emitted pulse (in the time domain) can be selected to provide for a desired bandwidth (in the frequency domain), wherein the shorter the emitted pulse (in the time domain) the higher the bandwidth (in the frequency domain). For an example, an emitted pulse that includes two cycles of a 20 MHz ultrasound signal can provide for a bandwidth of 10 MHz, which enables differentiation of objects that are about 80 micrometers (μm) apart.

In accordance with certain embodiments, an estimate of the body lumen diameter can be determined using the equation: radial distance=(measured delay*speed of sound in a medium)/2, where the radial distance is the distance between the transducer 111 and the inner wall of the body lumen in which the transducer 111 is inserted, the delay is the time that it took for an emitted ultrasound pulse to be reflected back from the inner wall of the body lumen and received by the transducer 111, the speed of sound in water is about 1500 m/sec, and in blood is about 1570 m/sec, and the factor of 2 in the denominator is included because the measured delay is the roundtrip delay. Since the diameter of the body lumen is twice the radius of the body lumen, the diameter of the body lumen can be estimated using the equation: diameter of the body lumen=measured delay*speed of sound in the medium. Where an ultrasound pulse is travelling through the cooling fluid within a balloon, which would be the case where the transducer 111 is within a balloon that is filled with cooling fluid, it can be presumed that the speed of sound is about 1500 m/sec. For a balloonless embodiment, where the ultrasound pulse is travelling through the blood within a body lumen, it can be presumed that the speed of sound is about 1570 m/sec. Once the controller estimates of the body lumen diameter, or a surrogate thereof, based on an ultrasound echo received by the stepped portion 417 of the transducer 111, the controller 120 can then select one or more ultrasound treatment parameters to use for treating at least a portion of the patient tissue (that surrounds the portion of the body lumen in which the transducer 111 is inserted) using the main portion 416 of the transducer. Additional details of such embodiments are described below with reference to the flowchart of FIG. 12. It is noted that the main portion 416 and the stepped portion of the 417 of the transducer 111 can also be referred to as segments of the transducer. For example, the stepped portion 417 can also be referred to as a first segment of the transducer 111, and the main portion 416 can also be referred to as a second segment of the transducer 111.

Reference is now made to FIG. 12, which is a flowchart that is used to summarize various methods of the present technology that can be used to determine an estimated size of a portion of body lumen, or a surrogate thereof, using a transducer inserted therein, and based on the estimate or surrogate thereof select and use one or more ultrasound treatment parameters. Methods that are summarized with reference to FIG. 12 are for use with an ultrasound transducer (e.g., 111) that is inserted into a portion of a body lumen, wherein the ultrasound transducer includes a first transducer segment (e.g., 417) and a second transducer segment (e.g., 416), wherein the first transducer segment (e.g., 417) has a first thickness (e.g., 0.23 mm) and is configured to emit ultrasound energy having a first center frequency (e.g., 20 MHz) in response to the ultrasound transducer being excited using an excitation signal having the first center frequency, and wherein the second transducer segment (e.g., 416) has a second thickness (e.g., 0.50 mm) and is configured to emit ultrasound energy having a second center frequency (e.g., 9 MHz) in response to the ultrasound transducer being excited using an excitation signal having the second center frequency (e.g., 9 MHz).

Referring to FIG. 12, operation 1202 involves exciting the ultrasound transducer (e.g., 111) with an excitation signal having the first center frequency (e.g., 20 MHz) to thereby cause the first transducer segment (e.g., 417) to emit ultrasound energy having the first center frequency (e.g., 20 MHz). Operation 1202 can be performed by the controller 120, and more specifically, by the controller 120 (or a processor thereof, e.g., 612) controlling an ultrasound excitation source (618) to excite the ultrasound transducer with an excitation signal having the first center frequency.

Operation 1204 involves receiving an ultrasound echo signal using the first transducer segment (e.g., 417), wherein the ultrasound echo signal comprises a portion of the emitted ultrasound energy having the first center frequency (e.g., 20 MHz) that was reflected back towards the ultrasound transducer by a wall of the portion of the body lumen in which the ultrasound transducer is inserted.

Operation 1206 involves determining an estimate of a size of the portion of the body lumen, or a surrogate thereof, based on the ultrasound echo signal that was received using the first transducer segment. Example equations that could be used to estimate a body lumen radius and a body lumen diameter, based on a delay between when an ultrasound pulse is emitted and when a corresponding echo is received, were described above. The delay itself is an example of a surrogate of the size of the portion of the body lumen, as would be a calculated radius. A calculated diameter is an example of an estimate of the size of the portion of the body lumen. Operation 1206 can be performed by the controller 120, or more specifically, a processor thereof (e.g., 612).

Operation 1208 involves selecting at least one ultrasound treatment parameter, for use in treating tissue surrounding the portion of the body lumen using the second transducer segment (e.g., 416), based on the estimate of the size of the portion of the body lumen, or the surrogate thereof, that was determined based on the ultrasound echo signal that was received using the first transducer segment. Operation 1208 can be performed by the controller 120, or more specifically, a processor thereof (e.g., 612). Operation 1210 involves exciting the ultrasound transducer (e.g., 111) with an excitation signal having the second center frequency and using the at least one ultrasound treatment parameter that was selected based on the estimate of the size of the portion of the body lumen, or the surrogate thereof, to thereby cause the second transducer segment (e.g., 416) to emit ultrasound energy having the second center frequency (e.g., 9 MHz) to treat at least a portion of tissue surrounding the portion of the body lumen. Operation 1210 can be performed by the controller 120, and more specifically, by the controller 120 (or a processor thereof, e.g., 612) controlling an ultrasound excitation source (618) to excite the ultrasound transducer with an excitation signal having the second center frequency (e.g., 9 MHz). An example of an ultrasound treatment parameter, that is selected at operation 1208 and used at operation 1210, is an acoustic output power level or a voltage level that is used to achieve that acoustic output power level. Other examples of ultrasound treatment parameters, that can be selected at operation 1208 and used at operation 1210, include a sonication duration, a cooling fluid flow rate during sonication, and/an excitation signal duty cycle, but are not limited thereto. The system may further use this information to determine and communicate (e.g., on a graphic user interface and/or audio device) balloon pressure and/or balloon inflation diameter indicated according to a look-up-table that correlated body lumen diameter with required balloon requirements, prior to inflating the balloon 112 around the transducer 111. Tables 3 and 4, discussed above, are examples of look-up-tables that can be used at operation 1208 to select ultrasound treatment parameter(s) based on an estimate of a body lumen size, or a surrogate thereof. Similar look-up-tables can be generated, saved, and used for other types of surrogates, such as the aforementioned delay and/or estimated radius of the body lumen.

In certain embodiments, the ultrasound transducer (e.g., 111) with which the methods summarized with reference to FIG. 12 can be used can have a cylindrical transducer body (e.g., 201) made of piezoelectric material. The first transducer segment (e.g., 417) can be a first longitudinal segment of the cylindrical transducer body, and the second transducer segment (e.g., 416) can be a second longitudinal segment of the cylindrical transducer body, which is adjacent to and concentric with the first transducer segment. In such an embodiment, the first thickness (e.g., TH1) corresponds to a thickness (e.g., 0.23 mm) of the first longitudinal segment (e.g., 417) of the cylindrical transducer body, between a respective inner cylindrical surface and a respective outer cylindrical surface thereof. The second thickness (e.g., TH2) corresponds to a thickness (e.g., 0.50 mm) of the second longitudinal segment of the cylindrical transducer body, between a respective inner cylindrical surface and a respective outer cylindrical surface thereof. In certain embodiments, the first thickness (e.g., 0.23 mm) is less than the second thickness (e.g., 0.50 mm), and the first center frequency (e.g., 20 MHz) is greater than the second center frequency (e.g., 9 MHz). In certain such embodiments, the first center frequency is at least twice the second center frequency. In other embodiments, the first thickness is greater than the second thickness, and the first center frequency is less than the second center frequency, e.g., second center frequency is at least twice the first center frequency. In accordance with certain embodiments, the first longitudinal segment (e.g., 417) of the cylindrical transducer body (e.g., 201) has a first longitudinal length (e.g., 0.4 mm), and the second longitudinal segment (e.g., 416) of the cylindrical transducer body has a second longitudinal length (e.g., 5.7 mm) that is at least twice the first longitudinal length.

In accordance with certain embodiments, for the first transducer segment (e.g., 417), one or more layers of backing materials, one or more layers of matching layers, and/or one or more acoustic lens may be used to improve or shape the transducer spectrum and sensitivity.

While in the example embodiments described above the first segment was described as being thinner than the second segment, and the first segment was described as having higher resonance frequency than the second segment, the opposite can instead be true, so long as the first and second segments have different resonance frequencies and can be selectively and separately excited.

In accordance with certain embodiments, the ultrasound transducer (used in the methods summarized with reference to FIG. 12) is located within an interior of a balloon (e.g., 112) through which cooling fluid is circulated, the balloon is configured to occlude the body lumen, and the cooling fluid cools both the transducer and the lumen during sonications. In other embodiments, the ultrasound transducer is located within an interior of a balloon through which cooling fluid is circulated, the balloon does not occlude the body lumen during sonications, and the cooling fluid cools only the transducer during sonications. In still other embodiments, i.e., balloonless embodiments, the ultrasound transducer is not located within an interior of a balloon, but rather, is located directly in the blood stream of a body lumen such that the transducer comes into contact with blood.

In accordance with certain embodiments, instead of the ultrasound transducer 111 that is used for tissue treatment being used to determine an estimate of a size of a body lumen, or a surrogate thereof, a separate ultrasound transducer that is located on a distal portion of a guidewire that is used to determine an estimate of a size of a body lumen, or a surrogate thereof, either before or after a catheter 102 with an ultrasound transducer 111 (used for treatment) is inserted over the guidewire and inserted into the body lumen. If the separate ultrasound transducer (that is located on a distal portion of a guidewire) is used to determine an estimate of a size of a body lumen, or a surrogate thereof, before (i.e., prior to) a catheter 102 with an ultrasound transducer 111 (used for tissue treatment) is inserted over the guidewire and inserted into the body lumen, then in addition to the estimate of the size of the body lumen, or the surrogate thereof, being used to select one or more ultrasound treatment parameters, the estimate of the size of the body lumen, or the surrogate thereof, can be used to select an appropriate one of a plurality of different catheters and/or balloons thereof. For example, a first catheter may have a first balloon that is intended to be used with body lumen sizes within a first range, a second catheter may have a second balloon that is intended to be used with body lumen sizes within a second range, etc. Based on the estimate of the size of the body lumen, or the surrogate thereof, the appropriate catheter can be selected to use for tissue treatment and guided into the body lumen using the guidewire that has the ultrasound transducer that was used to determine the estimate of the size of the body lumen, or the surrogate thereof.

Figure 13:
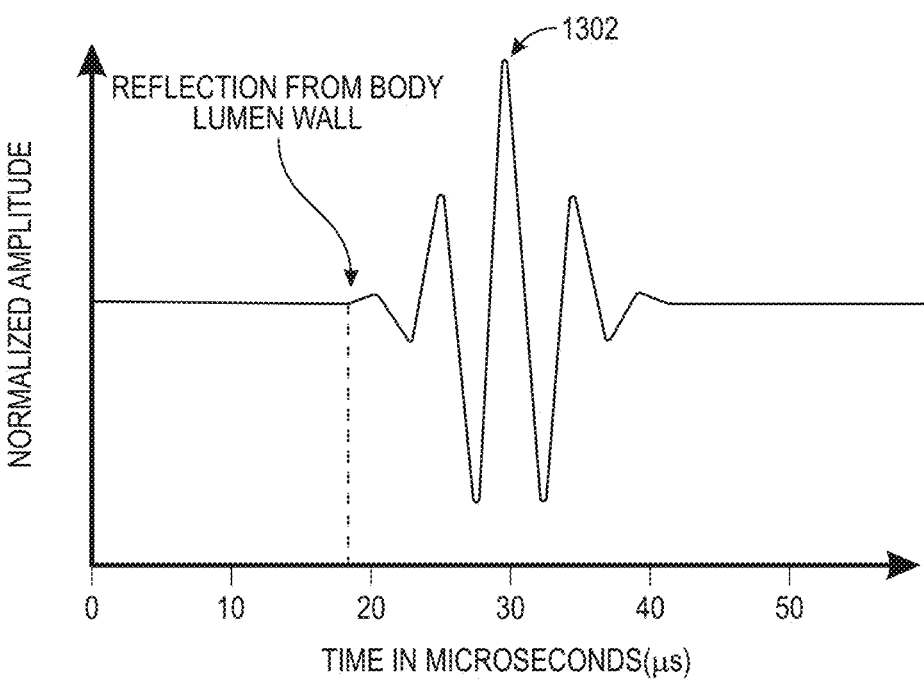
FIG. 13 is an example graph of normalized amplitude versus time for an ultrasound echo signal that can be received by the transducer following an ultrasound pulse being emitted by the transducer, in accordance with an embodiment.

FIG. 13 is an example graph of normalized amplitude versus time for an ultrasound echo signal that can be received by the transducer 111 (or the stepped portion 417 thereof) following an ultrasound pulse being emitted by the transducer 111 (or the stepped portion 417 thereof). The point in the curve 1302, which is pointed to by the arrow in FIG. 13, is indicative of an initial point of reflection from the body lumen wall. The temporal delay between when the ultrasound pulse was emitted and when the echo signal was received, as explained above, can be used to determine an estimate the body lumen size, or a surrogate thereof, which in-turn can be used to select one or more ultrasound treatment parameters. Additionally, or alternatively, such a received echo signal can be used to determine whether the transducer 111 is centered within the portion of the body lumen within which the transducer 111 is inserted, as explained below with reference to FIGS. 14 and 15. The curve or wave front 1302 of the echo signal shown in FIG. 13 is an example of what the wave front may look like where the transducer 111 is centered within a portion of the body lumen, in which case the reflections from different points about the generally circular circumferential body lumen can be received by the transducer 111 (or the one or more stepped portions thereof 417) at substantially the same time resulting in constructive interference. If by contrast, the transducer 111 is not centered within a portion of the body lumen, but rather is tilted or slanted within the portion of the body lumen, then the reflections from different points about the generally circular circumferential body lumen can be received by the transducer 111 (or the stepped portion thereof 417) at various different times resulting in destructive interference. In other words, when reflected signals come back from all directions, the phase of echoes cannot be aligned unless the transducer is centered.

Figure 14:
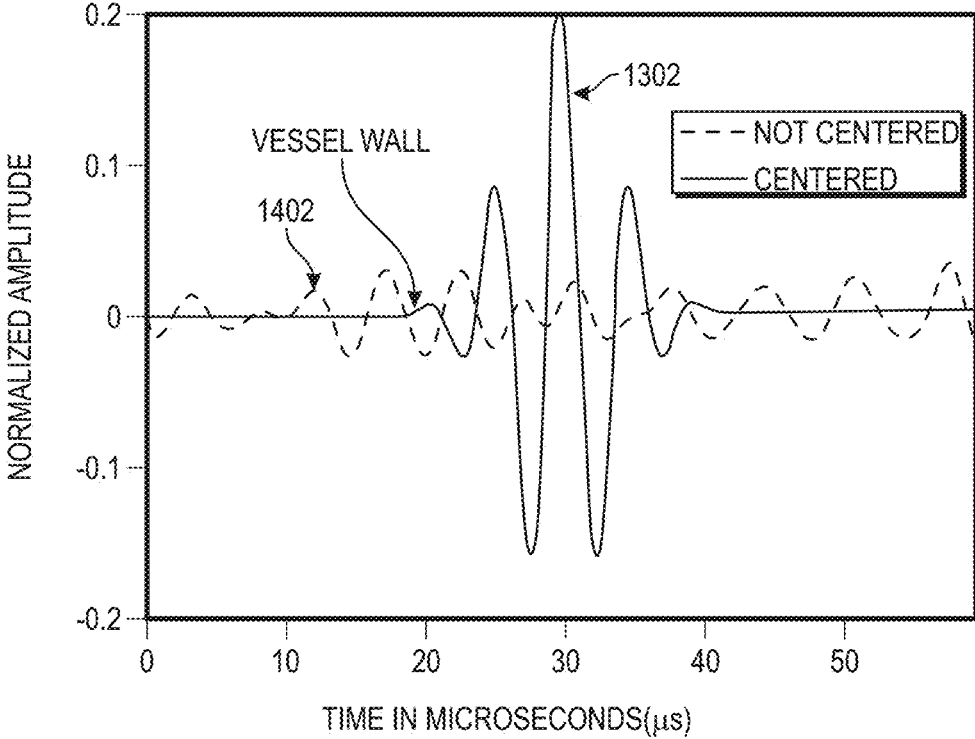
FIG. 14 is an example graph that is similar to the graph in FIG. 13, but also shows how the ultrasound echo signal may look different where the transducer is not centered within a portion of a body lumen, in accordance with an embodiment.

FIG. 14 is another example graph of normalized amplitude versus time for an ultrasound echo signal that can be received by the transducer 111 (or the one or more stepped portions 417 thereof) following an ultrasound pulse being emitted by the transducer 111 (or the one or more stepped portions 417 thereof). FIG. 14 includes the same curve or wave front 1302 of the echo signal that was shown in FIG. 13, and also includes another curve or wave front 1402 that shows what an echo signal might look like where the transducer 111 is not centered within a portion of the body lumen. The controller 120 can be provided with the echo signal received by the transducer 111, or a signal indicative of the echo signal, and can perform a signal analysis to determine whether the transducer 111 is centered within a portion of a body lumen. In certain embodiments, the controller 120 is provided with the echo signal received by the transducer 111, or a signal indicative of the echo signal, performs a signal analysis to determine the angle at which the transducer 111 is off-centered (the "angle of tilt") with respect to a longitudinal axis of the body lumen. The controller 120 may have a memory comprising a look-up table that associates a certain curve or wave front 1302 with a particular angle of tilt. The controller 120 may then use this angle of tilt to validate and/or calibrate a body lumen diameter measurement. In a non-limiting example, if the transducer 111 has an angle of tilt greater than a threshold, e.g., 30°, the controller 120 may alert the user that the catheter needs to be adjusted and/or diameter measurements using the transducer are not sufficiently reliable. In certain embodiments, where multiple measurements are being used to determine body lumen diameter, the echo measurement may be weighed less depending on the magnitude of the angle of tilt up until the threshold, indicating the angle of tilt renders the echo measurement unusable. For example, if the echo measurement and body lumen measurement based on flow rate of cooling fluid are both being used to determine the body lumen diameter, the controller 120 may weigh the cooling fluid measurement more when doing a weighted average, and the greater the angle of tilt of the transducer 111, the greater cooling fluid measurement may be weighed.

In some embodiments, the controller 120 includes memory having a look-up table that includes the angle of tilt in determining the diameter of the body lumen size. Due to destructive interference, the measured temporal delay between when the ultrasound pulse was emitted and when the echo signal was received may appear smaller in amplitude the more the transducer 111 is tilted. Therefore, the look-up table may take into account both the angle of tilt and the temporal delay in determining body lumen diameter.

Figure 15:
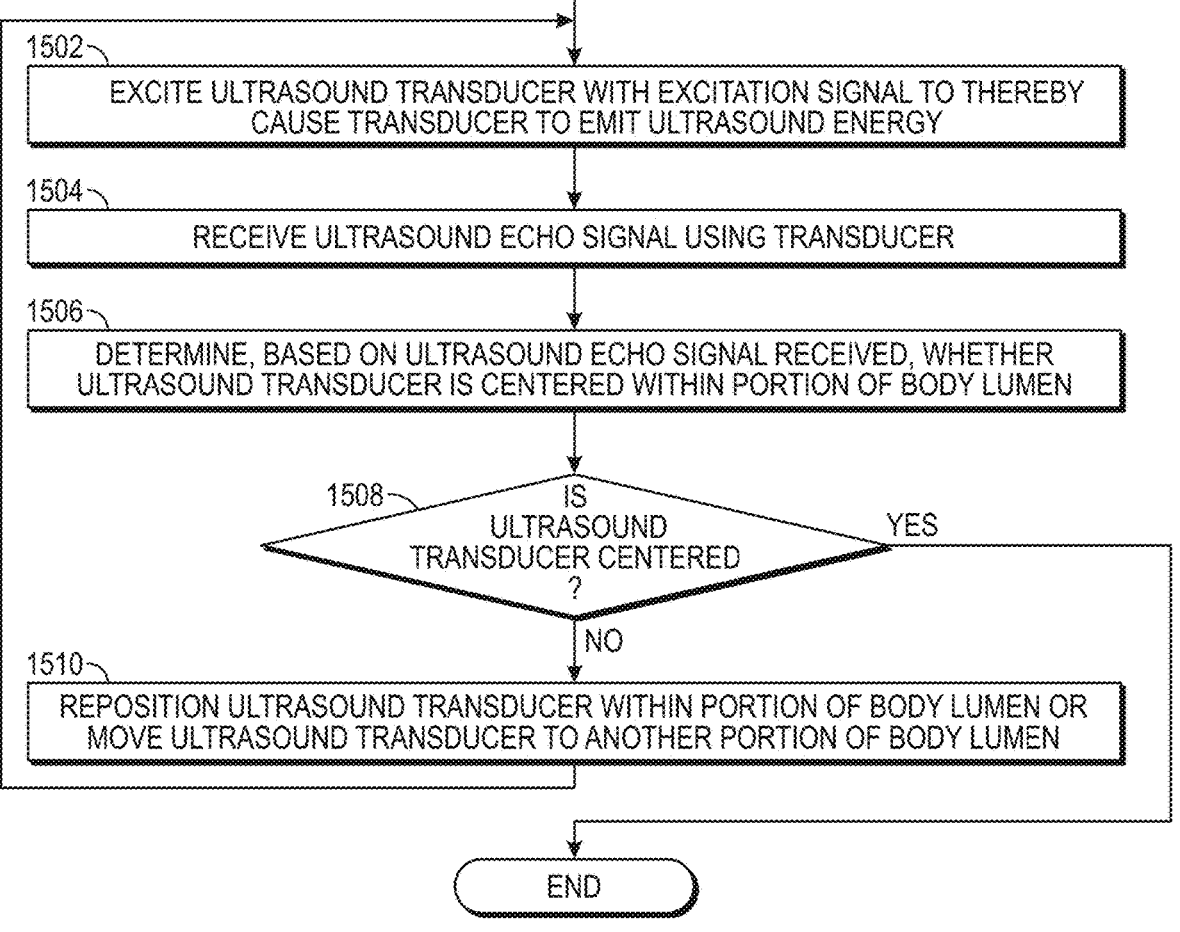
FIG. 15 is a flowchart that is used to summarize methods of the present technology that can be used to determine whether a transducer is centered within a portion of a body lumen within which the transducer is inserted, in accordance with an embodiment.

The flowchart of FIG. 15 will now be used to summarize methods of the present technology that can be used to determine whether a transducer (e.g., 111) is centered within a portion of a body lumen within which the transducer is inserted. It will be appreciated that the description of determining whether the transducer is centered within the body lumen is independent of the description of determining or estimating a size of the body lumen. More particularly, the tissue treatment system 100 may be used to determine either that the transducer is centered or the estimated body lumen size. The determinations may be used in combination (or not) during a procedure. That is, the system may be used to determine one or both of whether the transducer is centered or the body lumen size. Accordingly, the description of determining centering of the transducer is not intended to be limiting of the description of determining the body lumen size, and vice versa.

Referring to FIG. 15, operation 1502 involves exciting the ultrasound transducer with an excitation signal to thereby cause the ultrasound transducer to emit ultrasound energy. Operation 1504 involves receiving an ultrasound echo signal using the ultrasound transducer, wherein the ultrasound echo signal comprises a portion of the emitted ultrasound energy that was reflected back towards ultrasound transducer by a wall of the portion of the body lumen in which the ultrasound transducer is inserted. Operations 1506 and 1508 involve performing signal analysis to determine, based on the ultrasound echo signal that is received, whether the ultrasound transducer is centered within the portion of the body lumen. The controller 120 can perform the signal analysis of the received echo signal to perform operation 1506. If the answer to the question at operation 1508 is No (i.e., if it was determining that the ultrasound transducer is not centered within the portion of the body lumen), then operation 1510 can be performed, which involves repositioning the ultrasound transducer within the portion of the body lumen or moving the ultrasound transducer to another portion of the body lumen. Flow then returns to operation 1502 and the above described operations are repeated to determine if repositioning or moving the transducer resulted in the transducer being centered. After there is a determination that the ultrasound transducer is centered within the portion of the body lumen, this portion of the method ends, but thereafter, the ultrasound transducer can be used to emit further ultrasound energy that is used to treat at least a portion of tissue surrounding the portion of the body lumen.

In accordance with certain embodiments, operations 1502, 1504, and 1506 can be performed using the stepped portion 417 of the transducer 111. In other words, the methods summarized with reference to FIG. 15 can be used with a transducer 111 that is the same as or similar to the one shown in FIGS. 11A-11B, in which case operation 1502 can involve exciting the ultrasound transducer with an excitation signal having a first center frequency to thereby cause a first transducer segment (e.g., 417) to emit ultrasound energy having the first center frequency, and operation 1504 can involve receiving the ultrasound echo signal using the first transducer segment (e.g., 417). In certain embodiments, once the transducer is determined to be centered, a method summarized above with reference to FIG. 12 can be performed to determine an estimate of a size of the portion of the lumen in which the transducer is inserted, or a surrogate thereof, and one or more excitation parameters can then be selected and used to treat tissue. Where certain operations are redundant, they need not be repeated.

Referring briefly back to FIG. 11A, in the transducer 111 shown therein, the transducer 111 includes only a single stepped portion 417, which is shown as being adjacent to the proximal end of the transducer. In other embodiments, a transducer can include more than one stepped portion.

Figure 11B:
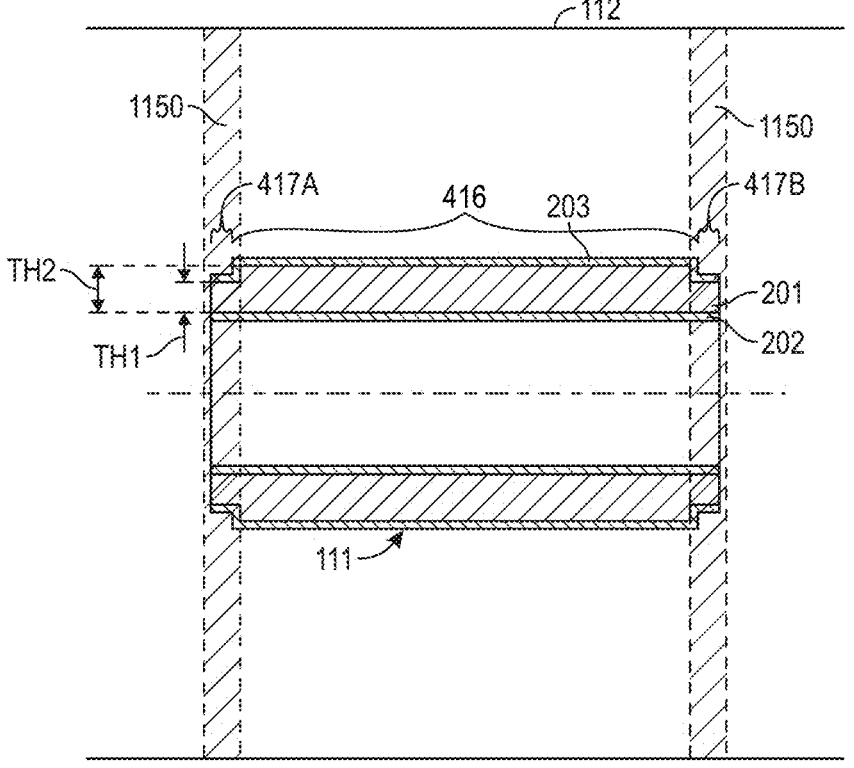
FIG. 11B is a longitudinal cross-sectional view of an ultrasound transducer having several stepped segments, in accordance with an embodiment.

FIG. 11B is a longitudinal (also referred to as a axial) cross-sectional view of the ultrasound transducer 111 having several stepped segments, according to certain embodiments of the present technology. In an embodiment, the transducer 111 includes a pair of end transducer segments 417A and 417B, e.g., one at the proximal end of the transducer and another at the distal end of the transducer. Accordingly, the transducer 111 can be referred to as a dual stepped transducer. The thicknesses of the multiple stepped portions can be the same as one another, in which case they would have the same frequency characteristics. Alternatively, different stepped portions of the transducers can have different thicknesses than one another, in which case they would have different frequency characteristics, and can be separately used to emit pulses and receive echoes, and they can have individual channels, in which case they can collectively operate as a transmitter and receiver array that enables separate channels to be processed separately. Where different stepped portions have different thicknesses, and there are multiple channels, band pass filters (e.g., digital bandpass filters) can be designed to extract the signals from a specific receive element.

In an embodiment, the catheter 102 includes one or more reflective elements 1150 disposed about the transducer 111. The reflective elements 1150 can include, for example, rings, ring electrodes, patches arranged in a radial path about the transducer 111, etc. The reflective elements 1150 can be formed from a material that is acoustically reflective or has an acoustic impedance significantly different from that of water. Accordingly, the reflective elements can be acoustically transparent.

In an embodiment, the reflective elements includes metallic rings, which are acoustically reflective. The metallic rings can be disposed on the balloon 112. The rings can, for example, be printed, sputtered, etc. onto a surface of the balloon. The rings can make a circumferential ring around the balloon. For example, two ring electrodes can be disposed on an inner surface and/or an outer surface of the balloon. In an embodiment, the rings are placed on the balloon such that they do not interfere with the acoustic signal of the non-stepped portion of the transducer 111. More particularly, the rings can be located away from an acoustic aperture of the transducer 111. The rings can accordingly reflect back the acoustic signals of the stepped portions 417A and 417B when the signals reach the balloon surface, however, the rings may be placed in a null region of the acoustic intensity field distribution of a medial transducer segment 416. It is contemplated that the use of the rings can increase the echo signal reflected back to step portions 417A and 417B.

The transducer 111 can include a medial transducer segment 416 between the pair of end transducer segments 417A, 417B. The medial transducer segment 416 can have a respective center frequency, as described above with respect to FIG. 11A. Accordingly, the end transducer segments 417A, 417B can emit respective center frequenc(ies) that differ from a frequency emitted by the medial transducer segment 416. Although the reflective elements 1150 are illustrated as being radially around the pair of end transducer segments 417A, 417B, it will be appreciated that a reflective element could be longitudinally aligned with the medial transducer segment 416. In such case, the reflective element may be located in a null or non-peak region of the acoustic intensity field distribution of the medial transducer segment 416 to improve accuracy of lumen size determination while minimally affecting the ultrasonic energy being delivered to the vessel wall for treatment.

Figure 16A:
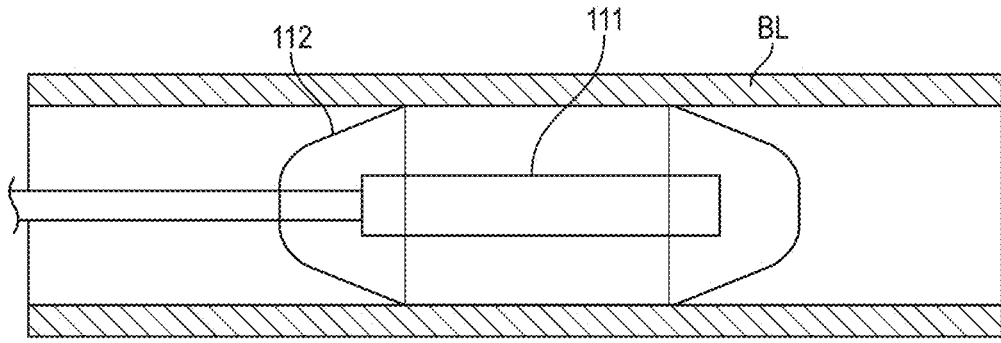
FIG. 16A illustrates how a balloon that surrounds an ultrasound transducer and is in apposition with a body lumen can be used to center the transducer within the body lumen, in accordance with an embodiment.
Figure 16B:
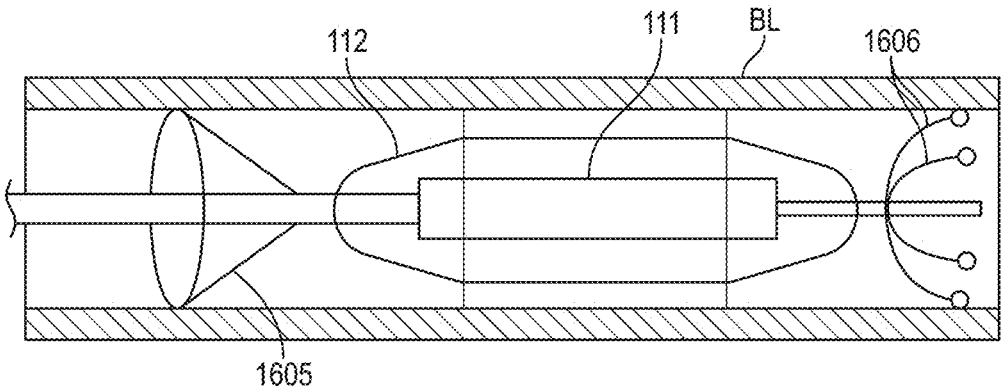
FIG. 16B illustrates how one or more flexible baskets and/or extensions that expand distal and/or proximal of an ultrasound transducer may be used to center the transducer within a body lumen, in accordance with an embodiment.

Certain embodiments of the present technology are specifically for use with a catheter 102 that includes a transducer 111 surrounded by a balloon 112, wherein the balloon is configured to be inflated such that is comes into apposition with a portion of a body lumen, such as the renal artery, within which the transducer 111 and balloon 112 are positioned. Cooling fluid can be circulated through the balloon to cool the transducer during use. In such an embodiment, an example of which is shown in FIG. 16A, it is the balloon 112 that is used to center the transducer 111 within the body lumen. FIG. 16A shows a distal portion 210 of the catheter 102 inserted into a body lumen, such as a renal artery, such that the balloon 112 when sufficiently inflated with cooling fluid is in apposition with the body lumen. In alternative embodiments, the balloon 112 may surround the transducer 111 in order to cool the transducer during sonications, but the balloon 112 may not contact or occlude the body lumen, and the blood within the body lumen may be relied upon to cool the body lumen instead of the cooling fluid. Referring to FIG. 16B, in certain such embodiments, instead of relying on the balloon 112 to center the transducer 111, one or more flexible baskets 1605 and/or extensions 1606 that expand distal and/or proximal of the transducer 111 may be used to center the transducer 111. In an embodiment, the one or more flexible baskets 1605 comprises an array of electrodes, and impedance measurements may be made between the electrodes to determine a diameter of a portion of a body lumen. In an embodiment, the extensions 1606 may each comprise an electrode, and impedance measurements may be made between the electrodes to determine a diameter of a portion of a body lumen. In an alternative embodiment, at least one balloon that expands proximal and/or distal of the transducer 111 may be used to center the transducer 111.

Figure 16C:
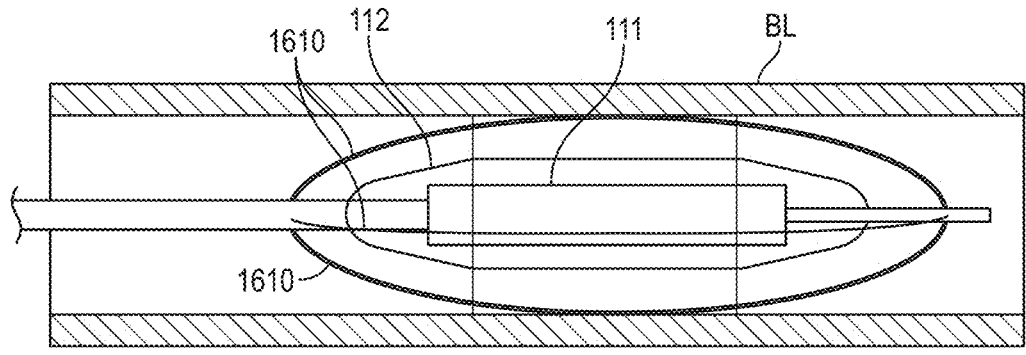
FIG. 16C illustrates how a basket that surrounds a transducer and a balloon may be used to center the transducer within a body lumen, in accordance with an embodiment.

Referring to FIG. 16C, in another embodiment, a basket 1610 that surrounds the transducer 111 and the balloon 112 may be used to center the transducer 111, which basket 1610 is preferably mounted to the catheter at a location that does not interfere with the acoustic field of the transducer 111, e.g., proximal, distal, and/or between the lobes of the acoustic field. In other embodiments, the basket 1610 is made of a material, or has a structure, that does not interfere with the sonications. For example, the material may be acoustically transparent, such as carbon, carbon nanotubes, high impact polystyrene. The structure can include acoustic windows or openings that can be positioned between the transducer 111 and a target ablation region. Accordingly, acoustic lobes emitted by the transducer 111 can pass through the windows or openings without encountering the basket 1610, and thus, the structure does not interfere with sonications.

One of the methods described above with reference to FIG. 15 can be used to determine whether the baskets, extensions, balloons, and/or the like, properly centered the transducer 111 within a portion of a body lumen, and if not, the transducer 111 may be maneuvered until confirmation of proper centering within the body lumen is confirmed. In certain embodiments, the one or more flexible baskets 1605 could comprise electrodes configured to deliver RF energy and/or sense for nerve activity. In certain embodiments, a spiral member 1612 may be used in lieu of baskets 1605 and/or extensions 1606 to center the transducer 111. The spiral member 1612 may comprise electrodes configured to measure nerve activity.

In certain embodiments, a spiral member 1612 may comprise electrodes to determine body lumen diameter. For example, impedance measurements may be made between electrodes to determine diameter in a portion of a body lumen.

Nerve Mapping/Sensing

In embodiments that utilize a balloon (e.g., 112), balloon inflation causes transient ischemia in the kidney or other organ supplied by the blood vessel. This transient ischemia can increase sympathetic nerve traffic. In certain embodiments, the controller 120 may inflate the balloon 112 such as to augment nerve signaling, which may be detected using a nerve probe and method according to U.S. Pat. No. 9,999,463, US Patent Publication No. 2020/0077907, and US Patent Publication No. 2022/0095979. Specifically, inflating the balloon to intentionally create end organ ischemia can be employed to increase signaling to improve nerve detection by a nerve sensing technology. It could be done before, during, or after an ablation as a physiologic challenge to better detect nerve activity. In some circumstances, the balloon inflation could be performed in branches to better assay nerve activity for a specific region of the end-organ (e.g., kidney). In certain embodiments, if the nerve signal is not sufficiently strong, a user may deflate the balloon 112 and move it to a different location and retest the nerve signal at the new location. If the nerve signal is sufficiently strong, the probe may either communicate with the user, the controller 120, or both with an indication that a target area for ablation has been reached and the ablation may be commenced. In certain embodiments that include multiple balloon configurations, the balloons may be inflated sequentially or at the same time, and the strength of the signal(s) may be used by the user or automatically by the controller 120 to determine ablation sites. According to certain embodiments, the balloon inflation method may be used to map the artery prior to beginning ablation, where the balloon may be inflated, deflated, moved to another location, and inflated at multiple locations to test the sympathetic nerve activity at multiple locations along the, e.g., renal artery, and/or accessory arteries. In certain embodiments, the nerve probe may be in communication with the controller 120 or may be otherwise integrated with the nerve probe, such that either the controller 120 or the probe accumulates a nerve map with inputted data from the tests. In certain embodiments, a graphic user interface may be created that displays the nerve map, which may include icons or other indications for ideal ablation targets. In certain embodiments, the increase in nerve traffic can be used to detect balloon apposition with the artery wall, which can then be used to determine artery diameter and ablation parameters, as disclosed herein.

Figure 17:
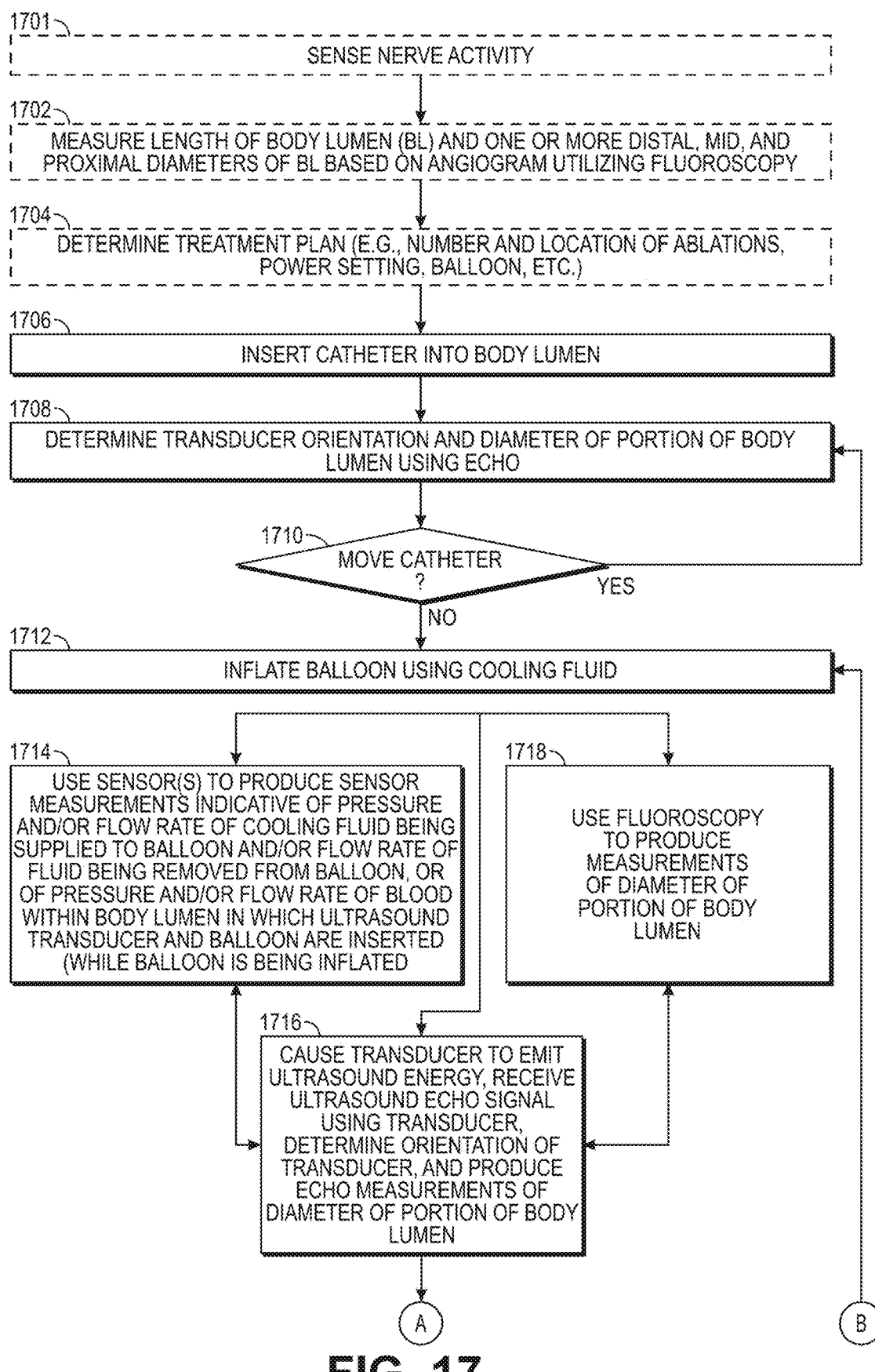
FIG. 17 is a flowchart that is used to summarize various methods of the present technology that can be used to determine an estimate of a size of a portion of a body lumen, or a surrogate thereof, and/or determine whether a transducer is centered within a portion of a body lumen within which the transducer is inserted, and based on the estimate or surrogate thereof select and use one or more treatment parameters, in accordance with an embodiment.
Figure 17:
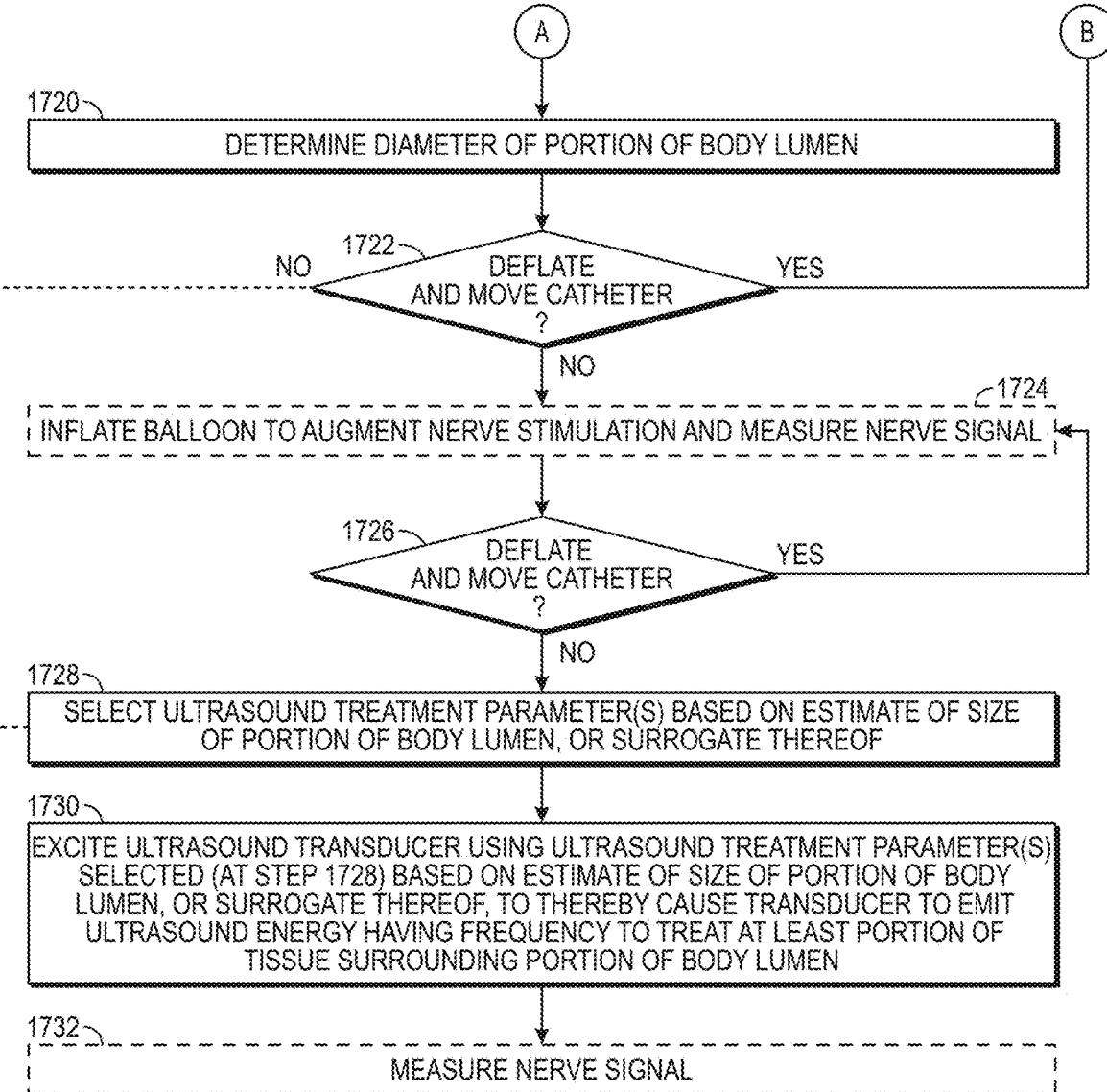

One or more of the foregoing techniques can be combined to provide for a more accurate, user-friendly treatment plan. For example, as depicted in FIG. 17, according to certain embodiments, at operation 1701 a nerve probe may be inserted into the body lumen, e.g., renal artery, and nerve activity may be sensed. In certain embodiments, this initial assessment may be done to determine whether the patient is a good candidate for denervation. For example, the nerve probe may determine whether the patient has a hyper-stimulated nerves in the body lumen and/or determine that the anatomy of the nerves is appropriate for denervation, e.g., the ablation energy used by the catheter is likely to reach the target sufficiently to treat the patient. In certain embodiments, operation 1701 may be omitted, performed in a different sequence, e.g., after operation 1702 (which is also optional), and/or the nerve probe may be integrated with catheter 102.

According to certain embodiments, at operation 1702 conventional imaging techniques, such as fluoroscopy, computed tomography, or intravascular diagnostic ultrasound may be used to measure the length and diameter of one or more portions (e.g., distal, mid, and proximal) of the renal artery. In certain embodiments a nerve probe may be used to sense and/or map nerve activity before and/or after one or more renal artery diameters and length are measured. In certain embodiments, a separate nerve probe is used to measure nerve activity before and/or after the treatment catheter is inserted into the patient. In certain embodiments, one or more electrodes on the balloon 112 are used to sense nerve activity. Optionally, a user may input measurements of nerve activity, body lumen diameter, and body lumen length into a graphical user interface of the controller 120, and the controller 120 may propose a treatment plan (e.g., location and quantity of ablations, required balloon size, balloon volume, power level, cooling fluid flow rate, balloon pressure, etc.) using the user input and present this plan through the graphical user interface (at operation 1704).

Figure 18:
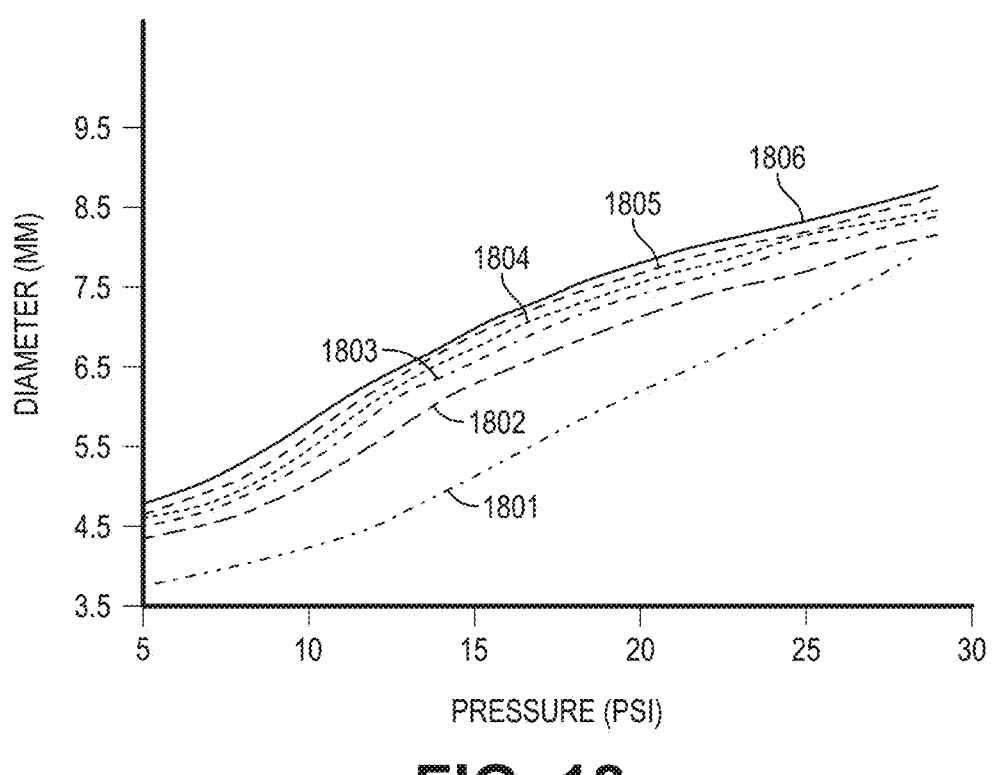
FIG. 18 is a diagram of balloon pressure curves of a balloon being inflated before and after sonications, in accordance with an embodiment.

In certain embodiments, the controller 120 takes into account the compliance curve(s) and/or minimum and maximum inflation diameters of a balloon 112 in determining a treatment plan. For example, if a sufficient number of ablations along the main renal artery and/or renal artery branches can be made using the same catheter, the controller 120 may set a preference for these locations. In certain embodiments, the balloon 112 comprises material, e.g., Isothane® 55 D, such that the compliance curve shifts upwards with each sonication in a consistent and predictable manner, as depicted in FIG. 18. The diameter of the balloon gets larger at a given pressure with each sonication because the material is becoming permanently stretched. FIG. 18 shows the balloon can be inflated to the first inflation diameter to have a first diameter-pressure curve 1801 when the tissue treatment system is introduced into a renal artery before the first sonication. The balloon may be inflated one or more additional times to treat different regions along a length of the renal artery and may have a second compliance curve 1802, a third compliance curve 1803, a fourth compliance curve 1804, a fifth compliance curve 1805, and sixth compliance curve 1806, after the first, second, third, fourth, etc., sonications, respectively. The controller may compensate for this known increase in diameter by lowering the amount of pressure applied to the balloon in order to reach a similar diameter, except that once the pressure is lowered below a threshold, the balloon may not be able to center the transducer 111, cool the body lumen wall, and/or hold the electrodes with sufficient pressure along the body lumen wall. The controller 120 may also set a preference for ablating smaller diameter locations along the body lumen first, so as to minimize the exchange of catheters, with a preference for only using one catheter during the procedure, and to minimize required changes in pressure.

The controller 120 may determine multiple ablation patterns along the body lumen in order to account for multiple contingencies (e.g., an inaccurate BL diameter measurement, as detected by another measuring technique described herein, and/or an inadequate change in the nerve signal after one or more sonications, etc.) and display these contingencies, e.g., as dotted lines, along with the preferred treatment plan. The treatment plan can be displayed on a screen, monitor, or other type of display in real-time for a user to view during and/or after a procedure.

The controller 120 may also suggest one or more catheters (e.g., having a balloon 112 of a certain nominal diameter or compliance curve) to be used and the order in which the catheters 102 are to be used, if applicable. In certain embodiments, each catheter 102 has a color associated with a specific balloon characteristic and the graphic user interface uses a matching color to indicate the catheter 102 to be used. In certain embodiments, the controller 120 may additionally or alternatively have an LED light at the electrical port where the catheter cable 102 plugs into the controller 120 that changes color in coordination with the suggested catheter 102. The user interface may prompt the user to plug in the catheter 102 to the controller 120 and/or LED light may begin to blink and then change to a solid color once the catheter 102 is plugged in. Alternatively, a catheter 102 having a compliant balloon 112 capable of treating a full range of body lumen sizes (e.g., renal arteries that typically range from 2 mm to 8 mm) may be used.

After the selection of the catheter 102 (if applicable), the distal end of the catheter 102 may then be inserted into the body lumen at a first proposed treatment site (at operation 1706). In certain embodiments, the method omits operations

1702 and 1704, and a catheter 102 is inserted into a body lumen (at operation 1706) without these measurements or treatment plan.

The controller 120 may then determine the angle of the transducer 111 with respect to the longitudinal axis body lumen by using the transducer 111 to emit and receive an ultrasound echo signal and use the amplitude of the received signal to determine an orientation of the transducer. The controller 120 may include a memory having a look-up table that associates amplitudes of a received signal with transducer angles within a body lumen. As described with respect to FIG. 14, the controller 120 may use the transducer 111 to measure the diameter of the body lumen at the first proposed treatment site and use the measured transducer angle to calibrate this measurement (at operation 1708). In embodiments where diameter measurements are taken at operation 1702 as well as operation 1708, the diameter measurement at operation 1708 may be compared to the measurement taken at operation 1702. If the difference between measurements exceeds a threshold, the user may be prompted to use fluoroscopy again to confirm the measurement. The controller 120 then determines whether to move the catheter 102 (at operation 1710) based on the diameter measurement. For example, if the body lumen diameter is determined to be too small or too large for catheter 102, catheter 102 may be moved and operation 1708 may be repeated.

If the portion of the body lumen is determined to be within an appropriate range, the balloon may be inflated using cooling fluid at operation 1712. During inflation, the pressure and/or the flow rate of cooling fluid being supplied to the balloon 112 and/or the flow rate of the cooling fluid being removed from the balloon 112, and/or the flow rate of the blood 112 within the body lumen may be sensed to determine apposition of the balloon 112 to the body lumen and again confirm body lumen diameter (at operation 1714). Alternatively, or in addition, during, after, or before inflation of the balloon 112, the controller 120 may activate the transducer to emit ultrasound energy (at operation 1716). The transducer may then receive a return ultrasound echo signal and the controller 120 may use this return ultrasound echo signal to determine the orientation of transducer (the degree of tilt) and produce echo measurements of diameter of portion of body lumen. Also, alternatively, or in addition, during, after, or before inflation of the balloon 112, and during, after, or before the echo measurements, the controller 112 may prompt a user to use fluoroscopy to produce measurements of the diameter of the portion of the body lumen and input this data into the graphic user interface of the controller 120 (at operation 1718).

The controller 120 may use body lumen diameter measurements taken at operation(s) 1714, 1716, and/or 1718 to determine a diameter of the portion of the body lumen (at operation 1720). In certain embodiments, the controller 120 uses the body lumen diameter measurements taken at operation(s) 1702, 1708, 1714, 1716, and/or 1718 to determine a diameter of the portion of the body lumen (at operation 1720). The controller 120 may average or use a weighted average to determine the body lumen diameter.

In certain embodiments, the controller 120 may then use the diameter measurement determined at operation 1720 to determine whether the balloon should be deflated and moved and operations 1712 and one or more of operations 1714, 1716, or 1718 repeated. If the diameter of the body lumen is determined to be within a threshold range at operation 1722, the controller 112 may move to operation 1724 or alternatively, may skip to operation 1728. Optionally, at operation 1724, the controller 120 may automatically inflate the balloon 112 such as to augment nerve signaling, or the controller 120 may suggest to a user through the graphic user interface to inflate the balloon 112 for the purpose of augmenting the nerve signal. According to certain embodiments, the resulting nerve signal may be detected using nerve probes and methods according to U.S. Pat. No. 9,999,463 and US Patent Publication No. 2020/0077907. If the nerve signal is not sufficiently strong, the system may suggest deflating the balloon 112 and moving it to a different location and retesting the nerve signal at the new location (at operation 1726). In an embodiment, if the nerve signal is sufficiently strong, the controller 120 may deflate the balloon to a diameter that is optimal for sonication (the diameter of the balloon prior to operation 1724). The controller 120 may then use the diameter measurement determined at operation 1720 (either alone or together with the previous diameter measurements) to determine treatment parameters, e.g., a power level, balloon inflation size, fluid flow rate, balloon pressure, etc. Controller 120 may then automatically excite the ultrasound transducer using the ultrasound treatment parameter(s) selected (at operation 1728) based on an estimate of size of a portion of body lumen, or surrogate thereof, to thereby cause transducer to emit ultrasound energy having frequency to treat at least portion of tissue surrounding portion of body lumen. Alternatively, the controller may prompt the user to choose delivery of sonication using the parameters or user modifications using the graphic user interface.

Optionally, the controller 120 may then again measure a nerve signal (at operation 1732) using a nerve probe and provide the measurement to the user interface. If the detected nerve signal after sonication is satisfactory (e.g., the nerve signal has decreased to below a threshold or is no longer detectable), the controller may prompt the user to move on to the next sonication or to end the procedure all together because sufficient denervation has been achieved. If the detected nerve signal after sonication is not satisfactory (e.g., the nerve signal remains above a threshold and/or is detectable), the controller 120 may reassess the treatment plan. For example, the controller 120 may determine that the artery length is sufficient to deliver more ablations then initially proposed (e.g., four ablations instead of three along the main renal artery). Or the controller 120 may simply store the information and reassess the treatment plan after the final planned sonication.

Some of the sizing techniques described above include generating parameter curves and identifying inflections to drive determinations of balloon size at particular points in time. Such techniques can be performed in real time without reference to prior inflations of the balloon. In some instances, however, it may be advantageous to compare the parameter curve of a balloon to prior inflations of the same or other balloons.

Figure 19A:
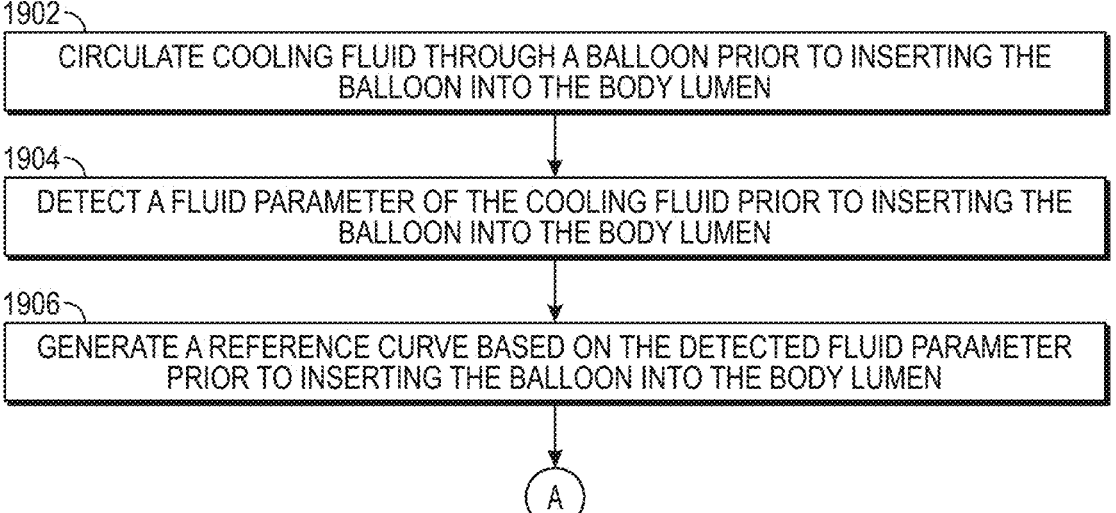
FIG. 19A-19B are flowcharts of a method of sizing a body lumen, in accordance with an embodiment.

Referring to FIG. 19A, a flowchart of a method of sizing a body lumen is shown in accordance with an embodiment. As described below, the sizing determination may be made by comparing a parameter curve of a balloon to a reference curve to identify and draw conclusions from differences in the curves. Due to variability from balloon to balloon, it may be that reference curves of one balloon do not reliably represent the parameter curve of another balloon. Accordingly, optionally, operations 1902-1906 can be performed to generate a reference curve that is specific to a balloon being deployed in a medical procedure. More particularly, a reference curve for a balloon being inflated outside of a body lumen can be generated for comparison to a parameter curve later generated when the balloon is deployed inside of the body lumen.

At operation 1902, a cooling fluid is circulated through a balloon prior to inserting the balloon into a body lumen. In an embodiment, the balloon is submersed in a heated water bath when circulating the cooling fluid through the balloon. For example, the water bath can include water heated to 37 degrees Celsius, or another temperature near body temperature. Inflation of the balloon within the water bath provides a reference inflation for the particular balloon that is planned to be deployed into the body lumen.

At operation 1904 a fluid parameter of the cooling fluid is detected prior to inserting the balloon into the body lumen. While the balloon is immersed in the heated water, the fluid parameter, e.g., a pressure of the cooling fluid, can be measured. Measurement of the fluid pressure can be performed according to the techniques described above.

At operation 1906, a reference curve is generated based on the detected fluid parameter. The reference curve can plot the fluid parameter, e.g., pressure, against an independent variable such as time. Alternatively, the independent variable may be volume of the circulated cooling fluid during the inflation cycle. The generated pressure versus time (P-t) or pressure versus volume (P-V) reference curve can provide the reference curve that describes how the balloon is expected to behave when inflated into a heated fluid bath without a tubular restriction (such as a vessel wall). The reference curve effectively represents how the balloon would expand if deployed into the body without contacting the vessel wall.

Figure 19B:
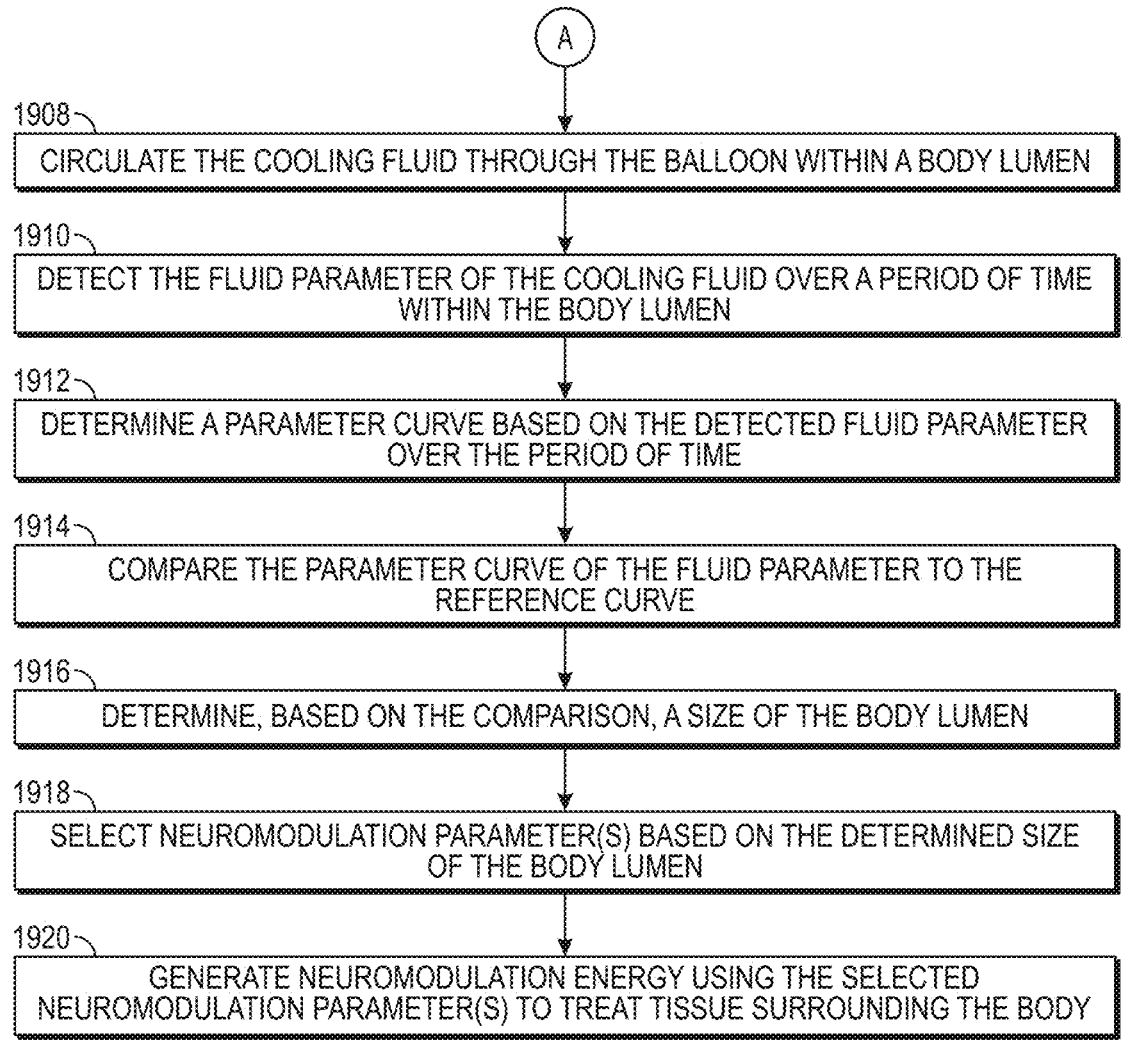

Referring to FIG. 19B, a flowchart of a method of sizing a body lumen is shown in accordance with an embodiment. The operations of FIG. 19B are described with respect to FIG. 20 below. Accordingly, the operations provided in the following description refer back to FIG. 19B.

Figure 20:
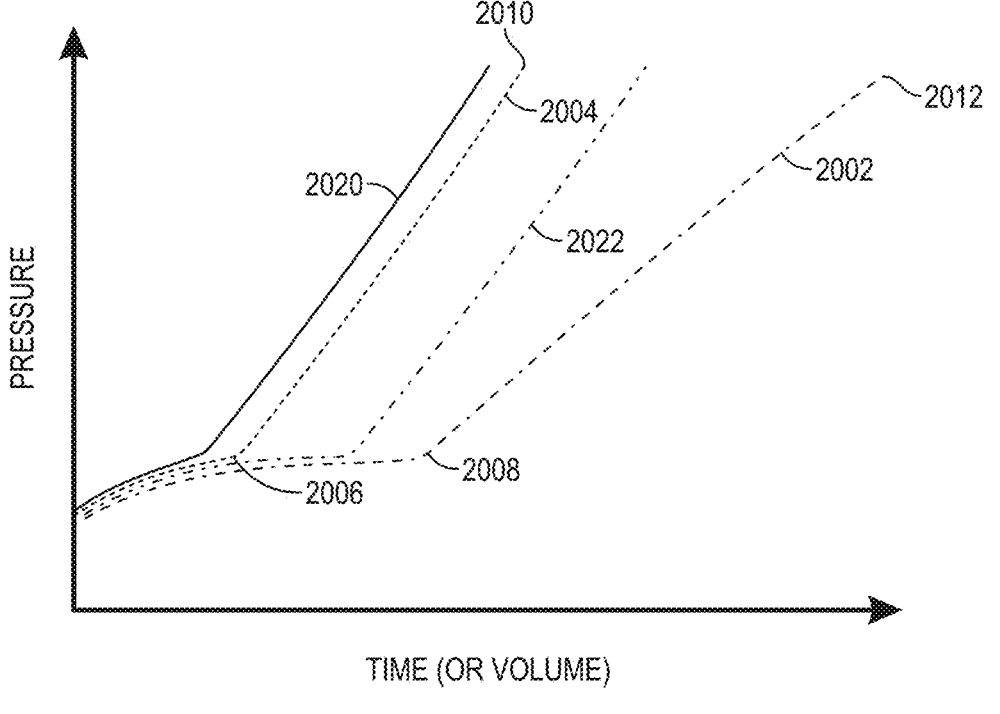
FIG. 20 is a graphical representation of a parameter curve and a reference curve, in accordance with an embodiment.

Referring to FIG. 20, a graphical representation of a parameter curve and a reference curve is shown in accordance with an embodiment. The graph includes a reference curve 2002, which is generated according to operation 1906. The reference curve 2002 plots the pressure within the balloon versus the independent variable, e.g., time or volume, when the balloon is inflated within the heated water bath. The volume may be calculated rather than measured. More particularly, time may be measured and then multiplied by a known or measured fluid flow rate to determine the volume of the circulated cooling fluid. Accordingly, the independent variable, e.g., time, may be measured or calculated from measured values, e.g., volume of the circulated cooling fluid based on time and flow rate. More particularly, in an embodiment, the flow rate of the cooling fluid can be 5 mL/min when inflating the balloon within a range of 0 to 10 psi, and thus, the injected volume (in mL) can be determined by multiplying 5 mL/min by the amount of time (in minutes) that the balloon is inflated. After the reference curve 2002 is generated, the catheter of the tissue treatment system is tracked through the body lumen to a target site. When disposed at the target site, the tissue treatment system can be ready for deployment to sonicate the surrounding tissue.

At operation 1908, cooling fluid is circulated through the balloon within the body lumen over a period of time. Circulating the cooling fluid can inflate the balloon to bring the balloon wall toward apposition with the surrounding vessel wall.

At operation 1910, the fluid parameter of the cooling fluid may be detected over a period of time. Detection can occur while the cooling fluid inflates the balloon within the body lumen.

At operation 1912, a parameter curve 2004 can be determined. The parameter curve 2004 can be generated as a curve that plots the fluid parameter, e.g., pressure, against an independent variable over the period of time. For example, the parameter curve 2004 can plot the pressure against time. Alternatively, the parameter curve 2004 can plot the pressure against volume. The volume may be calculated, rather than measured. For example, as described above, a known flow rate may be multiplied by a measured time to determine the calculated inflation volume.

At operation 1914, the parameter curve 2004 of the fluid parameter can be compared to the reference curve 2002. Comparing the parameter curve 2004 to the reference to curve may include determining a ratio of an inflection 2006 of the parameter curve 2004 to a reference inflection 2008 of the reference curve 2002. As described above, the inflection 2006 points of each curve may be locations on the curve at which the rate of change of the curve increased above a predetermined threshold. The ratio of inflection 2006 points can be determined by dividing the value of the independent variable of the inflection 2006 of the parameter curve 2004 by the value of the independent variable of the reference inflection 2008. The ratio of the illustrated curve can be seen to be about 0.5, by inspection, even without labeled values.

Alternatively, comparing the parameter curve 2004 to the reference curve 2002 can include determining a ratio of an end point 2010 of the parameter curve 2004 to a reference endpoint 2012 of the reference curve 2002. The end points can be points on the curves at which the balloon has reached a predetermined pressure. For example, the parameter curve 2004 representing the balloon inflated within the anatomy can have the end point corresponding to a time or volume when the balloon has a pressure of 10 psi, or another predetermined pressure. Similarly, the reference curve 2002 representing the balloon inflated within the heated water bath can have the end point corresponding to a time or volume when the balloon has a pressure of 10 psi, or the other predetermined pressure. The ratio of end points can be determined by dividing the value of the independent variable of the end point 2010 of the reference curve 2002 by the value of the independent variable of the reference endpoint 2012. The ratio of the illustrated curve can be seen to be about 0.5, by inspection, even without labeled values.

At operation 1916, the size of the body lumen is determined based on the comparison of the curves. In an embodiment, determining the size of the body lumen is based on the ratio calculated from the comparison of the curves. The ratio can be compared or identified in a lookup table that models relative volume of balloons to balloon size. More particularly, the model can represent, for a particular ratio of inflection points or endpoints, what the body lumen size is expected to be. By way of example, ratios of the inflection points or endpoints for a balloon inflated in a range of vessels may vary from 0.3 to 1.0. Those ratios can correspond to balloon sizes of 3.5 to 8 mm. More particularly, a ratio of 0.3 can indicate that the balloon has been inflated within a 3.5 mm vessel, based on the point in time at which the inflection point occurred. Similarly, a ratio of 1.0 can indicate that the balloon has been inflated within an 8 mm vessel, based on the point in time at which the inflection point occurred. Accordingly, the comparison of curves and, more particularly, specific points along the curves can be used to estimate the body lumen size within which the balloon is inflated.

The particular ratio that is used to estimate body lumen size may be based on a known nominal diameter of the balloon. The nominal diameter can be the diameter at which the balloon expands without stretching. For example, at a nominal pressure of, e.g., 2 psi, the balloon may reach a first diameter without the balloon wall stretching from its native geometry. As additional pressure is applied, the balloon can stretch to expand to a larger diameter.

In an embodiment, when the nominal diameter of the balloon is less than a predetermined body lumen size, the ratio of inflection points from the curves may be used to estimate the body lumen size. In such case, the nominal diameter may be determined, e.g., by receiving a user input of the balloon type or size, and the processor of the tissue treatment system can input the ratio of the inflection points to the model to determine body lumen size. Use of the inflection point ratio can be used when the vessel diameter is anticipated to be smaller than the nominal diameter. In such cases, the ratio of inflection points is expected to be more predictive of body lumen size.

In an embodiment, when the nominal diameter of the balloon is greater than a predetermined body lumen size, the ratio of endpoints from the curves may be used to estimate the body lumen size. In such case, the nominal diameter may be determined, e.g., by receiving a user input of the balloon type or size, and the processor of the tissue treatment system can input the ratio of the endpoints to the model to determine body limits size. Use of the end point ratio can be used when the vessel diameter is anticipated to be smaller than the nominal diameter. In such cases, the ratio of end points is expected to be more predictive of body lumen size.

At operation 1918, a neuromodulation parameter is selected based on the size of the body lumen. For example, at least one ultrasound treatment parameter for use in treating tissue surrounding the portion of the body lumen may be selected based on the estimate of the size of the portion of the body lumen, or the surrogate thereof. In certain embodiments, an acoustic output power is selected at operation 1918. Alternatively, or additionally, other types of ultrasound treatment parameters can be selected at operation 1918, including, but not limited to, sonication duration, cooling fluid flow rate during sonication, and/or excitation signal duty cycle.

It will be appreciated that the selection of the neuromodulation parameter may be performed directly as a determination at operation 1916. More particularly, rather than first estimating a size of the body lumen and then selecting the parameter based on the size, the neuromodulation parameter can be determined directly based on the comparison. For example, the ratios calculated through the comparison can be correlated to neuromodulation parameters in a lookup table that is referenced to go directly from the comparison of the curves to the neuromodulation parameters. Accordingly, the selection of the neuromodulation parameter as a secondary operation of estimating the body lumen size is illustrative and not limiting.

At operation 1920, neuromodulation energy is generated based on the neuromodulation parameter. The selected neuromodulation parameter is used to generate the neuromodulation energy to treat the tissue surrounding the body lumen. Generation of the neuromodulation energy involves exciting the ultrasound transducer, using the at least one ultrasound treatment parameter.

In certain embodiments of the present technology, some or all of the operations summarized above with reference to FIGS. 19A-19B are performed fully- or semi-autonomously by the controller 120. Furthermore, as described above, application of the sizing method may be driven by a determination of a balloon type. More particularly, the processor may determine whether the balloon is a compliant balloon or a non-compliant balloon. Such determination may include receiving a user input of the balloon type, model, etc. In response to determining that the balloon is a compliant balloon, the method of determining the size of the body lumen based on the comparison of curves may be applied.

Additional curves, other than the parameter curve 2004 and the reference curve 2002, are shown in FIG. 20. These curves can correspond to additional parameter curves 2004 that the balloon would exhibit if deployed in different artery sizes. For example, a parameter curve 2020 can correspond to the parameter curve that would result from deploying the balloon in a 3 mm vessel. Alternatively, a parameter curve 2022 can correspond to the parameter curve 2004 that would result from deploying the balloon in a 6 mm vessel. It will be appreciated then that the inflection points and end points can vary for the balloon based on the anatomy that it is deployed within, making the method described above an effect way to estimate the body lumen size based on the measured balloon parameters.

Figure 21:
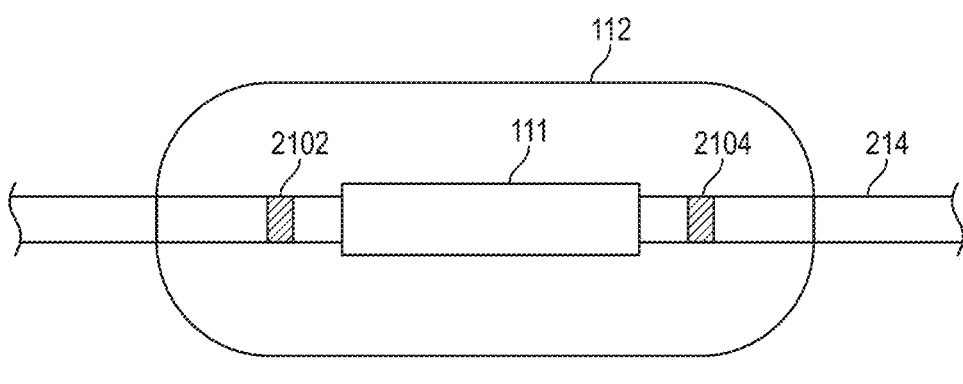
FIG. 21 is a side view of a distal portion of a tissue treatment system, in accordance with an embodiment.

Referring to FIG. 21, a side view of a distal portion of a tissue treatment system is shown in accordance with an embodiment. A tissue treatment system can incorporate a catheter designed to integrate vessel measurement electrodes with an ultrasound therapy transducer. The integrated electrodes can accurately determine a size of a vessel or other body lumen. Accordingly, a treatment dose can be planned according to the measured vessel size.

In an embodiment, the balloon 112 is mounted on the catheter shaft 214 and contains the transducer 111, as described above. One or more sizing mechanisms are mounted on the catheter shaft. The sizing mechanism may use electrical impedance to determine the vessel size. The sizing mechanism can include a pair of electrodes, e.g., a proximal electrode 2102 and a distal electrode 2104. The proximal electrode 2102 can be mounted on the catheter shaft proximal to the transducer, and the distal electrode 2104 can be mounted on the catheter shaft distal to the transducer.

The tissue treatment system may be configured to detect an impedance between the pair of electrodes. The impedance is inversely proportional to an area or a square radius of the balloon. Accordingly, by detecting the impedance, one or more processors of the tissue treatment system can determine or calculate the balloon diameter and/or a diameter of the body lumen, based on the impedance.

Figure 22:
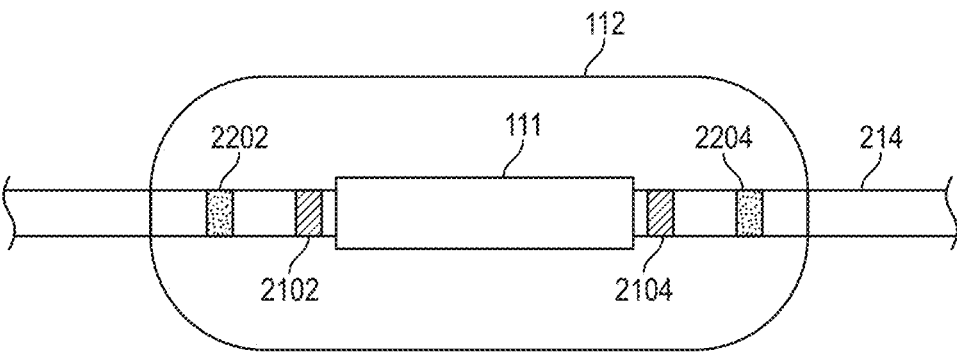
FIG. 22 is a side view of a distal portion of a tissue treatment system, in accordance with an embodiment.

Referring to FIG. 22, a side view of a distal portion of a tissue treatment system is shown in accordance with an embodiment. The sizing mechanism may include two pairs of electrodes. In an embodiment, a first pair of electrodes includes the proximal electrode 2102 and the distal electrode 2104. The sizing mechanism may also include a second pair of electrodes including a second proximal electrode 2202 and a second distal electrode 2204. The second proximal electrode 2202 can be mounted on the catheter shaft proximal to the transducer. The second distal electrode 2204 may be mounted on the catheter shaft distal to the transducer. Both pairs of electrodes can be contained within the balloon.

The sizing mechanism can use impedance planimetry. A constant current can be injected from the second pair of electrodes (the second proximal electrode 2202 and the second distal electrode 2204). A voltage may then be measured between the first pair of electrodes (the proximal electrode 2102 and the distal electrode 2104). By injecting constant current from the outer electrodes and measuring the voltage between the inner electrodes, the measured voltage may be used to determine and impedance. More particularly, the measured voltage can be proportional to the impedance, and inversely proportional to the square radius of the balloon. Accordingly, one or more processors of the tissue treatment system can use the determined impedance to determine the balloon diameter and/or a diameter of the body lumen.

Using the sizing mechanisms of FIGS. 21-22, as with any of the sizing mechanisms or methods described herein, an automatic balloon inflation algorithm can be formed. For example, if the impedance and/or the determined balloon size indicates that a size of the balloon has stopped increasing, the system may determine that the balloon has achieved apposition with the vessel wall. The sizing mechanism can signal the system to discontinue inflation. By stopping inflation, the sizing mechanism cannot only provide information for dose planning, it can also improve safety of balloon inflation by preventing overstretching of a target vessel.

To expand on the previous point, any of the balloon sizing techniques described above may be used to drive a decision about and/or control an inflation process. More particularly, control of the inflation of the tissue treatment system can be based on a determination about whether the balloon has made contact with a vessel wall. When contact is detected, e.g., by determining that an inflection of an inflation curve or a predetermined impedance has been reached, a processor of the tissue treatment system can stop the inflation of the balloon. In an embodiment, stopping the inflation is immediately upon detecting the vessel contact event. In an embodiment, stopping the inflation includes continuing to inflate the balloon for a predetermined period of time or by a predetermined pressure following the event. For example, the balloon may be inflated for an additional 0.5 second or 2 psi after vessel contact is made to ensure that the balloon is secured against the vessel wall during both systole and diastole.

The transducers, apparatuses, the systems, and methods described herein may be used to treat any suitable tissue, which tissue may be referred to as a target anatomical structure. For example, use of the present systems to treat (e.g., neuromodulate) the renal nerve is described above. It should be appreciated that body lumens, in which the present systems may be positioned for treating tissue, are not necessarily limited to naturally occurring body lumens. For example, the treatment may include creating a body lumen within tissue (e.g., using drilling, a cannula, laser ablation, or the like) and then positioning suitable components within such a body lumen. Other suitable applications for the present system include ablation of pulmonary nerve and tissue responsible veins or cardiac arrhythmia, nerves within that intervertebral disk, nerves within or outside of that intervertebral disk, basivertebral nerves within that vertebral bone, nerves within the brain tissue, tissue responsible for cardiac arrhythmia within the cardiac tissue, nerves along the bronchial tree, one or more esophageal branches of the vagus nerve, and one or more nerves surrounding the bladder.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

Embodiments of a tissue treatment system are described above. More particularly, embodiments of the tissue treatment system are described, either explicitly or implicitly. The following paragraphs summarize some of the described embodiments.

In an embodiment, a method includes filling a balloon with fluid within a body lumen. The method includes detecting a fluid parameter of the fluid over a period of time. The method includes determining a parameter curve of the fluid parameter. The parameter curve includes the fluid parameter versus an independent variable over the period of time. The parameter curve includes several inflections corresponding to changes in the fluid parameter. The method includes determining, based on one or more of the several inflections, a size of the body lumen or a neuromodulation parameter corresponding to the size of the body lumen.

In an embodiment, the fluid parameter is a pressure of the fluid. The independent variable is time.

In an embodiment, the fluid parameter is a pressure of the fluid. The independent variable is volume of the fluid.

In an embodiment, the fluid parameter is a differential flow rate of the fluid. The independent variable is time.

In an embodiment, the differential flow rate is a difference between an injection flow rate of the fluid being injected into the balloon and a withdrawal flow rate of the fluid being withdrawn from the balloon.

In an embodiment, the parameter curve includes a minimal slope segment between a first inflection and a second inflection. Determining the size of the body lumen or the neuromodulation parameter corresponding to the size of the body lumen is based on a duration between the first inflection and the second inflection.

In an embodiment, the parameter curve includes a third inflection after the second inflection. Determining the size of the body lumen or the neuromodulation parameter corresponding to the size of the body lumen is based on at least a portion of a duration between the second inflection and the third inflection.

In an embodiment, the parameter curve includes a first slope between the first inflection and the second inflection, and a second slope between the second inflection and the third inflection. The second slope is greater than the first slope.

In an embodiment, the method further includes selecting the neuromodulation parameter based on the size of the body lumen. The method further includes generating neuromodulation energy based on the neuromodulation parameter to treat tissue surrounding the body lumen.

In an embodiment, the method further includes determining the balloon is a non-compliant balloon. Determining the size of the body lumen or the neuromodulation parameter corresponding to the size of the body lumen based on the one or more of the several inflections is in response to the balloon being the non-compliant balloon.

In an embodiment, a tissue treatment system includes a catheter comprising a balloon mounted on a catheter shaft. The tissue treatment system includes one or more syringes to fill the balloon with fluid. The tissue treatment system include a non-transitory computer readable memory storing instructions. The tissue treatment system includes one or more processors configured to execute the stored instructions to cause the tissue treatment system to perform a method including filling a balloon with fluid within a body lumen. The method includes detecting a fluid parameter of the fluid over a period of time. The method includes determining a parameter curve of the fluid parameter. The parameter curve includes the fluid parameter versus an independent variable over the period of time. The parameter curve includes a several inflections corresponding to changes in the fluid parameter. The method includes determining, based on one or more of the several inflections, a size of the body lumen or a neuromodulation parameter corresponding to the size of the body lumen.

In an embodiment, the fluid parameter is a pressure of the fluid. The independent variable is time.

In an embodiment, the fluid parameter is a pressure of the fluid. The independent variable is volume of the fluid.

In an embodiment, the fluid parameter is a differential flow rate of the fluid. The independent variable is time.

In an embodiment, the differential flow rate is a difference between an injection flow rate of the fluid being injected into the balloon and a withdrawal flow rate of the fluid being withdrawn from the balloon.

In an embodiment, the parameter curve includes a minimal slope segment between a first inflection and a second inflection. Determining the size of the body lumen or the neuromodulation parameter corresponding to the size of the body lumen is based on a duration between the first inflection and the second inflection.

In an embodiment, the parameter curve includes a third inflection after the second inflection. Determining the size of the body lumen or the neuromodulation parameter corresponding to the size of the body lumen is based on at least a portion of a duration between the second inflection and the third inflection.

In an embodiment, the parameter curve includes a first slope between the first inflection and the second inflection, and a second slope between the second inflection and the third inflection. The second slope is greater than the first slope.

In an embodiment, the one or more processors are further configured to execute the stored instructions to cause the tissue treatment system to perform a method including selecting the neuromodulation parameter based on the size of the body lumen. The method includes generating neuromodulation energy based on the neuromodulation parameter to treat tissue surrounding the body lumen.

In an embodiment, the one or more processors are further configured to execute the stored instructions to cause the tissue treatment system to determine the balloon is a non-compliant balloon. Determining the size of the body lumen or the neuromodulation parameter corresponding to the size of the body lumen based on the one or more of the several inflections is in response to the balloon being the non-compliant balloon.

In an embodiment, the catheter further includes an ultrasound transducer within the balloon.

In an embodiment, a non-transitory computer readable medium storing instructions, which when executed by one or more processors of a tissue treatment system, cause the tissue treatment system to perform a method filling a balloon with fluid within a body lumen. The method includes detecting a fluid parameter of the fluid over a period of time. The method includes determining a parameter curve of the fluid parameter. The parameter curve includes the fluid parameter versus an independent variable over the period of time. The parameter curve includes several inflections corresponding to changes in the fluid parameter. The method includes determining, based on one or more of the several inflections, a size of the body lumen or the neuromodulation parameter corresponding to the size of the body lumen.

In an embodiment, the fluid parameter is a pressure of the fluid. The independent variable is time.

In an embodiment, the fluid parameter is a pressure of the fluid. The independent variable is volume of the fluid.

In an embodiment, the fluid parameter is a differential flow rate of the fluid. The independent variable is time.

In an embodiment, the differential flow rate is a difference between an injection flow rate of the fluid being injected into the balloon and a withdrawal flow rate of the fluid being withdrawn from the balloon.

In an embodiment, the parameter curve includes a minimal slope segment between a first inflection and a second inflection. Determining the size of the body lumen or the neuromodulation parameter corresponding to the size of the body lumen is based on a duration between the first inflection and the second inflection.

In an embodiment, the parameter curve includes a third inflection after the second inflection. Determining the size of the body lumen or the neuromodulation parameter corresponding to the size of the body lumen is based on at least a portion of a duration between the second inflection and the third inflection.

In an embodiment, the parameter curve includes a first slope between the first inflection and the second inflection, and a second slope between the second inflection and the third inflection. The second slope is greater than the first slope.

In an embodiment, the instructions, when executed by the one or more processors of the tissue treatment system, cause the tissue treatment system to perform the method further including selecting the neuromodulation parameter based on the size of the body lumen. The method includes generating neuromodulation energy based on the neuromodulation parameter to treat tissue surrounding the body lumen.

In an embodiment, the instructions, when executed by the one or more processors of the tissue treatment system, cause the tissue treatment system to perform the method further includes determining the balloon is a non-compliant balloon. Determining the size of the body lumen or the neuromodulation parameter corresponding to the size of the body lumen based on the one or more of the several inflections is in response to the balloon being the non-compliant balloon.

In an embodiment, a method includes filling a balloon with a fluid within a body lumen. The method includes detecting a fluid parameter of the fluid over a period of time. The method includes determining a parameter curve of the fluid parameter. The parameter curve includes the fluid parameter versus an independent variable over the period of time. The method includes comparing the parameter curve of the fluid parameter to a reference curve. The method includes determining, based on the comparison, a size of the body lumen or the neuromodulation parameter corresponding to the size of the body lumen.

In an embodiment, the method includes filling the balloon with fluid prior to inserting the balloon into the body lumen. The method includes detecting the fluid parameter of the fluid prior to inserting the balloon into the body lumen. The method includes generating the reference curve based on the detected fluid parameter prior to inserting the balloon into the body lumen.

In an embodiment, the balloon is submersed in a heated water bath when filling the balloon with fluid prior to inserting the balloon into the body lumen.

In an embodiment, the fluid parameter is a pressure of the fluid. The independent variable is time.

In an embodiment, the fluid parameter is a pressure of the fluid. The independent variable is volume of the fluid.

In an embodiment, the method includes comparing the parameter curve to the reference curve includes determining a ratio of an inflection of the parameter curve to a reference inflection of the reference curve. Determining the size of the body lumen or the neuromodulation parameter corresponding to the size of the body lumen is based on the ratio.

In an embodiment, the method includes determining a nominal diameter of the balloon. Determining the ratio is based on the nominal diameter of the balloon being less than a predetermined body lumen size.

In an embodiment, the method includes comparing the parameter curve to the reference curve includes determining a ratio of an end point of the parameter curve to a reference end point of the reference curve. Determining the size of the body lumen or the neuromodulation parameter corresponding to the size of the body lumen is based on the ratio.

In an embodiment, the method includes determining a nominal diameter of the balloon. Determining the ratio is based on the nominal diameter of the balloon being greater than a predetermined body lumen size.

In an embodiment, the method includes determining the balloon is a compliant balloon; and wherein determining the size of the body lumen or the neuromodulation parameter corresponding to the size of the body lumen based on the comparison is in response to the compliant balloon.

In an embodiment, a tissue treatment system includes a catheter comprising a balloon mounted on a catheter shaft. The tissue treatment system includes one or more syringes to fill the balloon with a fluid. The tissue treatment system includes a non-transitory computer readable memory storing instructions. The tissue treatment system includes one or more processors configured to execute the stored instructions to cause the tissue treatment system to perform a method including filling the balloon with the fluid within a body lumen. The method includes detecting a fluid parameter of the fluid over a period of time. The method includes determining a parameter curve of the fluid parameter. The parameter curve includes the fluid parameter versus an independent variable over the period of time. The method includes comparing the parameter curve of the fluid parameter to a reference curve. The method includes determining, based on the comparison, a size of the body lumen or a neuromodulation parameter corresponding to the size of the body lumen.

In an embodiment, the one or more processors are further configured to execute the stored instructions to cause the tissue treatment system to perform a method including filling the balloon with fluid prior to inserting the balloon into the body lumen. The method includes detecting the fluid parameter of the fluid prior to inserting the balloon into the body lumen. The method includes generating the reference curve based on the detected fluid parameter prior to inserting the balloon into the body lumen.

In an embodiment, the balloon is submersed in a heated water bath when filling the balloon with the fluid prior to inserting the balloon into the body lumen.

In an embodiment, the fluid parameter is a pressure of the fluid. The independent variable is time.

In an embodiment, the fluid parameter is a pressure of the fluid. The independent variable is volume of the fluid.

In an embodiment, comparing the parameter curve to the reference curve includes determining a ratio of an inflection of the parameter curve to a reference inflection of the reference curve. Determining the size of the body lumen or the neuromodulation parameter corresponding to the size of the body lumen is based on the ratio.

In an embodiment, the one or more processors are further configured to execute the stored instructions to cause the tissue treatment system to perform a method includes determining a nominal diameter of the balloon. Determining the ratio is based on the nominal diameter of the balloon being less than a predetermined body lumen size.

In an embodiment, comparing the parameter curve to the reference curve includes determining a ratio of an end point of the parameter curve to a reference end point of the reference curve. Determining the size of the body lumen or the neuromodulation parameter corresponding to the size of the body lumen is based on the ratio.

In an embodiment, the one or more processors are further configured to execute the stored instructions to cause the tissue treatment system to determine a nominal diameter of the balloon. Determining the ratio is based on the nominal diameter of the balloon being greater than a predetermined body lumen size.

In an embodiment, the one or more processors are further configured to execute the stored instructions to cause the tissue treatment system to determine the balloon is a compliant balloon. Determining the size of the body lumen or the neuromodulation parameter corresponding to the size of the body lumen based on the comparison is in response to the compliant balloon.

In an embodiment, the catheter further includes an ultrasound transducer within the balloon.

In an embodiment, a non-transitory computer readable medium storing instructions, which when executed by one or more processors of a tissue treatment system, cause the tissue treatment system to perform a method including filling a balloon with a fluid within a body lumen. The method includes detecting a fluid parameter of the fluid over a period of time. The method includes determining a parameter curve of the fluid parameter. The parameter curve includes the fluid parameter versus an independent variable over the period of time. The method includes comparing the parameter curve of the fluid parameter to a reference curve. The method includes determining, based on the comparison, a size of the body lumen or a neuromodulation parameter corresponding to the size of the body lumen.

In an embodiment, the instructions, when executed by the one or more processors of the tissue treatment system, cause the tissue treatment system to perform the method further including filling the balloon with the fluid prior to inserting the balloon into the body lumen. The method includes detecting the fluid parameter of the fluid prior to inserting the balloon into the body lumen. The method includes generating the reference curve based on the detected fluid parameter prior to inserting the balloon into the body lumen.

In an embodiment, the balloon is submersed in a heated water bath when filling the balloon with the fluid prior to inserting the balloon into the body lumen.

In an embodiment, the fluid parameter is a pressure of the fluid. The independent variable is time.

In an embodiment, the fluid parameter is a pressure of the fluid. The independent variable is volume of the fluid.

In an embodiment, the method includes comparing the parameter curve to the reference curve includes determining a ratio of an inflection of the parameter curve to a reference inflection of the reference curve. The method includes determining the size of the body lumen or the neuromodulation parameter corresponding to the size of the body lumen is based on the ratio.

In an embodiment, the instructions, when executed by the one or more processors of the tissue treatment system, cause the tissue treatment system to perform the method further including determining a nominal diameter of the balloon. Determining the ratio is based on the nominal diameter of the balloon being less than a predetermined body lumen size.

In an embodiment, the method includes comparing the parameter curve to the reference curve includes determining a ratio of an end point of the parameter curve to a reference end point of the reference curve. Determining the size of the body lumen or the neuromodulation parameter corresponding to the size of the body lumen is based on the ratio.

In an embodiment, the instructions, when executed by the one or more processors of the tissue treatment system, cause the tissue treatment system to perform the method further including determining a nominal diameter of the balloon. Determining the ratio is based on the nominal diameter of the balloon being greater than a predetermined body lumen size.

In an embodiment, the instructions, when executed by the one or more processors of the tissue treatment system, cause the tissue treatment system to perform the method further including determining the balloon is a compliant balloon. Determining the size of the body lumen or the neuromodulation parameter corresponding to the size of the body lumen based on the comparison is in response to the compliant balloon.

In an embodiment, a method includes detecting pressure of a fluid used to inflate a balloon within a body lumen over a period of time. The method includes determining a pressure-versus-time curve of the fluid based on the pressure over the period of time. The pressure-versus-time curve includes a minimal slope segment between a first non-minimal slope segment and a second non-minimal slope segment. The method includes determining a size of the body lumen or a neuromodulation parameter corresponding to the size of the body lumen based on a duration of the minimal slope segment.

In an embodiment, a method includes detecting pressure of a fluid used to inflate a balloon within a body lumen over a period of time. The method includes determining a pressure-versus-time curve of the fluid based on the pressure over the period of time. The pressure-versus-time curve includes a minimal slope environmental pressure segment before two or more non-minimal slope elevated pressure segments. The method includes determining a size of the body lumen or a neuromodulation parameter corresponding to the size of the body lumen based on a duration of the minimal slope segment.

In an embodiment, the method includes determining the size of the body lumen or the neuromodulation parameter corresponding to the size of the body lumen based on at least a portion of a duration of the two or more non-minimal slope elevated pressure segments.

In an embodiment, the method includes the non-minimal slope elevated pressure segments have respective grades increasing sequentially after the minimal slope environmental pressure segment.

In an embodiment, a method includes detecting pressure of a fluid used to inflate a balloon within a body lumen over a period of time. The method includes determining a pressure-versus-time curve of the fluid based on the pressure over the period of time. The pressure-versus-time curve includes a first non-minimal slope segment between a minimal slope segment and a second non-minimal slope segment. The method includes determining, in response to the first minimal slope segment having a lesser grade than the second minimal slope segment, a size of the body lumen or a neuromodulation parameter corresponding to the size of the body lumen based on a duration of the minimal slope segment.

In an embodiment, the method includes determining the balloon is a non-compliant balloon. The method includes determining the size of the body lumen or the neuromodulation parameter corresponding to the size of the body lumen based on the duration of the minimal slope segment is based on the balloon being the non-compliant balloon.

In an embodiment, a method includes detecting pressure of a fluid used to inflate a balloon within a body lumen over a period of time. The method includes determining a pressure-versus-time curve of the fluid based on the pressure over the period of time. The pressure-versus-time curve includes a minimal slope segment before a non-zero slope segment. The method includes determining, in response to the balloon being the compliant balloon, a non-aberrant portion of the non-zero slope segment and an aberrant portion of the non-zero slope segment. The non-aberrant portion matches a predetermined expected balloon-pressure time curve. The aberrant portion differs from the predetermined balloon-pressure time curve. The method includes determining a size of the body lumen or a neuromodulation parameter corresponding to the size of the body lumen based on a combined duration of the minimal slope segment and the non-aberrant portion of the first non-minimal slope segment.

In an embodiment, the method includes determining the balloon is a compliant balloon. Determining the size of the body lumen or the neuromodulation parameter corresponding to the size of the body lumen based on the combined duration of the minimal slope segment and the non-aberrant portion of the first non-minimal slope segment is based on the balloon being the compliant balloon.

In an embodiment, a method includes detecting pressure of a fluid used to inflate a balloon within a body lumen over a period of time. The method includes determining a pressure-versus-time curve based on the pressure over the period of time. The method includes determining a difference between the pressure-versus-time curve and a predetermined balloon-pressure time curve. The method includes displaying, in response to the difference, an error message indicating that the balloon is improperly sized for the body lumen.

In an embodiment, the pressure-versus-time curve and the predetermined balloon-pressure time curve include respective minimal slope segments before respective non-minimal slope segments. Determining the difference includes determining whether the minimal slope segment of the pressure-versus-time curve matches the minimal slope segment of the predetermined balloon-pressure time curve.

In an embodiment, determining the difference includes determining whether the non-minimal slope segment of the pressure-versus-time curve matches the non-minimal slope segment of the predetermined balloon-pressure time curve.

In an embodiment, a method includes detecting, over a period of time, a difference between an injection flow rate of a fluid being injected into a balloon and a withdrawal flow rate of the fluid being withdrawn from the balloon while the balloon is within a body lumen. The method includes determining a differential flow rate-versus-time curve based on the difference over the period of time. The differential flow rate-versus-time curve includes a minimal slope segment between a first non-minimal slope segment and a second non-minimal slope segment. The method includes determining a size of the body lumen or a neuromodulation parameter corresponding to the size of the body lumen based on a duration of the minimal slope segment.

In an embodiment, a method incudes exciting, at a first time, an ultrasound transducer to cause a first transducer segment of the ultrasound transducer to emit a first center frequency based on a first thickness of the first transducer segment and to cause a second transducer segment of the ultrasound transducer to emit a second center frequency based on a second thickness of the second transducer segment. The second thickness is different than the first thickness. The method includes receiving, by the first transducer segment of the ultrasound transducer at a second time, an ultrasound echo signal having the first center frequency. The method includes determining a size of the body lumen or a neuromodulation parameter corresponding to the size of the body lumen based on a difference between the first time and the second time.

In an embodiment, the first thickness is less than the second thickness, and wherein the first center frequency is greater than the second center frequency.

In an embodiment, the first center frequency is at least twice the second center frequency.

In an embodiment, the method includes selecting an ultrasound treatment parameter based on the size of the body lumen. The method includes exciting the ultrasound transducer using the ultrasound treatment parameter to cause the second transducer segment of the ultrasound transducer to emit ultrasound energy having the second center frequency to treat tissue surrounding the body lumen.

In an embodiment, a method includes exciting, at a first time, an ultrasound transducer to cause a pair of end transducer segments of the ultrasound transducer to emit a first center frequency based on a first thickness of the pair of end transducer segments and to cause a medial transducer segment of the ultrasound transducer to emit a second center frequency based on a second thickness of the medial transducer segment. The second thickness is different than the first thickness. The method includes receiving, by one or more of the pair of end transducer segments of the ultrasound transducer at a second time, an ultrasound echo signal having the first center frequency. The method includes determining a size of the body lumen or a neuromodulation parameter corresponding to the size of the body lumen based on a difference between the first time and the second time.

In an embodiment, the method includes the first thickness is less than the second thickness. The first center frequency is greater than the second center frequency.

In an embodiment, the first center frequency is at least twice the second center frequency.

In an embodiment, the method includes selecting an ultrasound treatment parameter based on the size of the body lumen. The method includes exciting the ultrasound transducer using the ultrasound treatment parameter to cause the second transducer segment of the ultrasound transducer to emit ultrasound energy having the second center frequency to treat tissue surrounding the body lumen.

In an embodiment, a method includes exciting an ultrasound transducer to cause a first transducer segment of the ultrasound transducer to emit a first center frequency based on a first thickness of the first transducer segment and to cause a second transducer segment of the ultrasound transducer to emit a second center frequency based on a second thickness of the second transducer segment. The second thickness is different than the first thickness. The method includes receiving, by the first transducer segment of the ultrasound transducer, a first ultrasound echo signal and a second ultrasound echo signal. The first ultrasound echo signal and the second ultrasound echo signal have a first center frequency. The first ultrasound echo signal has a first delay and the second ultrasound echo signal has a second delay. The method includes determining whether the ultrasound transducer is centered within a body lumen based on the first delay and the second delay.

In an embodiment, a method includes inflating a balloon between a first time and a second time within a body lumen. The balloon is mounted at a distal end of a catheter. The method includes detecting, by a sensor located distal to the balloon at the second time, a change in flow within the body lumen. The method includes determining, in response to detecting the change in flow at the second time, a size of the body lumen or a neuromodulation parameter corresponding to the size of the body lumen based on a difference between the first time and the second time.

In an embodiment, the sensor is located on a guidewire used to deliver a catheter having the balloon into the body lumen.

In an embodiment, the sensor is located on a guide sheath used to deliver a catheter having the balloon into the body lumen.

In an embodiment, a method includes receiving map information for several locations within at least one body lumen. The map information includes respective body lumen sizes at each of the several locations. The method includes determining a treatment plan for the at least one body lumen based on several compliance curves of a balloon. The several compliance curves correspond to sequential deployments of the balloon. The several compliance curves increase at each sequential deployment. The treatment plan includes deploying the balloon at the several locations in sequence from a first location having a smallest body lumen size to an nth location having a largest body lumen size. The method includes presenting the treatment plan on a display.

In an embodiment, the nth location is a fifth or greater location.

In an embodiment, the nth location is a second or greater location.

In an embodiment, the at least one body lumen includes at least one renal artery.

In an embodiment, the at least one body lumen includes at least one renal artery and at least one hepatic artery.

In an embodiment, the at least one body lumen includes at least one renal artery, hepatic artery, splenic artery, celiac trunk, superior mesenteric artery, or inferior mesenteric artery.

In an embodiment, the method includes ablating nerves of a patient, wherein the ablating nerves results in a decrease of sympathetic nerve activity in a patient.

In an embodiment, the method includes ablating renal nerves of a patient, wherein the ablating renal nerves results in lowering renal sympathetic nerve activity.

In an embodiment, the method includes ablating nerves of a patient using intravascular ultrasound ablation. The ablating nerves results in a decrease of sympathetic nerve activity in a patient without injury to the body lumen.

In an embodiment, the method includes ablating renal nerves of a patient. Ablating the renal nerves results in a therapeutically beneficial reduction in clinical symptoms of hypertension in the patient.

In an embodiment, the method includes ablating renal nerves using thermal ultrasound ablation. Ablating the renal nerves results in a therapeutically beneficial reduction in clinical symptoms of hypertension in the patient.

In an embodiment, the method includes ablating one or more nerves of a hepatic artery by delivering ablative radiofrequency energy or ultrasound to one or more nerves. The ablating results in disruption of neural communication.

In an embodiment, a method includes receiving map information for several locations within at least one body lumen. The map information includes respective body lumen sizes at each of the several locations. The method includes determining a treatment plan for the at least one body lumen based on several compliance curves of a balloon. The several compliance curves correspond to sequential deployments of the balloon. The several compliance curves increase at each sequential deployment. The treatment plan includes deploying the balloon at the several locations in sequence from a first location having a smallest body lumen size to an nth location having a largest body lumen size. The method includes selecting a first ablation location within one of the at least one body lumen. The method includes displaying the first ablation location on a user interface.

In an embodiment, the nth location is a third or greater location.

In an embodiment, the nth location is a fifth or greater location.

In an embodiment, the nth location is a second or greater location.

In an embodiment, the at least one body lumen includes at least one renal artery.

In an embodiment, the at least one body lumen includes at least one renal artery and at least one hepatic artery.

In an embodiment, the at least one body lumen includes at least one renal artery, hepatic artery, splenic artery, celiac trunk, superior mesenteric artery, and/or inferior mesenteric artery.

In an embodiment, a tissue treatment system, includes a catheter including a balloon mounted on a catheter shaft, and an ultrasound transducer within the balloon. The tissue treatment system includes a fluid transfer cartridge having one or more syringes to inject or withdraw fluid from the balloon. The tissue treatment system includes a non-transitory computer readable memory storing instructions. The tissue treatment system includes one or more processors configured to execute the stored instructions to cause the control unit to perform a method including receiving map information for several locations within at least one body lumen. The map information includes respective body lumen sizes at each of the several locations. The method includes determining a treatment plan for the at least one body lumen based on several compliance curves of a balloon. The several compliance curves correspond to sequential deployments of the balloon. The several compliance curves increase at each sequential deployment. The treatment plan includes deploying the balloon at the several locations in sequence from a first location having a smallest body lumen size to an nth location having a largest body lumen size. The method includes presenting the treatment plan on a display.

In an embodiment, the balloon has a durometer of 55 D.

In an embodiment, the balloon includes Isothane® having a durometer of 55 D.

In an embodiment, a tissue treatment system, includes a catheter including a balloon mounted on a catheter shaft, and an ultrasound transducer within the balloon. The tissue treatment system includes a fluid transfer cartridge having one or more syringes to inject or withdraw fluid from the balloon. The tissue treatment system includes a non-transitory computer readable memory storing instructions. The tissue treatment system includes one or more processors configured to execute the stored instructions to cause the system to perform a method including receiving map information for several locations within at least one body lumen. The map information includes respective body lumen sizes at each of the several locations. The method includes determining a treatment plan for the at least one body lumen based on several compliance curves of a balloon. The several compliance curves correspond to sequential deployments of the balloon. The several compliance curves increase at each sequential deployment. The treatment plan includes deploying the balloon at the several locations in sequence from a first location having a smallest body lumen size to an nth location having a largest body lumen size. The treatment plan includes selecting a first ablation location within one of the at least one body lumen, and displaying the first ablation location on a user interface.

In an embodiment, the nth location is a third or greater location.

In an embodiment, the nth location is a fifth or greater location.

In an embodiment, the nth location is a second or greater location.

In an embodiment, the at least one body lumen includes at least one renal artery.

In an embodiment, the at least one body lumen includes at least one renal artery and at least one hepatic artery.

In an embodiment, the at least one body lumen includes at least one renal artery, hepatic artery, splenic artery, celiac trunk, superior mesenteric artery, or inferior mesenteric artery.

In an embodiment, a tissue treatment system includes a catheter including a balloon mounted on a catheter shaft. The tissue treatment system includes a fluid transfer cartridge including one or more syringes to inject or withdraw fluid from the balloon. The tissue treatment system includes a non-transitory computer readable memory storing instructions. The tissue treatment system includes one or more processors configured to execute the stored instructions to cause the tissue treatment system to performs any of the methods described above.

In an embodiment, the catheter further includes an ultrasound transducer within the balloon.

In an embodiment, the catheter further includes several electrodes coupled to the balloon.

In an embodiment, a method for use with a tissue treatment system that includes a user interface and a catheter comprising a balloon and a fluid supply subsystem configured to provide fluid to the balloon. The method includes: (a) while the balloon is inserted into a portion of a body lumen of a patient, inflating the balloon using fluid; (b) while the balloon is being inflated, using one or more sensors to produce sensor measurements indicative of at least one of pressure or flow rate of the fluid being supplied to the balloon and/or being removed from the balloon; (c) determining, based on one or more of the sensor measurements, a time t1 when the balloon is sufficiently inflated such that the pressure of the balloon transitions from a vacuum pressure to an environmental pressure and a time t2 when the balloon is sufficiently inflated such that the balloon becomes in apposition with the portion of the body lumen; (d) determining an estimate of a size of the portion of the body lumen, or a surrogate thereof, based on at least one said sensor measurement obtained based on an amount of time between time t1 and time t2; and (e) displaying, on the user interface, the estimated size of the portion of the body lumen, or the surrogate thereof.

In an embodiment, the method includes (f) selecting at least one neuromodulation treatment parameter, for use in treating tissue surrounding the portion of the body lumen, based on the estimate of the size of the portion of the body lumen, or the surrogate thereof; and (g) generating a neuromodulation energy, using the at least one neuromodulation treatment parameter that is selected based on the estimate of the size of the portion of the body lumen, or the surrogate thereof, to thereby treat at least a portion of tissue surrounding the portion of the body lumen.

In an embodiment, the method includes (f) choosing a balloon catheter, for use in treating tissue surrounding the portion of the body lumen, based on the estimate of the size of the portion of the body lumen, or the surrogate thereof; and (g) inserting the balloon catheter into the body lumen.

In an embodiment, operation (b) includes using a first flow rate sensor to produce first flow rate measurements indicative of flow rate of the fluid being supplied to the balloon, and using a second flow rate sensor to produce second flow rate measurements indicative of flow rate of the fluid being removed from the balloon; and operation (c) includes determining differential flow rate measurements based on the first and second flow rate measurements, and determining, based on the differential flow rate measurements, when the balloon is sufficiently inflated such that the balloon becomes in apposition with the portion of the body lumen.

In an embodiment, operation (b) includes using a flow rate sensor to produce flow rate measurements indicative of a flow rate of blood within the body lumen in which the ultrasound transducer and the balloon are inserted; and operation (c) includes determining, based on the flow rate measurements, when the balloon is sufficiently inflated such that the balloon becomes in apposition with the portion of the body lumen.

In an embodiment, the flow rate sensor is located on a distal portion of a guide sheath or a guidewire that is used for inserting a distal portion of the catheter into the body lumen.

In an embodiment, operation (d) includes: (d.1) determining an estimate of a volume of the balloon when the balloon is sufficiently inflated such that the balloon becomes in apposition with the body lumen; and (d.2) determining the estimate of the size of the portion of the body lumen, or the surrogate thereof, based on the estimate of the volume of the balloon when the balloon is sufficiently inflated such that the balloon becomes in apposition with the body lumen.

In an embodiment, operation (d) includes: determining the estimate of the size of the portion of the body lumen, or the surrogate thereof, based on the volume of fluid supplied to the balloon between time t1 and time t2.

In an embodiment, the duration between t1 and t2 includes the surrogate of the estimate of the size of the portion of the body lumen; and operation (e) includes selecting the at least one ultrasound treatment parameter, for use in treating tissue surrounding the portion of the body lumen, based on the duration between t1 and t2.

In an embodiment, a tissue treatment system, includes a catheter including a catheter shaft having a distal end and a proximal end, first and second lumens extending longitudinally through the catheter shaft between the distal and the proximal ends thereof, an ultrasound transducer distally positioned relative to the distal end of the catheter shaft, and a balloon surrounding the ultrasound transducer; a fluid supply subsystem fluidically coupled to the first and second lumens of the catheter shaft and configured to provide fluid to the balloon via the first lumen and remove fluid from the balloon via the second lumen. The tissue treatment system includes one or more sensors configured to produce sensor measurements indicative of at least one of pressure or flow rate of the fluid being supplied to the balloon and/or being removed from the balloon, or of at least one of pressure or flow rate of blood within a body lumen in which the ultrasound transducer and the balloon are inserted. The tissue treatment system includes a controller configured to receive sensor measurements from the one or more sensors and to control the fluid supply subsystem and the ultrasound transducer. While the ultrasound transducer and the balloon are inserted into a portion of a body lumen of a patient, the controller is configured to: inflate the balloon using fluid; determine, based on one or more of the sensor measurements, when the balloon is sufficiently inflated such that the balloon becomes in apposition with the portion of the body lumen; determine an estimate of a size of the portion of the body lumen, or a surrogate thereof, based on at least one said sensor measurement obtained when the balloon is sufficiently inflated such that the balloon becomes in apposition with the body lumen, or based on an amount of time it took for the balloon to be sufficiently inflated such that the balloon becomes in apposition with the body lumen; and select at least one ultrasound treatment parameter, for use in treating tissue surrounding the portion of the body lumen, based on the estimate of the size of the portion of the body lumen, or the surrogate thereof; and excite the ultrasound transducer, using the at least one ultrasound treatment parameter that is selected based on the estimate of the size of the portion of the body lumen, or the surrogate thereof, to thereby treat at least a portion of tissue surrounding the portion of the body lumen.

In an embodiment, the one or more sensors include one or more pressure sensors configured to produce pressure measurements indicative of pressure of the fluid being supplied to the balloon and/or of the fluid being removed from the balloon. The controller is configured to determine, based on the pressure measurements, when the balloon is sufficiently inflated such that the balloon becomes in apposition with the portion of the body lumen.

In an embodiment, the one or more sensors include a pressure sensor configured to produce pressure measurements indicative of pressure of blood within the body lumen in which the ultrasound transducer and the balloon are inserted; and the controller is configured to determine, based on the pressure measurements, when the balloon is sufficiently inflated such that the balloon becomes in apposition with the portion of the body lumen.

In an embodiment, the system further includes a guide sheath and a guidewire that are used to insert a distal portion of the catheter shaft into the body lumen. The pressure sensor is located on a distal portion of the guide sheath or the guidewire.

In an embodiment, the one or more sensors include a first flow rate sensor configured to produce first flow rate measurements indicative of flow rate of the fluid being supplied to the balloon, and a second flow rate sensor configured to produce second flow rate measurements indicative of flow rate of the fluid being removed from the balloon. The controller is configured to determine differential flow rate measurements based on the first and second flow rate measurements, and determine, based on the differential flow rate measurements, when the balloon is sufficiently inflated such that the balloon becomes in apposition with the portion of the body lumen.

In an embodiment, the one or more sensors include a flow rate sensor configured to produce flow rate measurements indicative of a flow rate of blood within the body lumen in which the ultrasound transducer and the balloon are inserted. The controller is configured to determine, based on the flow rate measurements, when the balloon is sufficiently inflated such that the balloon becomes in apposition with the portion of the body lumen.

In an embodiment, the system further includes a guide sheath and a guidewire that are used to insert a distal portion of the catheter shaft into the body lumen. The flow rate sensor is located on a distal portion of the guide sheath or the guidewire.

In an embodiment, the controller is configured to determine an estimate of a volume of the balloon when the balloon is sufficiently inflated such that the balloon becomes in apposition with the body lumen. The controller is configured to determine the estimate of the size of the portion of the body lumen, or the surrogate thereof, based on the estimate of the volume of the balloon when the balloon is sufficiently inflated such that the balloon becomes in apposition with the body lumen.

In an embodiment, the controller is configured to determine the estimate of the size of the portion of the body lumen, or the surrogate thereof, based on the amount of time it took for the balloon to be sufficiently inflated such that the balloon becomes in apposition with the body lumen.

In an embodiment, the controller is configured to: determine, as the surrogate of the estimate of the size of the portion of the body lumen, the amount of time it took for the balloon to be sufficiently inflated such that the balloon becomes in apposition with the body lumen includes. The controller is configured to select the at least one ultrasound treatment parameter, for use in treating tissue surrounding the portion of the body lumen, based on the amount of time it took for the balloon to be sufficiently inflated such that the balloon becomes in apposition with the body lumen.

In an embodiment, a method for use with a tissue treatment system that includes a catheter including a catheter shaft having a distal end and a proximal end, first and second lumens extending longitudinally through the catheter shaft between the distal and the proximal ends thereof, an ultrasound transducer distally positioned relative to the distal end of the catheter shaft, a balloon surrounding the ultrasound transducer, and a fluid supply subsystem. The first lumen is configured to provide fluid from the fluid supply subsystem to the balloon, and the second lumen is configured to return fluid from the balloon to the fluid supply subsystem, the method comprising: (a) while the ultrasound transducer and the balloon are inserted into a portion of a body lumen of a patient, inflating the balloon using fluid; (b) while the balloon is being inflated, using one or more sensors to produce sensor measurements indicative of at least one of pressure or flow rate of the fluid being supplied to the balloon and/or being removed from the balloon, or of at least one of pressure or flow rate of blood within the body lumen in which the ultrasound transducer and the balloon are inserted; (c) determining, based on one or more of the sensor measurements, when the balloon is sufficiently inflated such that the balloon becomes in apposition with the portion of the body lumen; (d) determining an estimate of a size of the portion of the body lumen, or a surrogate thereof, based on at least one said sensor measurement obtained when the balloon is sufficiently inflated such that the balloon becomes in apposition with the body lumen, or based on an amount of time it took for the balloon to be sufficiently inflated such that the balloon becomes in apposition with the body lumen; and (e) selecting at least one ultrasound treatment parameter, for use in treating tissue surrounding the portion of the body lumen, based on the estimate of the size of the portion of the body lumen, or the surrogate thereof; and (f) exciting the ultrasound transducer, using the at least one ultrasound treatment parameter that is selected based on the estimate of the size of the portion of the body lumen, or the surrogate thereof, to thereby treat at least a portion of tissue surrounding the portion of the body lumen.

In an embodiment, operation (b) includes using one or more pressure sensors to produce pressure measurements indicative of pressure of the fluid being supplied to the balloon and/or of the fluid being removed from the balloon; and operation (c) includes determining, based on the pressure measurements, when the balloon is sufficiently inflated such that the balloon becomes in apposition with the portion of the body lumen.

In an embodiment, operation (b) includes using a pressure sensor to produce pressure measurements indicative of pressure of blood within the body lumen in which the ultrasound transducer and the balloon are inserted; operation (c) includes determining, based on the pressure measurements, when the balloon is sufficiently inflated such that the balloon becomes in apposition with the portion of the body lumen.

In an embodiment, the pressure sensor is located on a distal portion of a guide sheath or a guidewire that is used for inserting a distal portion of the catheter into the body lumen.

In an embodiment, operation (b) includes using a first flow rate sensor to produce first flow rate measurements indicative of flow rate of the fluid being supplied to the balloon, and using a second flow rate sensor to produce second flow rate measurements indicative of flow rate of the fluid being removed from the balloon; and operation (c) includes determining differential flow rate measurements based on the first and second flow rate measurements, and determining, based on the differential flow rate measurements, when the balloon is sufficiently inflated such that the balloon becomes in apposition with the portion of the body lumen.

In an embodiment, operation (b) includes using a flow rate sensor to produce flow rate measurements indicative of a flow rate of blood within the body lumen in which the ultrasound transducer and the balloon are inserted. Operation (c) includes determining, based on the flow rate measurements, when the balloon is sufficiently inflated such that the balloon becomes in apposition with the portion of the body lumen.

In an embodiment, the flow rate sensor is located on a distal portion of a guide sheath or a guidewire that is used for inserting a distal portion of the catheter into the body lumen.

In an embodiment, operation (d) includes: (d.1) determining an estimate of a volume of the balloon when the balloon is sufficiently inflated such that the balloon becomes in apposition with the body lumen; and (d.2) determining the estimate of the size of the portion of the body lumen, or the surrogate thereof, based on the estimate of the volume of the balloon when the balloon is sufficiently inflated such that the balloon becomes in apposition with the body lumen.

In an embodiment, operation (d) includes determining the estimate of the size of the portion of the body lumen, or the surrogate thereof, based on the amount of time it took for the balloon to be sufficiently inflated such that the balloon becomes in apposition with the body lumen.

In an embodiment, the amount of time it took for the balloon to be sufficiently inflated such that the balloon becomes in apposition with the body lumen includes the surrogate of the estimate of the size of the portion of the body lumen; and operation (e) includes selecting the at least one ultrasound treatment parameter, for use in treating tissue surrounding the portion of the body lumen, based on the amount of time it took for the balloon to be sufficiently inflated such that the balloon becomes in apposition with the body lumen.

In an embodiment, a tissue treatment system includes a catheter including a catheter shaft having a distal end and a proximal end, first and second lumens extending longitudinally through the catheter shaft between the distal and the proximal ends thereof. The tissue treatment system includes an ultrasound transducer distally positioned relative to the distal end of the catheter shaft, and a balloon surrounding the ultrasound transducer. The tissue treatment system includes a fluid supply subsystem fluidically coupled to the first and second lumens of the catheter shaft and configured to provide fluid to the balloon via the first lumen and remove fluid from the balloon via the second lumen. The tissue treatment system includes one or more sensors configured to produce sensor measurements indicative of at least one of pressure or flow rate of the fluid being supplied to the balloon and/or being removed from the balloon, or of at least one of pressure or flow rate of blood within a body lumen in which the ultrasound transducer and the balloon are inserted. The tissue treatment system includes a controller configured to receive sensor measurements from the one or more sensors and to control the fluid supply subsystem and the ultrasound transducer. While the ultrasound transducer and the balloon are inserted into a portion of a body lumen of a patient, the controller is configured to: inflate the balloon using fluid; determine, based on one or more of the sensor measurements, when the balloon is sufficiently inflated such that the balloon becomes in apposition with the portion of the body lumen; determine an estimate of a size of the portion of the body lumen, or a surrogate thereof, based on at least one said sensor measurement obtained when the balloon is sufficiently inflated such that the balloon becomes in apposition with the body lumen, or based on an amount of time it took for the balloon to be sufficiently inflated such that the balloon becomes in apposition with the body lumen; select at least one ultrasound treatment parameter, for use in treating tissue surrounding the portion of the body lumen, based on the estimate of the size of the portion of the body lumen, or the surrogate thereof; and excite the ultrasound transducer, using the at least one ultrasound treatment parameter that is selected based on the estimate of the size of the portion of the body lumen, or the surrogate thereof, to thereby treat at least a portion of tissue surrounding the portion of the body lumen.

In an embodiment, the one or more sensors include one or more pressure sensors configured to produce pressure measurements indicative of pressure of the fluid being supplied to the balloon and/or of the fluid being removed from the balloon. The controller is configured to determine, based on the pressure measurements, when the balloon is sufficiently inflated such that the balloon becomes in apposition with the portion of the body lumen.

In an embodiment, the one or more sensors include a pressure sensor configured to produce pressure measurements indicative of pressure of blood within the body lumen in which the ultrasound transducer and the balloon are inserted. The controller is configured to determine, based on the pressure measurements, when the balloon is sufficiently inflated such that the balloon becomes in apposition with the portion of the body lumen.

In an embodiment, the system further includes a guide sheath and a guidewire that are used to insert a distal portion of the catheter shaft into the body lumen. The pressure sensor is located on a distal portion of the guide sheath or the guidewire.

In an embodiment, the one or more sensors include a first flow rate sensor configured to produce first flow rate measurements indicative of flow rate of the fluid being supplied to the balloon, and a second flow rate sensor configured to produce second flow rate measurements indicative of flow rate of the fluid being removed from the balloon. The controller is configured to determine differential flow rate measurements based on the first and second flow rate measurements, and determine, based on the differential flow rate measurements, when the balloon is sufficiently inflated such that the balloon becomes in apposition with the portion of the body lumen.

In an embodiment, the one or more sensors include a flow rate sensor configured to produce flow rate measurements indicative of a flow rate of blood within the body lumen in which the ultrasound transducer and the balloon are inserted. The controller is configured to determine, based on the flow rate measurements, when the balloon is sufficiently inflated such that the balloon becomes in apposition with the portion of the body lumen.

In an embodiment, the system further includes a guide sheath and a guidewire that are used to insert a distal portion of the catheter shaft into the body lumen. The flow rate sensor is located on a distal portion of the guide sheath or the guidewire.

In an embodiment, the controller is configured to determine an estimate of a volume of the balloon when the balloon is sufficiently inflated such that the balloon becomes in apposition with the body lumen. The controller is configured to determine the estimate of the size of the portion of the body lumen, or the surrogate thereof, based on the estimate of the volume of the balloon when the balloon is sufficiently inflated such that the balloon becomes in apposition with the body lumen.

In an embodiment, the controller is configured to determine the estimate of the size of the portion of the body lumen, or the surrogate thereof, based on the amount of time it took for the balloon to be sufficiently inflated such that the balloon becomes in apposition with the body lumen.

In an embodiment, the controller is configured to determine, as the surrogate of the estimate of the size of the portion of the body lumen, the amount of time it took for the balloon to be sufficiently inflated such that the balloon becomes in apposition with the body lumen includes. The controller is configured to select the at least one ultrasound treatment parameter, for use in treating tissue surrounding the portion of the body lumen, based on the amount of time it took for the balloon to be sufficiently inflated such that the balloon becomes in apposition with the body lumen.

In an embodiment, a method for use with an ultrasound transducer that is inserted into a portion of a body lumen, wherein the ultrasound transducer includes a first transducer segment and a second transducer segment, the first transducer segment having a first thickness and configured to emit ultrasound energy having a first center frequency in response to the ultrasound transducer being excited using an excitation signal having the first center frequency, the second transducer segment having a second thickness and configured to emit ultrasound energy having a second center frequency in response to the ultrasound transducer being excited using an excitation signal having the second center frequency, the method including (a) exciting the ultrasound transducer with an excitation signal having the first center frequency to thereby cause the first transducer segment to emit ultrasound energy having the first center frequency. The method includes (b) receiving an ultrasound echo signal using the first transducer segment. The ultrasound echo signal includes a portion of the emitted ultrasound energy having the first center frequency that was reflected back towards the ultrasound transducer by a wall of the portion of the body lumen in which the ultrasound transducer is inserted. The method includes (c) determining an estimate of a size of the portion of the body lumen, or a surrogate thereof, based on the ultrasound echo signal that was received using the first transducer segment. The method includes (d) selecting at least one ultrasound treatment parameter, for use in treating tissue surrounding the portion of the body lumen using the second transducer segment, based on the estimate of the size of the portion of the body lumen, or the surrogate thereof, that was determined based on the ultrasound echo signal that was received using the first transducer segment. The method includes (e) exciting the ultrasound transducer with an excitation signal having the second center frequency and using the at least one ultrasound treatment parameter that was selected based on the estimate of the size of the portion of the body lumen, or the surrogate thereof, to thereby cause the second transducer segment to emit ultrasound energy having the second center frequency to treat at least a portion of tissue surrounding the portion of the body lumen.

In an embodiment, the at least one ultrasound treatment parameter, that is selected at operation (d) and used at operation (e), includes an acoustic output power level or a voltage level that is used to achieve that acoustic output power level.

In an embodiment, the ultrasound transducer includes cylindrical transducer body made of piezoelectric material. The first transducer segment includes a first longitudinal segment of the cylindrical transducer body. The second transducer segment includes a second longitudinal segment of the cylindrical transducer body, which is adjacent to and concentric with the first transducer segment. The first thickness corresponds to a thickness of the first longitudinal segment of the cylindrical transducer body, between a respective inner cylindrical surface and a respective outer cylindrical surface thereof. The second thickness corresponds to a thickness of the second longitudinal segment of the cylindrical transducer body, between a respective inner cylindrical surface and a respective outer cylindrical surface thereof.

In an embodiment, the first thickness is less than the second thickness. The first center frequency is greater than the second center frequency.

In an embodiment, the first center frequency is at least twice the second center frequency.

In an embodiment, the first thickness is greater than the second thickness. The first center frequency is less than the second center frequency.

In an embodiment, the second center frequency is at least twice the first center frequency.

In an embodiment, the first longitudinal segment of the cylindrical transducer body has a first longitudinal length; and the second longitudinal segment of the cylindrical transducer body has a second longitudinal length that is at least twice the first longitudinal length.

In an embodiment, the ultrasound transducer is located within an interior of a balloon within which the fluid is filled.

In an embodiment, a method for use with an ultrasound transducer that is inserted into a portion of a body lumen, the method including (a) exciting the ultrasound transducer with an excitation signal to thereby cause the ultrasound transducer to emit ultrasound energy. The method includes (b) receiving an ultrasound echo signal using the ultrasound transducer. The ultrasound echo signal includes a portion of the emitted ultrasound energy that was reflected back towards ultrasound transducer by a wall of the portion of the body lumen in which the ultrasound transducer is inserted. The method includes (c) determining, based on the ultrasound echo signal that is received, whether the ultrasound transducer is centered within the portion of the body lumen.

In an embodiment, the method includes (d) in response to determining that the ultrasound transducer is not centered within the portion of the body lumen, repositioning the ultrasound transducer within the portion of the body lumen or moving the ultrasound transducer to another portion of the body lumen, and then repeating operations (a), (b), and (c).

In an embodiment, after there is a determination that the ultrasound transducer is centered within the portion of the body lumen, the method further includes using the ultrasound transducer to emit further ultrasound energy that is used to treat at least a portion of tissue surrounding the portion of the body lumen.

In an embodiment, the ultrasound transducer includes a first transducer segment and a second transducer segment, the first transducer segment having a first thickness and configured to emit ultrasound energy having a first center frequency in response to the ultrasound transducer being excited using an excitation signal having the first center frequency, the second transducer segment having a second thickness and configured to emit ultrasound energy having a second center frequency in response to the ultrasound transducer being excited using an excitation signal having the second center frequency. Operation (a) includes exciting the ultrasound transducer with the excitation signal having the first center frequency to thereby cause the first transducer segment to emit ultrasound energy having the first center frequency. Operation (b) includes receiving the ultrasound echo signal using the first transducer segment.

In an embodiment, after there is a determination that the ultrasound transducer is centered within the portion of the body lumen, the method further includes: (d) determining an estimate of a size of the portion of the body lumen, or a surrogate thereof, based on the ultrasound echo signal, or a further ultrasound echo signal, that is received using the first transducer segment; (e) selecting at least one ultrasound treatment parameter, for use in treating tissue surrounding the portion of the body lumen using the second transducer segment, based on the estimate of the size of the portion of the body lumen, or the surrogate thereof, that was determined at operation (d); and (f) exciting the ultrasound transducer with an excitation signal having the second center frequency and using the at least one ultrasound treatment parameter that was selected based on the estimate of the size of the portion of the body lumen, or the surrogate thereof, to thereby cause the second transducer segment to emit ultrasound energy having the second center frequency to treat at least a portion of tissue surrounding the portion of the body lumen.

In an embodiment, a tissue treatment system, comprising: a catheter including a catheter shaft and an ultrasound transducer distally positioned relative to a distal end of the catheter shaft. The tissue treatment system includes a controller and an excitation source configured to generate, under control of the controller, excitation signals that are used to excite the ultrasound transducer. The excitation source may be part of the controller. The ultrasound transducer including a first transducer segment and a second transducer segment, the first transducer segment having a first thickness and configured to emit ultrasound energy having a first center frequency in response to the ultrasound transducer being excited using an excitation signal having the first center frequency, the second transducer segment having a second thickness and configured to emit ultrasound energy having a second center frequency in response to the ultrasound transducer being excited using an excitation signal having the second center frequency. The controller is configured to control the excitation source to excite the ultrasound transducer with an excitation signal having the first center frequency to thereby cause the first transducer segment to emit ultrasound energy having the first center frequency while the ultrasound transducer is inserted into a portion of a body lumen; the first transducer segment configured to receive an ultrasound echo signal that includes a portion of the emitted ultrasound energy having the first center frequency that was reflected back towards the ultrasound transducer by a wall of the portion of the body lumen in which the ultrasound transducer is inserted; the controller further configured to receive the ultrasound echo signal, or a signal indicative thereof, from the ultrasound transducer, and based thereon, determine an estimate of a size of the portion of the body lumen, or a surrogate thereof. The controller is configured to select at least one ultrasound treatment parameter, for use in treating tissue surrounding the portion of the body lumen using the second transducer segment, based on the estimate of the size of the portion of the body lumen, or the surrogate thereof, that was determined based on the ultrasound echo signal that was received using the first transducer segment. The controller is configured to control the excitation source to excite the ultrasound transducer with an excitation signal having the second center frequency and having the at least one ultrasound treatment parameter that was selected based on the estimate of the size of the portion of the body lumen, or the surrogate thereof, to thereby cause the second transducer segment to emit ultrasound energy having the second center frequency to treat at least a portion of tissue surrounding the portion of the body lumen.

In an embodiment, the at least one ultrasound treatment parameter includes an acoustic output power level or a voltage level that is used to achieve that acoustic output power level.

In an embodiment, the ultrasound transducer includes cylindrical transducer body made of piezoelectric material. The first transducer segment includes a first longitudinal segment of the cylindrical transducer body. The second transducer segment includes a second longitudinal segment of the cylindrical transducer body, which is adjacent to and concentric with the first transducer segment. The first thickness corresponds to a thickness of the first longitudinal segment of the cylindrical transducer body, between a respective inner cylindrical surface and a respective outer cylindrical surface thereof. The second thickness corresponds to a thickness of the second longitudinal segment of the cylindrical transducer body, between a respective inner cylindrical surface and a respective outer cylindrical surface thereof.

In an embodiment, the first thickness is less than the second thickness. The first center frequency is greater than the second center frequency.

In an embodiment, the first center frequency is at least twice the second center frequency.

In an embodiment, the first longitudinal segment of the cylindrical transducer body has a first longitudinal length. The second longitudinal segment of the cylindrical transducer body has a second longitudinal length that is at least twice the first longitudinal length.

In an embodiment, a system includes a balloon within which the fluid is filled and the ultrasound transducer is located.

In an embodiment, a tissue treatment system includes a catheter including a catheter shaft and an ultrasound transducer distally positioned relative to a distal end of the catheter shaft. A tissue treatment system includes a controller and an excitation source configured to generate, under control of the controller, excitation signals that are used to excite the ultrasound transducer, wherein the excitation source may be part of the controller. The controller is configured to control the excitation source to excite the ultrasound transducer with an excitation signal to thereby cause the ultrasound transducer to emit ultrasound energy. The transducer is configured to receive an ultrasound echo signal that includes a portion of the emitted ultrasound energy that was reflected back towards the ultrasound transducer by a wall of a portion of a body lumen in which the ultrasound transducer is inserted. The controller is further configured to receive the ultrasound echo signal, or a signal indicative thereof, from the ultrasound transducer, and based thereon, determine whether the ultrasound transducer is centered within the portion of the body lumen.

In an embodiment, after the controller determines that the ultrasound transducer is centered within the portion of the body lumen, the controller is further configured to control the excitation source to excite the ultrasound transducer with a further excitation signal to thereby cause the ultrasound transducer to emit further ultrasound energy that is used to treat at least a portion of tissue surrounding the portion of the body lumen in which the transducer is inserted.

In an embodiment, the ultrasound transducer includes a first transducer segment and a second transducer segment, the first transducer segment having a first thickness and configured to emit ultrasound energy having a first center frequency in response to the ultrasound transducer being excited using an excitation signal having the first center frequency, the second transducer segment having a second thickness and configured to emit ultrasound energy having a second center frequency in response to the ultrasound transducer being excited using an excitation signal having the second center frequency. The controller is configured to control the excitation source to excite the ultrasound transducer with an excitation signal having the first center frequency to thereby cause the first transducer segment to emit ultrasound energy having the first center frequency while the ultrasound transducer is inserted into the portion of the body lumen. The first transducer segment is configured to receive the ultrasound echo signal that includes a portion of the emitted ultrasound energy having the first center frequency that was reflected back towards the ultrasound transducer by a wall of the portion of the body lumen in which the ultrasound transducer is inserted. The controller is further configured to receive the ultrasound echo signal, or a signal indicative thereof, from the ultrasound transducer, and based thereon, determine an estimate of a size of the portion of the body lumen, or a surrogate thereof; select at least one ultrasound treatment parameter, for use in treating tissue surrounding the portion of the body lumen using the second transducer segment, based on the estimate of the size of the portion of the body lumen, or the surrogate thereof, that was determined based on the ultrasound echo signal that was received using the first transducer segment. The controller is configured to control the excitation source to excite the ultrasound transducer with an excitation signal having the second center frequency and having the at least one ultrasound treatment parameter that was selected based on the estimate of the size of the portion of the body lumen, or the surrogate thereof, to thereby cause the second transducer segment to emit ultrasound energy having the second center frequency to treat at least a portion of tissue surrounding the portion of the body lumen.

In an embodiment, the at least one ultrasound treatment parameter includes an acoustic output power level or a voltage level that is used to achieve that acoustic output power level.

In an embodiment, the ultrasound transducer includes cylindrical transducer body made of piezoelectric material. The first transducer segment includes a first longitudinal segment of the cylindrical transducer body. The second transducer segment includes a second longitudinal segment of the cylindrical transducer body, which is adjacent to and concentric with the first transducer segment. The first thickness corresponds to a thickness of the first longitudinal segment of the cylindrical transducer body, between a respective inner cylindrical surface and a respective outer cylindrical surface thereof. The second thickness corresponds to a thickness of the second longitudinal segment of the cylindrical transducer body, between a respective inner cylindrical surface and a respective outer cylindrical surface thereof.

In an embodiment, the first thickness is less than the second thickness. The first center frequency is greater than the second center frequency.

In an embodiment, the first center frequency is at least twice the second center frequency.

In an embodiment, the first longitudinal segment of the cylindrical transducer body has a first longitudinal length. The second longitudinal segment of the cylindrical transducer body has a second longitudinal length that is at least twice the first longitudinal length.

In an embodiment, a system includes a balloon within which the fluid is filled and the ultrasound transducer is located.

In an embodiment, a tissue treatment system, comprising: a catheter including a balloon mounted on a catheter shaft, and an ultrasound transducer within the balloon. The tissue treatment system includes a fluid transfer cartridge having one or more syringes to inject or withdraw fluid from the balloon; a non-transitory computer readable memory storing instructions. The tissue treatment system includes one or more processors configured to execute the stored instructions to cause the system to: detect a sound of the balloon beginning to expand (t1), detect that blood flow has stopped distal to the balloon (t2), determine a body lumen size based on the time between t1 and t2.

In an embodiment, a system includes means for detecting that a balloon has transitioned from a vacuum pressure to an environmental pressure (t1). The system includes means for detecting that the balloon is in apposition with a body lumen (t2). The system includes means for determining a body lumen diameter based on the difference between t1 and t2.

In an embodiment, a method for use with a tissue treatment system that includes a user interface and a catheter comprising a balloon and a fluid supply subsystem configured to provide fluid to the balloon, includes: inflating, while the balloon is inserted into a portion of a body lumen of a patient, the balloon using fluid; using, while the balloon is being inflated, one or more sensors to produce sensor measurements indicative of at least one of pressure or flow rate of the fluid being supplied to the balloon and/or being removed from the balloon; determining, based on one or more of the sensor measurements, a time t1 when the balloon is sufficiently inflated such that the pressure of the balloon transitions from a vacuum pressure to an environmental pressure and a time t2 when the balloon is sufficiently inflated such that the balloon becomes in apposition with the portion of the body lumen; determining an estimate of a size of the portion of the body lumen, or a surrogate thereof, based on at least one said sensor measurement obtained based on an amount of time between time t1 and time t2; and displaying, on the user interface, the estimated size of the portion of the body lumen, or the surrogate thereof.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method, comprising:
filling a balloon within a body lumen with a fluid;
detecting a fluid parameter of the fluid over a period of time;
determining a parameter curve of the fluid parameter, wherein the parameter curve includes the fluid parameter versus an independent variable over the period of time;
comparing the parameter curve of the fluid parameter to a reference curve, wherein comparing the parameter curve to the reference curve includes determining a ratio of a first independent-variable value at an inflection or an endpoint of the parameter curve to a second independent-variable value at a reference inflection or a reference endpoint of the reference curve; and
determining, based on the ratio, a size of the body lumen or a neuromodulation parameter corresponding to the size of the body lumen.

2. The method of claim 1 further comprising:
filling the balloon with the fluid prior to inserting the balloon into the body lumen;
detecting the fluid parameter of the fluid prior to inserting the balloon into the body lumen; and
generating the reference curve based on the detected fluid parameter prior to inserting the balloon into the body lumen.

3. The method of claim 2, wherein the balloon is submersed in a heated water bath when filling the balloon with the fluid prior to inserting the balloon into the body lumen.

4. The method of claim 1, wherein the fluid parameter is a pressure of the fluid, and wherein the independent variable is time.

5. The method of claim 1, wherein the fluid parameter is a pressure of the fluid, and wherein the independent variable is volume of the fluid.

6. The method of claim 1, wherein the first independent-variable value corresponds to the inflection of the parameter curve, and wherein the second independent-variable value corresponds to the reference inflection of the reference curve.

7. The method of claim 6 further comprising determining a nominal diameter of the balloon, wherein determining the ratio is based on the nominal diameter of the balloon being less than a predetermined body lumen size.

8. The method of claim 1, wherein the first independent-variable value corresponds to the end point of the parameter curve, and wherein the second independent-variable value corresponds to the reference end point of the reference curve.

9. The method of claim 8 further comprising determining a nominal diameter of the balloon, wherein determining the ratio is based on the nominal diameter of the balloon being greater than a predetermined body lumen size.

10. The method of claim 1 further comprising:
determining the balloon is a compliant balloon; and
wherein determining the size of the body lumen or the neuromodulation parameter corresponding to the size of the body lumen based on the comparison is in response to determining the balloon is the compliant balloon.

11. A tissue treatment system, comprising:
a catheter comprising a balloon mounted on a catheter shaft;
one or more syringes to fill the balloon with a fluid;
a non-transitory computer readable memory storing instructions; and
one or more processors configured to execute the stored instructions to cause the tissue treatment system to:
fill the balloon with the fluid within a body lumen;
detect a fluid parameter of the fluid over a period of time;
determine a parameter curve of the fluid parameter, wherein the parameter curve includes the fluid parameter versus an independent variable over the period of time;
compare the parameter curve of the fluid parameter to a reference curve, wherein comparing the parameter curve to the reference curve includes determining a ratio of a first independent-variable value at an inflection or an endpoint of the parameter curve to a second independent-variable value at a reference inflection or a reference endpoint of the reference curve; and
determining, based on the ratio, a size of the body lumen or a neuromodulation parameter corresponding to the size of the body lumen.

12. The tissue treatment system of claim 11, wherein the one or more processors are further configured to execute the stored instructions to cause the tissue treatment system to:
fill the balloon with the fluid prior to inserting the balloon into the body lumen;
detect the fluid parameter of the fluid prior to inserting the balloon into the body lumen; and
generate the reference curve based on the detected fluid parameter prior to inserting the balloon into the body lumen.

13. The tissue treatment system of claim 12 further comprising a heated water bath, wherein the one or more processors are further configured to execute the stored instructions to cause the tissue treatment system to fill the balloon when the balloon is submersed in the heated water bath prior to inserting the balloon into the body lumen.

14. The tissue treatment system of claim 11, wherein the fluid parameter is a pressure of the fluid, and wherein the independent variable is time.

15. The tissue treatment system of claim 11, wherein the fluid parameter is a pressure of the fluid, and wherein the independent variable is volume of the fluid.

16. The tissue treatment system of claim 11, wherein the first independent-variable value corresponds to the inflection of the parameter curve, and wherein the second independent-variable value corresponds to the reference inflection of the reference curve.

17. The tissue treatment system of claim 16, wherein the one or more processors are further configured to execute the stored instructions to cause the tissue treatment system to determine a nominal diameter of the balloon, wherein determining the ratio is based on the nominal diameter of the balloon being less than a predetermined body lumen size.

18. The tissue treatment system of claim 11, wherein the first independent-variable value corresponds to the end point of the parameter curve, and wherein the second independent-variable value corresponds to the reference end point of the reference curve.

19. The tissue treatment system of claim 18, wherein the one or more processors are further configured to execute the stored instructions to cause the tissue treatment system to determine a nominal diameter of the balloon, wherein determining the ratio is based on the nominal diameter of the balloon being greater than a predetermined body lumen size.

20. The tissue treatment system of claim 11, wherein the one or more processors are further configured to execute the stored instructions to cause the tissue treatment system to determine the balloon is a compliant balloon, and wherein determining the size of the body lumen or the neuromodulation parameter corresponding to the size of the body lumen based on the comparison is in response to determining the balloon is the compliant balloon.

21. The tissue treatment system of claim 11, wherein the catheter further comprises an ultrasound transducer within the balloon.

22. A non-transitory computer readable medium storing instructions, which when executed by one or more processors of a tissue treatment system, cause the tissue treatment system to perform a method, comprising:

filling a balloon with fluid within a body lumen;

detecting a fluid parameter of the fluid over a period of time;

determining a parameter curve of the fluid parameter, wherein the parameter curve includes the fluid parameter versus an independent variable over the period of time;

comparing the parameter curve of the fluid parameter to a reference curve, wherein comparing the parameter curve to the reference curve includes determining a ratio of a first independent-variable value at an inflection or an endpoint of the parameter curve to a second independent-variable value at a reference inflection or a reference endpoint of the reference curve; and determining, based on the ratio, a size of the body lumen or the neuromodulation parameter corresponding to the size of the body lumen.

23. The non-transitory computer readable medium of claim 22, wherein the instructions, when executed by the one or more processors of the tissue treatment system, cause the tissue treatment system to perform the method further comprising:

filling the balloon with the fluid prior to inserting the balloon into the body lumen;

detecting the fluid parameter of the fluid prior to inserting the balloon into the body lumen; and generating the reference curve based on the detected fluid parameter prior to inserting the balloon into the body lumen.

24. The non-transitory computer readable medium of claim 23, wherein the balloon is submersed in a heated water bath when filling the balloon prior to inserting the balloon into the body lumen.

25. The non-transitory computer readable medium of claim 22, wherein the fluid parameter is a pressure of the fluid, and wherein the independent variable is time.

26. The non-transitory computer readable medium of claim 22, wherein the fluid parameter is a pressure of the fluid, and wherein the independent variable is volume of the fluid.

27. The non-transitory computer readable medium of claim 22, wherein the first independent-variable value corresponds to the inflection of the parameter curve, and wherein the second independent-variable value corresponds to the reference inflection of the reference curve.

28. The non-transitory computer readable medium of claim 27, wherein the instructions, when executed by the one or more processors of the tissue treatment system, cause the tissue treatment system to perform the method further comprising further comprising determining a nominal diameter of the balloon, wherein determining the ratio is based on the nominal diameter of the balloon being less than a predetermined body lumen size.

29. The non-transitory computer readable medium of claim 22, wherein the first independent-variable value corresponds to the end point of the parameter curve, and wherein the second independent-variable value corresponds to the reference end point of the reference curve.

30. The non-transitory computer readable medium of claim 29, wherein the instructions, when executed by the one or more processors of the tissue treatment system, cause the tissue treatment system to perform the method further comprising further comprising determining a nominal diameter of the balloon, wherein determining the ratio is based on the nominal diameter of the balloon being greater than a predetermined body lumen size.

31. The non-transitory computer readable medium of claim 22, wherein the instructions, when executed by the one or more processors of the tissue treatment system, cause the tissue treatment system to perform the method further comprising further comprising:

determining the balloon is a compliant balloon; and wherein determining the size of the body lumen or the neuromodulation parameter corresponding to the size of the body lumen based on the comparison is in response to the compliant balloon.

* * * * *